(12) United States Patent
Hennequin

(10) Patent No.: US 7,501,516 B2
(45) Date of Patent: *Mar. 10, 2009

(54) QUINOLINE DERIVATIVES AND THEIR USE AS TYROSINE KINASE INHIBITORS

(75) Inventor: Laurent Francois Andre Hennequin, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 363 days.

This patent is subject to a terminal disclaimer.

(21) Appl. No.: 10/483,782

(22) PCT Filed: Jul. 10, 2002

(86) PCT No.: PCT/GB02/03177

§ 371 (c)(1),
(2), (4) Date: Aug. 11, 2004

(87) PCT Pub. No.: WO03/008409

PCT Pub. Date: Jan. 30, 2003

(65) Prior Publication Data

US 2005/0009867 A1    Jan. 13, 2005

(30) Foreign Application Priority Data

Jul. 16, 2001  (EP) .................. 01401895
Dec. 5, 2001   (EP) .................. 01403123

(51) Int. Cl.
C07D 215/12   (2006.01)
C07D 215/16   (2006.01)
C07D 265/30   (2006.01)
C07D 247/00   (2006.01)
A61K 31/472   (2006.01)

(52) U.S. Cl. .................. 546/139; 514/307; 544/106
(58) Field of Classification Search .................. 544/106; 514/307, 310, 231.2, 231.5; 546/139
See application file for complete search history.

(56) References Cited

U.S. PATENT DOCUMENTS

| | | | |
|---|---|---|---|
| 5,576,322 A | | 11/1996 | Takase et al. |
| 6,046,206 A | * | 4/2000 | Pamukcu et al. ........ 514/266.21 |
| 6,288,082 B1 | * | 9/2001 | Wissner et al. ............. 514/313 |
| 2006/0004017 A1 | * | 1/2006 | Stokes et al. ........... 514/252.17 |

FOREIGN PATENT DOCUMENTS

| | | | |
|---|---|---|---|
| WO | WO 9524190 | * | 9/1995 |
| WO | 97/44036 | | 11/1997 |
| WO | 97/44322 | | 11/1997 |
| WO | 98/13350 | | 4/1998 |
| WO | 98/20007 | | 5/1998 |
| WO | 98/43960 | | 10/1998 |
| WO | WO9843960 | * | 10/1998 |
| WO | 98/57936 | | 12/1998 |
| WO | 00/18761 A | | 4/2000 |
| WO | 00/50405 | | 8/2000 |
| WO | 00/68201 | | 11/2000 |
| WO | 01/12227 A1 | | 2/2001 |
| WO | 01/55116 A2 | | 8/2001 |
| WO | 01/72711 A1 | | 10/2001 |
| WO | 01/94341 | | 12/2001 |
| WO | 02/16352 A1 | | 2/2002 |
| WO | 02/30924 A1 | | 4/2002 |
| WO | 02/30926 A1 | | 4/2002 |
| WO | 02/34744 A1 | | 5/2002 |
| WO | 02/36570 A1 | | 5/2002 |
| WO | 02/44166 A1 | | 6/2002 |
| WO | 02/085895 A1 | | 10/2002 |
| WO | 03/000266 A1 | | 1/2003 |
| WO | 03/047584 A1 | | 6/2003 |
| WO | 03/048159 A1 | | 6/2003 |
| WO | 03/053960 A2 | | 7/2003 |
| WO | 2004/005284 A1 | | 5/2004 |

OTHER PUBLICATIONS

Inhibitors of Src tyrokinase inhibitors, Wang et al, 2000.*
Wang et al., "Inhibitors of Src Tyrosine Kinase: The Preparation and Structure-Activity Relationship of 4-Anilino-3-cyanoquinolines and 4-Anilinoquinazolines", Bioorganic and Medicinal Chemistry Letters, vol. 10, 2000, pp. 2477-2480, XP004224243, p. 2478, col. 2, para. 2, table 1.
Boschelli et al., "Optimization of 4-Phenylamino-3-quinolinecarbonitriles as Potent Inhibitors of Src Kinase Activity", J. Med. Chem., 2001, 44, 3965-3977.
Boschelli et al., J. Med. Chem, 2001, 44, 822-833.

* cited by examiner

*Primary Examiner*—Rita J Desai
(74) *Attorney, Agent, or Firm*—Morgan, Lewis & Bockius LLP

(57) ABSTRACT

The invention concerns quinoline derivatives of Formula (I) wherein each of Z, m, $R^1$, n and $R^3$ have any of the meanings defined in the description; processes for their preparation, pharmaceutical compositions containing them and their use in the manufacture of a medicament for use as an anti-invasive agent in the containment and/or treatment of solid tumour disease.

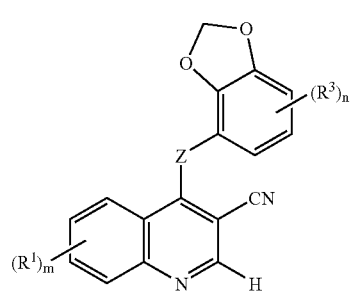

(I)

3 Claims, No Drawings

QUINOLINE DERIVATIVES AND THEIR USE AS TYROSINE KINASE INHIBITORS

The invention concerns certain novel quinoline derivatives, or pharmaceutically-acceptable salts thereof, which possess anti-tumour activity and are accordingly useful in methods of treatment of the human or animal body. The invention also concerns processes for the manufacture of said quinoline derivatives, pharmaceutical compositions containing them and their use in therapeutic methods, for example in the manufacture of medicaments for use in the prevention or treatment of solid tumour disease in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988 57, 443; Larsen et al., *Ann. Reports in Med. Chem.*, 1989, Chpt. 13). The first group of tyrosine kinases to be identified arose from such viral oncogenes, for example $pp60^{v-Src}$ tyrosine kinase (otherwise known as v-Src), and the corresponding tyrosine kinases in normal cells, for example $pp60^{c-Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGFI receptors and insulin-related receptor (IRR) and Class III receptor tyrosine kinases comprising the platelet-derived growth factor (PDGF) family of receptor tyrosine kinases such as the PDGFα, PDGFβ and colony-stimulating factor 1 (CSF1) receptors.

It is also known that certain tyrosine kinases belong to Me class of non-receptor tyrosine kinases which are located intracellularly and are involved in the transmission of biochemical signals such as those that influence tumour cell motility, dissemination and invasiveness and subsequently metastatic tumour growth (Ulkich et al., *Cell*, 1990, 61, 203-212, Bolen et al., *FASEB J.*, 1992, 6, 3403-3409, Brickell et al., *Critical Reviews in Oncogenesis*, 1992, 3, 401-406, Bohlen et al., *Oncogene*, 1993, 8 2025-2031, Courtneidge et al., *Semin. Cancer Biol.*, 1994, 5, 239-246, Lauffenburger et al., *Cell*, 1996, 84, 359-369, Hanks et al., *BioEssays*, 1996, 19, 137-145, Parsons et al., *Current Opinion in Cell Biology*, 1997, 9, 187-192, Brown et al., *Biochimica et Biophysica Acta*, 1996, 1287, 121-149 and Schlaepfer et al., *Progress in Biophysics and Molecular Biology*, 1999, 71, 435-478). Various classes of non-receptor tyrosine kinases are known including the Src-family such as the Src, Lyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, are frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87, 558-562 and Mao et al., *Oncogene*, 1997, 15, 3083-3090), and breast cancer (Muthuswamy et al., *Oncognen*, 1995, 11, 1801-1810). The Src family of non-receptor tyrosine kinases has also been located in other common human cancers such as non-small cell lung cancers (NSCLCs) including adenocarcinomas and squamous cell cancer of the lung (Mazurenko et al., *European Journal of Cancer*, 1992, 28, 372-7), bladder cancer (Fanning et al., *Cancer Research*, 1992, 52, 1457-62), oesophageal cancer (Jankowski et al., *Gut*, 1992, 33, 1033-8), cancer of the prostate, ovarian cancer (Wiener et al., *Clin. Cancer Research*, 1999, 5, 2164-70) and pancreatic cancer (Lutz et al., *Biochem. and Biophys. Res. Comm.*, 1998, 243, 503-8). As further human tumour tissues are tested for the Src family of non-receptor tyrosine kinases it is expected that its widespread prevalence will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, 11, 51-64 and Klinghoffer et al., *EMBO Journal*, 1999, 18, 2459-2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene*, 1997, 14, 283-293, Fincham et al., *EMBO J*, 1998, 17, 81-92 and Verbeek et al., *Exp. Cell Research*, 1999, 248, 531-537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

We have now found that surprisingly certain quinoline derivatives possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the non-receptor tyrosine-specific protein kinases that are involved in the signal transduction steps which lead to the invasiveness and migratory ability of metastasising tumour cells. In particular, it is believed that the compounds of the present invention provide an anti-tumour effect by way of inhibition of the Src family of non-receptor tyrosine kinases, for example by inhibition of one or more of c-Src, c-Yes and c-Fyn.

It is also known that c-Src non-receptor tyrosine kinase enzyme is involved in the control of osteoclast-driven bone resorption (Soriano et al., *Cell* 1991, 64, 693-702; Boyce et al., *J. Clin. Invest.*, 1992, 90, 1622-1627; Yoneda et al., *J. Clin. Invest.*, 1993, 91, 2791-2795 and Missbach et al., *Bone*, 1999, 24, 43749). An inhibitor of c-Src non-receptor tyrosine kinase is therefore of value in the prevention and treatment of bone diseases such as osteoporosis, Paget's disease, metastatic disease in bone and tumour-induced hypercalcaemia.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

Generally the compounds of the present invention possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase. Furthermore, certain compounds of the present invention possess substantially better potency against the Src family of non-receptor tyrosine kinases, for example c-Src and/or c-Yes, than against VEGF receptor tyrosine kinase. Such compounds possess sufficient potency against the Src family of non-receptor tyrosine kinases, for example c-Src and/or c-Yes, that they may be used in an amount sufficient to inhibit, for example, c-Src and/or c-Yes whilst demonstrating little activity against VEGF receptor tyrosine kinase.

It is stated in International Patent Application WO 98/43960 that a range of 3-cyanoquinoline derivatives are useful in the treatment of cancer. Certain of the compounds are stated to be inhibitors of EGF receptor tyrosine kinase, others are stated to be inhibitors of the mitogen-activated protein kinase, (MPK) pathway and others are stated to be inhibitors of growth factors such as vascular endothelial growth factor (VEGF). There is no disclosure therein of any 2,3-methylenedioxyphenyl-containing 3-cyanoquinoline derivatives.

It is stated in International Patent Application WO 00/68201 that a range of 3-cyanoquinoline derivatives are also useful in the treatment of cancer. Certain of the compounds are stated to be inhibitors of MEK, a MAPK kinase. There is no disclosure therein of any 2,3-methylenedioxyphenyl-containing 3-cyanoquinoline derivatives.

It is disclosed in *Journal Medicinal Chemistry*, 2001, 44, 822-833 that certain 4-anilino-3-cyanoquinoline derivatives are useful for the inhibition of Src-dependent cell proliferation. There is no disclosure therein of any 4-(2,3-methylenedioxyanilino)-3-cyanoquinoline derivatives.

According to one aspect of the invention there is provided a quinoline derivative of the Formula I

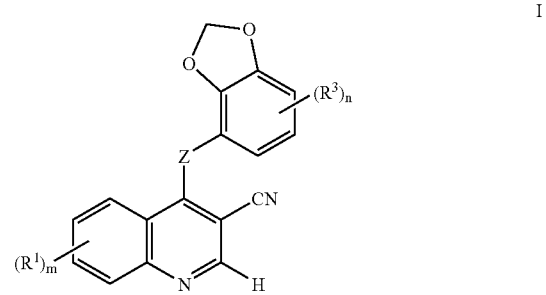

wherein Z is an O, S, SO, $SO_2$, $N(R^2)$ or $C(R^2)_2$ group, wherein each $R^2$ group, which may be the same or different, is hydrogen or (1-6C)alkyl;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkokycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$Q^1$-$X^1$— wherein $X^1$ is a direct bond or is selected from O, S, SO, $SO_2$, $NR^4$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$—, wherein $R^4$ is hydrogen or (1-6C)alkyl, and $Q^1$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R)_m$ is (1-3C)alkylenedioxy, and wherein adjacent carbon atoms in any (2-6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1-6C)alkyl or, when the inserted group is $N(R^5)$, $R^5$ may also be (2-6C)alkanoyl, and wherein any $CH_2$=CH— or HC≡C— group within a $R^1$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$Q^2$-$X^2$— wherein $X^2$ is a direct bond or is selected from CO and $N(R^6)CO$, wherein $R^6$ is hydrogen or (1-6C)alkyl, and $Q^2$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno or (1-6C)alkyl substituents or a substituent selected from hydroxy, cyano, amino, carboxy, carbamoyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6d)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^3$-$Q^3$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R)_2$, wherein $R^7$ is hydrogen or (1-6C)alkyl, and $Q^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-6C)alynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^4$—$R^8$ wherein $X^4$ is a direct bond or is selected from O and $N(R^9)$, wherein $R^9$ is hydrogen or (1-6C)alkyl, and $R^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, or from a group of the formula:

—$X^5$-$Q^4$ wherein $X^5$ is a direct bond or is selected from O, $N(R^{10})$ and CO, wherein $R^{10}$ is hydrogen or (1-6C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and wherein any heterocyclyl group within a substituent on $R^1$ optionally bears 1 or 2 oxo or thioxo substituents;

n is 0, 1, 2 or 3; and $R^3$ is halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^6$—$R^{11}$ wherein $X^6$ is a direct bond or is selected from O and $N(R^{12})$, wherein $R^{12}$ is hydrogen or (1-6C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

—$X^7$-$Q^5$ wherein $X^7$ is a direct bond or is selected from O, S, SO, $SO_2$, $N(R^{13})$, CO, $CH(OR^{13})$, $CON(R^{13})$, $N(R^{13})CO$, $SO_2N(R^{13})$, $N(R^{13})SO_2$, $C(R^{13})_2O$, $C(R^{13})_2S$ and $N(R^{13})C(R^{13})_2$, wherein $R^{13}$ is hydrogen or (1-6C)alkyl, and $Q^5$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and any heterocyclyl group within $Q^5$ optionally bears 1 or 2 oxo or thioxo substituents, or a pharmaceutically-acceptable salt thereof.

In this specification the generic term "alkyl" includes both straight-chain and branched-chain alkyl groups such as propyl, isopropyl and tert-butyl, and also (3-7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl] amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^5$) when it is aryl or for the aryl group within a 'Q' group is, for example, phenyl or naphthyl, preferably phenyl.

A suitable value for any one of the 'Q' groups ($Q^1$ or $Q^3$) when it is (3-7C)cycloalkyl or for the (3-7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$ or $Q^3$) when it is (3-7C)cycloalkenyl or for the (3-7C)cycloalkenyl group within a 'Q' group is, for example, cyclobutenyl, cyclopentenyl, cyclohexenyl or cycloheptenyl.

A suitable value for any one of the 'Q' groups ($Q^1$ to $Q^5$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^5$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, azetidinyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1,4thiazinyl, piperidinyl or piperazinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C)alkyl, (3-7C)cycloalkyl-(1-6C)alkyl, (3-7C)cycloalkenyl-(1-6C)alkyl or heterocyclyl-(1-6C)alkyl group is present.

In structural Formula I there is a hydrogen atom at the 2-position on the quinoline ring. It is to be understood thereby that the $R^1$ substituents may only be located at the 5-, 6-, 7- or 8-positions on the quinoline ring i.e. that the 2-position remains unsubstituted. It is further to be understood that the $R^3$ group that may be present on the 2,3-methylenedioxyphenyl group within structural Formula I may be located on the phenyl ring or on the methylene group within the 2,3-methylenedioxy group. Preferably, any $R^3$ group that is present on the 2,3-methylenedioxyphenyl group within structural Formula I is located on the phenyl ring thereof.

Suitable values for any of the 'R' groups ($R^1$ to $R^{13}$) or for various groups within an $R^1$ or $R^3$ substituent include:
for halogeno fluoro, chloro, bromo and iodo;
for (1-6C)alkyl: methyl, ethyl, propyl, isopropyl and tert-butyl;
for (2-8C)alkenyl: vinyl, isopropenyl, allyl and but-2-enyl;
for (2-8C)alkynyl: ethynyl, 2-propynyl and but-2-ynyl;
for (1-6C)alkoxy: methoxy, ethoxy, propoxy, isopropoxy and butoxy;
for (2-6C)alkenyloxy: vinyloxy and allyloxy;
for (2-6C)alkynyloxy: ethynyloxy and 2-propynyloxy;
for (1-6C)alkylthio: methylthio, ethylthio and propylthio;
for (1-6C)alkylsulphinyl: methylsulphinyl and ethylsulphinyl;
for (1-6C)alkylsulphonyl: methylsulphonyl and ethylsulphonyl;
for (1-6C)alkylamino: methylamino, ethylamino, propylamino, isopropylamino and butylamino;
for di-[(1-6C)alkyl]amino: dimethylamino, diethylamino, N-ethyl-N-methylamino and diisopropylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl and N-propylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl and propionyl;
for (2-6C)alkanoyloxy: acetoxy and propionyloxy;
for (2-6C)alkanoylamino: acetamido and propionamido;
for N-(1-6C)alkyl-(2-6C)alkanoylamino: N-methylacetamido and N-methylpropionamido;
for N-(1-6C)alkylsulphamoyl: N-methylsulphamoyl and N-ethylsulphamoyl;
for N,N-di-[(1-6C)alkyl]sulphamoyl: N,N-dimethylsulphamoyl;
for (1-6C)alkanesulphonylamino: methanesulphonylamino and ethanesulphonylamino;
for N-(1-6C)alkyl-(1-6C)alkanesulphonylamino: N-methylmethanesulphonylamino and N-methylethanesulphonylamino;
for (3-6C)alkenoylamino: acrylamido, methacrylamido and crotonamido;
for N-(1-6C)alkyl-(3-6C)alkenoylamino: N-methylacrylamido and N-methylcrotonamido;
for (3-6C)alkynoylamino: propiolamido;
for N-(1-6C)alkyl-(3-6C)alkynoylamino: N-methylpropiolamido;
for amino-(1-6C)alkyl: aminomethyl, 2-aminoethyl, 1-aminoethyl and 3-aminopropyl;
for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;
for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl;
for halogeno-(1-6C)alkyl: chloromethyl, 2-chloroethyl, 1-chloroethyl and 3-chloropropyl;
for hydroxy-(1-6C)alkyl: hydroxymethyl, 2-hydroxyethyl, 1-hydroxyethyl and 3-hydroxypropyl;
for (1-6C)alkoxy-(1-6C)allyl: methoxymethyl, ethoxymethyl, 1-methoxyethyl, 2-methoxyethyl, 2-ethoxyethyl and 3-methoxypropyl;
for cyano-(1-6C)alkyl: cyanomethyl, 2-cyanoethyl, 1-cyanoethyl and 3-cyanopropyl;
for (2-6C)alkanoylamino-(1-6C)alkyl: acetamidomethyl, propionamidomethyl, and 2-acetamidoethyl; and
for (1-6C)alkoxycarbonylamino-(1-6C)alkyl: methoxycarbonylaminomethyl, ethoxycarbonylaminomethyl, tert-butoxycarbonylaminomethyl and 2-methoxycarbonylaminoethyl.

A suitable value for $(R^1)_m$ when it is a (1-3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^1$-$X^1$— and, for example, $X^1$ is a $OC(R^4)_2$ linking group, it is the carbon atom, not the oxygen atom, of the OC(R$^4$)$_2$ linking group which is attached to the quinoline ring and the oxygen atom is attached to the Q$^1$ group. Similarly, when, for example a CH$_3$ group within a R$^1$ substituent bears a group of the formula —X$^3$-Q$^3$ and, for example, X$^3$ is a C(R$^7$)$_2$O linking group, it is the carbon atom, not the oxygen atom, of the C(R$^7$)$_2$O linking group which is attached to the CH$_3$ group and the oxygen atom is linked to the Q$^3$ group. A similar convention applies to the attachment of the groups of the formulae Q$^2$-X$^2$— and —X$^7$-Q$^5$.

As defined hereinbefore, adjacent carbon atoms in any (2-6C)alkylene chain within a R$^1$ substituent may be optionally separated by the insertion into the chain of a group such as O, CON(R$^5$) or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetaimido)ethoxy group.

When, as defined hereinbefore, any CH$_2$=CH— or HC≡C— group within a R$^1$ substituent optionally bears at the terminal CH$_2$= or HC≡ position a substituent such as a group of the formula Q$^2$-X$^2$— wherein X$^2$ is, for example, NHCO and Q$^2$ is a heterocyclyl-(1-6C)alkyl group, suitable R$^1$ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C) alkyl]carbamoylethynyl groups such as N-(2-pyrrolidin-1-ylethyl)carbamoylethynyl.

When, as defined hereinbefore, any CH$_2$ or CH$_3$ group within a R$^1$ substituent optionally bears on each said CH$_2$ or CH$_3$ group one or more halogeno or (1-6C)alkyl substituents, there are suitably 1 or 2 halogeno or (1-6C)alkyl substituents present on each said CH$_2$ group and there are suitably 1, 2 or 3 such substituents present on each said CH$_3$ group.

When, as defined hereinbefore, any CH$_2$ or CH$_3$ group within a R$^1$ substituent optionally bears on each said CH$_2$ or CH$_3$ group a substituent as defined hereinbefore, suitable R$^1$ substituents so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted amino-(2-6C)alkoxy groups such as 3-amino-2-hydroxypropoxy, hydroxy-substituted (1-6C) alkylamino-(2-6C)alkoxy groups such as 2-hydroxy-3-methylaminopropoxy, hydroxy-substituted di-[(1-6C)alkyl] amino-(2-6C)alkoxy groups such as 3-dimethylamino-2-hydroxypropoxy, hydroxy-substituted heterocyclyl-(1-6C) alkylamino groups such as 2-hydroxy-3-piperidinopropylamino and 2-hydroxy-3-morpholinopropylamino, hydroxy-substituted amino-(2-6C) alkylamino groups such as 3-amino-2-hydroxypropylamino, hydroxy-substituted (1-6C)alkylamino-(2-6C)alkylamino groups such as 2-hydroxy-3-methylaminopropylamino, hydroxy-substituted di-[(1-6C)alkyl]amino-(2-6C)alkylamino groups such as 3-dimethylamino-2-hydroxypropylamino, hydroxy-substituted (1-6C)alkoxy groups such as 2-hydroxyethoxy, (1-6C)alkoxy-substituted (1-6C)alkoxy groups such as 2-methoxyethoxy and 3-ethoxypropoxy, (1-6C)alkylsulphonyl-substituted (1-6C)alkoxy groups such as 2-methylsulphonylethoxy and heterocyclyl-substituted (1-6C)alkylamino-(1-6C)alkyl groups such as 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinoline derivatives of the Formula I, or pharmaceutically-acceptable salts thereof, wherein, unless otherwise stated, each of Z, m, R$^1$, n and R$^3$ has any of the meanings defined hereinbefore or in paragraphs (a) to (s) hereinafter:—

(a) Z is O, S, SO, SO$_2$, CH$_2$ or NH;
(b) Z is O;
(c) Z is NH;
(d) m is 1 or 2, and each R$^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl, N,N-di-[(1-6C)alkyl]carbamoyl, (2-6C)alkanoylamino, N-(1-6C) alkyl-(2-6C)alkylanoylamino, (3-6C)alkenoylamino, N-(1-6C)alkyl-(3-6C)alkenoylamino, (3-6C)alkynoylamino and N-(1-6C)alkyl-(3-6C)alkynoylamino, or from a group of the formula:

Q$^1$-X$^1$— wherein X$^1$ is a direct bond or is selected from O, N(R$^4$), CON(R$^4$), N(R$^4$)CO and OC(R$^4$)$_2$ wherein R$^4$ is hydrogen or (1-6C)alkyl, and Q$^1$ is aryl, aryl-(1-6C)alkyl, cycloalkyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a R$^1$ substituent are optionally separated by the insertion into the chain of a group selected from O, N(R$^5$), CON(R$^5$), N(R$^5$)CO, CH=CH and C≡C wherein R$^5$ is hydrogen or (1-6C)alkyl, or, when the inserted group is N(R$^5$), R$^5$ may also be (2-6C)alkanoyl, and wherein any CH$_2$=CH— or HC≡C— group within a R$^1$ substituent optionally bears at the terminal CH$_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C) alkyl and di-[(1-6C)alkyl]amino-(1-6C)alkyl or from a group of the formula:

Q$^2$-X$^2$— wherein X$^2$ is a direct bond or is CO or N(R$^6$)CO, wherein R$^6$ is hydrogen or (1-6C)alkyl, and Q$^2$ is heteroaryl, heteroaryl-(1-6C)alkyl, heterocyclyl or heterocyclyl-(1-6C)alkyl, and wherein any CH$_2$ or CH$_3$ group within a R$^1$ substituent optionally bears on each said CH$_2$ or CH$_3$ group one or more halogeno groups or a substituent selected from hydroxy, amino, (1-6C)alkoxy, (1-6C)alkylsulphonyl, (1-6C)alkylamino, di-[(1-6C)alkyl]amino, (2-6C)alkanoyloxy, (2-6C)alkanoylamino and N-(1-6C)alkyl-(2-6C)alkanoylamino, or from a group of the formula:

—X$^3$-Q$^3$ wherein X$^3$ is a direct bond or is selected from O, N(R$^6$), CON(R$^7$), N(R$^7$)CO and C(R$^7$)$_2$O, wherein R$^7$ is hydrogen or (1-6C)alkyl, and Q$^3$ is heteroaryl, heteroaryl-(1-6C)alkyl, heterocyclyl or heterocyclyl-(1-6C)alkyl, and wherein any aryl, heteroaryl or heterocyclyl group within a substituent on R$^1$ optionally bears 1, 2 or 3 substituents, which may be the same or different, selected from halogeno, trifluoromethyl, hydroxy, amino, carbamoyl, (1-6C)alkyl, (1-6C)alkoxy, N-(1-6C)alkylcarbamoyl and N,N-di-[(1-6C)alkyl]carbamoyl, optionally bears 1 substituent selected from a group of the formula:

—$X^4$—$R^8$ wherein $X^4$ is a direct bond or is selected from O and N($R^9$), wherein $R^9$ is hydrogen or (1-6C)alkyl, and $R^8$ is hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, and from a group of the formula:

—$X^5$-$Q^4$ wherein $X^5$ is a direct bond or is selected from O, N($R^{10}$) and CO, wherein $R^{10}$ is hydrogen or (1-6C)alkyl, and $Q^4$ is heterocyclyl or heterocyclyl-(1-6C)alkyl which optionally bears 1 or 2 substituents, which may be the same or different, selected from halogeno, (1-6C)alkyl and (1-6C)alkoxy, and wherein any heterocyclyl group within a substituent on $R^1$ optionally bears 1 or 2 oxo substituents;

(e) m is 1 or 2, and each R group, which may be the same or different, is selected from fluoro, chloro, trifluoromethyl, hydroxy, amino, carbamoyl, methyl, ethyl, propyl, butyl, vinyl, ethynyl, methoxy, ethoxy, propoxy, isopropoxy, butoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$Q^1$-$X^1$— wherein $X^1$ is a direct bond or is selected from O, NH, CONH, NHCO and OCH$_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazinyl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a $R^1$ substituent are optionally separated by the insertion into the chain of a group selected from O, NH, CONH, NHCO, CH═CH and C≡C, and wherein any CH$_2$═CH— or HC≡C— group within a $R^1$ substituent optionally bears at the terminal CH$_2$═ or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$Q^2$-$X^2$— wherein $X^2$ is a direct bond or is CO, NHCO or N(Me)CO and $Q^2$ is pyridyl, pyridylmethyl, 2-pyridylethyl, pyrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH$_2$ or CH$_3$ group within a $R^1$ substituent optionally bears on each said CH$_2$ or CH$_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido or from a group of the formula:

—$X^3$-$Q^3$ wherein $X^3$ is a direct bond or is selected from O, NH, CONH, NHCO and CH$_2$O and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl, or optionally bears 1 substituent selected from a group of the formula:

—$X^4$—$R^8$ wherein $X^4$ is a direct bond or is selected from O and NH and $R^8$ is 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^5$-$Q^4$ wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(f) m is 1 and the $R^1$ group is located at the 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, vinyl, ethynyl, methoxy, ethoxy, propoxy, isopropoxy, butoxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, 4pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4piperazin-1-ylbutylamino, 2-homopiperazin-1-ylethylamino or 3-homopiperazin-1-ylpropylamino, and wherein adjacent carbon atoms in any (2-6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2=$ or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$Q^2-X^2-$ wherein $X^2$ is a direct bond or is NHCO or N(Me)CO and $Q^2$ is imidazolylmethyl, 2-imidazolylethyl, 3-imidazolylpropyl, pyridylmethyl, 2-pyridylethyl, 3-pyridylpropyl, pyrrolidin-1-ylmethyl-2-pyrrolidin-1-ylethyl-3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, N-methylcarbamoyl, N,N-dimethylcarbamoyl and methoxy, and a pyrrolidin-2-yl, piperidin-3-yl, piperidin-4-yl, piperazin-1-yl or homopiperazin-1-yl group within a $R^1$ substituent is optionally N-substituted with 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(g) m is 1 and the $R^1$ group is located at the 6- or 7-position and is selected from hydroxy, amino, methyl, ethyl, propyl, butyl, methoxy, ethoxy, propoxy, isopropoxy, butoxy, methylamino, ethylamino, dimethylamino, diethylamino, acetamido, propionamido, benzyloxy, 2-imidazol-1-ylethoxy, 2-(1,2,3-triazol-1-yl)ethoxy, 2-(1,2,4-triazol-1-yl)ethoxy, 2-pyrrolidin-1-ylethoxy, 3-pyrrolidin-1-ylpropoxy, 4pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2-6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group one or more chloro groups or a substituent selected from hydroxy, amino, methoxy, methylsulphonyl, methylamino, dimethylamino, diisopropylamino, N-ethyl-N-methylamino, N-isopropyl-N-methylamino and acetoxy, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(h) n is 0;

(i) n is 1 or 2 and the $R^3$ groups, which may be the same or different, are located at the 5- and/or 6-positions of the 2,3-methylenedioxyphenyl group and are selected from halogeno, trifluoromethyl, cyano, hydroxy, (1-6C)alkyl, (2-8C)alkenyl, (2-8C)alkynyl and (1-6C)alkoxy;

(j) n is 1 or 2 and the $R^3$ groups, which may be the same or different, are located at the 5- and/or 6-positions of the 2,3-methylenedioxyphenyl group and are selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy;

(k) n is 1 and the $R^3$ group is located at the 5- or 6-position of the 2,3-methylenedioxyphenyl group, especially the 6-position, and is selected from chloro, bromo, trifluoromethyl, cyano, hydroxy, methyl, ethyl, methoxy and ethoxy;

(l) m is 1 or 2, and each $R^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl, N,N-di-[(1-6C)alkyl]carbamoyl, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino and N-(1-6C)alkyl-(3-6C)alkynoylamino, or from a group of the formula:

$Q^1$-$X^1$— wherein $X^1$ is a direct bond or is selected from O, N($R^4$), CON($R^4$), N($R^4$)CO and OC($R^4$)$_2$ wherein $R^4$ is hydrogen or (1-6C)alkyl, and $Q^1$ is aryl, aryl-(1-6C)alkyl, cycloalkyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1-6C)alkyl, or, when the inserted group is N($R^5$), $R^5$ may also be (2-6C)alkanoyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$Q^2$-$X^2$— wherein $X^2$ is a direct bond or is CO or N($R^6$)CO, wherein $R^6$ is hydrogen or (1-6C)alkyl, and $Q^2$ is heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno groups or a substituent selected from hydroxy, amino, (1-6C)alkoxy, (1-6C)alkylsulphonyl, (1-6C)alkylamino, di-[(1-6C)alkyl]amino, (2-6C)alkanoyloxy, (2-6C)alkanoylamino and N-(1-6C)alkyl-(2-6C)alkanoylamino, or from a group of the formula:

—$X^3$-$Q^3$ wherein $X^3$ is a direct bond or is selected from O, N($R^6$), CON($R^7$), N($R^7$)CO and C($R^7$)$_2$O, wherein $R^7$ is hydrogen or (1-6C)alkyl, and $Q^3$ is heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1-6C)alkyl, (2-8C)alkenyl, (2-8C)alkynyl, (1-6C)alkoxy, (1-6C)alkylsulphonyl, N-(1-6C)alkylcarbamoyl, N,N-di-[(1-6C)alkyl]carbamoyl and (2-6C)alkanoyl, or optionally bears 1 substituent selected from a group of the formula:

—$X^4$—$R^8$ wherein $X^4$ is a direct bond or is selected from O and N($R^9$), wherein $R^9$ is hydrogen or (1-6C)alkyl, and $R^8$ is hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, and from a group of the formula:

—$X^5$-$Q^4$ wherein $X^5$ is a direct bond or is selected from O, N($R^{10}$) and CO, wherein $R^{10}$ is hydrogen or (1-6C)alkyl, and $Q^4$ is heterocyclyl or heterocyclyl-(1-6C)alkyl which optionally bears 1 or 2 substituents, which may be the same or different, selected from halogeno, (1-6C)alkyl and (1-6C)alkoxy, and wherein any heterocyclyl group within a substituent on $R^1$ optionally bears 1 or 2 oxo substituents;

(m) m is 1 or 2, and each $R^1$ group, which may be the same or different, is selected from fluoro, chloro, trifluoromethyl, hydroxy, amino, carbamoyl, methyl, ethyl, propyl, butyl, vinyl, allyl, but-3-enyl, pent-4-enyl, hex-5-enyl, ethynyl, 2-propynyl, but-3-ynyl, pent-4ynyl, hex-5-ynyl, methoxy, ethoxy, propoxy, isopropoxy, butoxy, allyloxy, but-3-enyloxy, pent-4-enyloxy, hex-5-enyloxy, ethynyloxy, 2-propynyloxy, but-3-ynyloxy, pent-4-ynyloxy, hex-5-ynyloxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$Q^1$-$X^1$— wherein $X^1$ is a direct bond or is selected from O, NH, CONH, NHCO and $OCH_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl) propyl, 2-(1,2,4-triazolyl)ethyl, 3-(1,2,4-triazolyl)propyl, 2-, 3- or 4-pyridylmethyl, 2-(2-, 3- or 4pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl 3-piperazin-1-ylpropyl, 4-piperazin-1-ylbutyl, 2-homopiperazin-1-ylethyl or. 3-homopiperazin-1-ylpropyl, and wherein adjacent carbon atoms in any (2-6C)alkylene chain within a $R^1$ substituent are optionally separated by the insertion into the chain of a group selected from O, NH, N(Me), CONH, NHCO, CH=CH and C≡C, and wherein any $CH_2$=CH— or HC≡C— group within a $R^1$ substituent optionally bears at the terminal $CH_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$Q^2$-$X^2$— wherein $X^2$ is a direct bond or is CO, NHCO or N(Me)CO and $Q^2$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4piperazin-1-ylbutyl, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methyl amino, dimethylamino, diisopropylamino, N-ethyl-N-methylamino, N-isopropyl-N-methylamino, N-methyl-N-propylamino, acetoxy, acetamido and N-methylacetamido or from a group of the formula:

—$X^3$-$Q^3$ wherein $X^3$ is a direct bond or is selected from O, NH, CONH, NHCO and $CH_2$O and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^4$—$R^8$ wherein $X^4$ is a direct bond or is selected from O and NH and $R^8$ is 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^5$-$Q^4$ wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(n) m is 1 and the $R^1$ group is located at the 5-, 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, vinyl, ethynyl, methoxy, ethoxy, propoxy, isopropoxy, butoxy, pentyloxy, but-3-enyloxy, pent-4-enyloxy, hex-5-enyloxy, but-3-ynyloxy, pent-4-ynyloxy, hex-5-ynyloxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein adjacent carbon atoms in any (2-6C)alkylene chain within a $R^1$ substituent are optionally separated by the insertion into the chain of a group selected from O, NH, N(Me), CH=CH and C≡C, and when $R^1$ is a vinyl or ethynyl group, the $R^1$ substituent optionally bears at the terminal $CH_2$= or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$Q^2$-$X^2$— wherein $X^2$ is a direct bond or is NHCO or N(Me)CO and $Q^2$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, N-methylcarbamoyl, N,N-dimethylcarbamoyl and methoxy, and a pyrrolidin-2-yl, piperidin-3-yl, piperidin-4-yl, piperazin-1-yl or homopiperazin-1-yl group within a $R^1$ substituent is optionally N-substituted with allyl, 2-propynyl, methylsulphonyl, acetyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(o) m is 1 or 2, and each $R^1$ group, which may be the same or different, is selected from halogeno, trifluoromethyl, hydroxy, amino, carbamoyl, (1-6C)alkyl, (1-6C)alkoxy, (1-6C)alkylamino, di-[(1-6C)alkyl]amino, N-(1-6C)alkylcarbamoyl, N,N-di-[(1-6C)alkyl]carbamoyl, (2-6C)alkanoylamino and N-(1-6C)alkyl-(2-6C)alkanoylamino, or from a group of the formula:

$Q^1$-$X^1$— wherein $X^1$ is selected from O, N($R^4$), CON($R^4$), N($R^4$)CO and OC($R^4$)$_2$ wherein $R^4$ is hydrogen or (1-6C)alkyl, and $Q^1$ is aryl, aryl-(1-6C)alkyl, cycloalkyl-(1-6C)alkyl, heteroaryl, heteroaryl-(1-6C)alkyl, heterocyclyl or heterocyclyl-(1-6C)alkyl, or $X^1$ is a direct bond and $Q^1$ is aryl-(1-6C)alkyl, cycloalkyl-(1-6C)alkyl, heteroaryl-(1-6C)alkyl or heterocyclyl-(1-6C)alkyl, and wherein adjacent carbon atoms in any (2-6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1-6C)alkyl, or, when the inserted group is N($R^5$), $R^5$ may also be (2-6C)alkanoyl, and wherein any $CH_2$ or $CH_3$ group within a $R^1$ substituent optionally bears on each said $CH_2$ or $CH_3$ group one or more halogeno groups or a substituent selected from hydroxy, amino, (1-6C)alkoxy, (1-6C)alkylsulphonyl, (1-6C)alkylamino, di-[(1-6C)alkyl]amino, (2-6C)alkanoyloxy, (2-6C)alkanoylamino and N-(1-6C)alkyl-(2-6C)alkanoylamino, or from a group of the formula:

—$X^3$-$Q^3$ wherein $X^3$ is a direct bond or is selected from O, N($R^6$), CON($R_7$), N($R^7$)CO and C($R_7$)$_2$O, wherein $R^7$ is hydrogen or (1-6C)alkyl, and $Q^3$ is heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1-6C)alkyl, (2-8C)alkenyl, (2-8C)alkynyl, (1-6C)alkoxy, (1-6C)alkylsulphonyl, N-(1-6C)alkylcarbamoyl, N,N-di-[(1-6C)alkyl]carbamoyl and (2-6C)alkanoyl, or optionally bears 1 substituent selected from a group of the formula:

—$X^4$—$R^8$ wherein $X^4$ is a direct bond or is selected from O and N($R^9$), wherein $R^9$ is hydrogen or (1-6C)alkyl, and $R^8$ is hydroxy(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, and from a group of the formula:

—$X^5$-$Q^4$ wherein $X^5$ is a direct bond or is selected from O, N($R^{10}$) and Co, wherein $R^{10}$ is hydrogen or (1-6C)alkyl, and $Q^4$ is heterocyclyl or heterocyclyl-(1-6C)alkyl which optionally bears 1 or 2 substituents, which may be the same or different, selected from halogeno, (1-6C)alkyl and (1-6C)alkoxy, and wherein any heterocyclyl group within a substituent on R$^1$ optionally bears 1 or 2 oxo substituents;

(p) m is 1 or 2, and each R$^1$ group, which may be the same or different, is selected from fluoro, chloro, trifluoromethyl, hydroxy, amino, carbamoyl, methyl, ethyl, propyl, butyl, methoxy, ethoxy, propoxy, isopropoxy, butoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$Q^1$-$X^1$— wherein X$^1$ is selected from O, NH, CONH, NHCO and OCH$_2$ and Q$^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidinyl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, or wherein X$^1$ is a direct bond and Q$^1$ is benzyl, cyclopropylmethyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4pyridylmethyl, 2-(2-, 3- or 4-pyridyl)ethyl, 3-(2-, 3- or 4-pyridyl)propyl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a R$^1$ substituent are optionally separated by the insertion into the chain of a group selected from O, NH, N(Me), CONH, NHCO, CH=CH and C≡C, and wherein any CH$_2$ or CH$_3$ group within a R$^1$ substituent optionally bears on each said CH$_2$ or CH$_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido or from a group of the formula:

—X$^3$-Q$^3$ wherein X$^3$ is a direct bond or is selected from O, NH, CONH, NHCO and CH$_2$O and Q$^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on R$^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—X$^4$—R$^8$ wherein X$^4$ is a direct bond or is selected from O and NH and R$^8$ is 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—X$^5$-Q$^4$ wherein X$^5$ is a direct bond or is selected from O, NH and CO and Q$^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on R$^1$ optionally bears 1 or 2 oxo substituents;

(q) m is 1 and the R$^1$ group is located at the 5-, 6- or 7-position or m is 2 and each R$^1$ group, which may be the same or different, is located at the 5- and 7-positions or at the 6- and 7-positions and R$^1$ is selected from hydroxy, amino, methyl, ethyl, propyl, methoxy, ethoxy, propoxy, isopropoxy, butoxy, pentyloxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, 4-pyrrolidin-1-ylbutoxy, pyrrolidin-3- yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4piperazin-1-ylbutylamino, 2-homopiperazin-1-ylethylamino or 3-homopiperazin-1-ylpropylamino, and wherein adjacent carbon atoms in any (2-6C)alkylene chain within a $R^1$ substituent are optionally separated by the insertion into the chain of a group selected from O, NH, N(Me), CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, N-methylcarbamoyl, N,N-dimethylcarbamoyl and methoxy, and a pyrrolidin-2-yl, piperidin-3-yl, piperidin-4-yl, piperazin-1-yl or homopiperazin-1-yl group within a $R^1$ substituent is optionally N-substituted with allyl, 2-propynyl, methylsulphonyl, acetyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(r) n is 1 or 2 and the $R^3$ groups, which may be the same or different, are located at the 4-, 5- and/or 6-positions of the 2,3-methylenedioxyphenyl group and are selected from halogeno, trifluoromethyl, cyano, hydroxy, (1-6C)alkyl, (2-8C)alkenyl, (2-8C)alkynyl, (1-6C)alkoxy, (1-6C)alkylthio, (1-6C)alkylsulphinyl and (1-6C)alkylsulphonyl, or from a group of the formula:

—$X^6$—$R^{11}$ wherein $X^6$ is a direct bond and $R^{11}$ is hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

—$X^7$-$Q^5$ wherein $X^7$ is a direct bond and $Q^5$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy; and (s) n is 1 or 2 and the $R^3$ groups, which may be the same or different, are located at the 4-, 5- and/or 6-positions of the 2,3-methylenedioxyphenyl group and are selected from fluoro, chloro, bromo, iodo, trifluoromethyl, cyano, hydroxy, methyl, ethyl, vinyl, allyl, ethynyl, 1-propynyl, methoxy, methylthio, methylsulphinyl, methylsulphonyl, hydroxymethyl, 2-hydroxyethyl, methoxymethyl, 2-methoxyethyl, cyanomethyl, 2-cyanoethyl, aminomethyl, methylaminomethyl, dimethylaminomethyl, phenyl, benzyl, 5-isoxazolyl and morpholinomethyl.

Further particular novel compounds of the invention include, for example, quinoline derivatives of the Formula I, or pharmaceutically-acceptable salts thereof, wherein, unless otherwise stated, each of Z, m, $R^1$, n and $R^3$ has any of the meanings defined hereinbefore provided that:—

(A) $R^1$ substituents may only be located at the 5-, 6- and/or 7-positions on the quinoline ring i.e. the 2- and 8-positions remain unsubstituted; or (B) $R^1$ substituents may only be located at the 6- and/or 7-positions on the quinoline ring i.e. the 2-, 5- and 8-positions remain unsubstituted.

A particular compound of the invention is a quinoline derivative of the Formula I wherein:

Z is O or NH;

m is 1 and the $R^1$ group is located at the 5-, 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, methoxy, ethoxy, propoxy, isopropoxy, butoxy, pent-4-ynyloxy, hex-5-ynyloxy, methylamino, ethylamino, dimethylamino, diethylamino, acetamido, propionamido, 2-imidazol-1-ylethoxy, 2-(1,2,4-triazol-1-yl)ethoxy, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2-6C)alkylene chain within a R¹ substituent are optionally separated by the insertion into the chain of a group selected from O, NH, N(Me), CH=CH and C≡C, and wherein any CH₂ or CH₃ group within a R¹ substituent optionally bears on each said CH₂ or CH₃ group one or more chloro groups or a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on R¹ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a R¹ substituent is optionally N-substituted with allyl, methylsulphonyl, acetyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3piperazin-1-ylpropyl, the last 8 of which substituents each optionally bears 1 or 2 substituents, which may be the same or different, selected from fluoro, chloro, methyl and methoxy, and wherein any heterocyclyl group within a substituent on R¹ optionally bears 1 or 2 oxo substituents; and n is 0 or 1 and the R³ group, if present, is located at the 5- or 6-position of the 2,3-methylenedioxyphenyl group and is selected from fluoro, chloro, bromo, trifluoromethyl, cyano, hydroxy, methyl, ethyl, vinyl, allyl, ethynyl, methoxy and ethoxy;

or a pharmaceutically-acceptable acid-addition salt thereof.

A further particular compound of the invention is a quinoline derivative of the Formula I wherein:

Z is O or NH;

m is 2 and the first R¹ group is located at the 6-position and is selected from hydroxy, methoxy, ethoxy and propoxy, and the second R¹ group is located at the 7-position and is selected from 2-hydroxyethoxy, 3-hydroxypropoxy, 4-hydroxybutoxy, 2-methoxyethoxy, 3-methoxypropoxy, 4-methoxybutoxy, 2-(2-hydroxyethoxy)ethoxy, 2-(2-methoxyethoxy)ethoxy, 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-(N-isopropyl-N-methylamino)butoxy, 2-(N-alkylamino)ethoxy, 3-(N-alkylamino)propoxy, 2-(N-allyl-N-methylamino)ethoxy, 3-(N-allyl-N-methylamino)propoxy, 2-(N-prop-2-ynylamino)ethoxy, 3-(N-prop-2-ynylamino)propoxy, 2-(N-methyl-N-prop-2-ynylamino)ethoxy, 3-(N-methyl-N-prop-2-ynylamino)propoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-N-methylpiperidin-4-yl)propoxy, 2-(4-methylpiperazin-1-yl)ethoxy, 3-(4-methylpiperazin-1-yl)propoxy, 4-(4-methylpiperazin-1-yl)butoxy, 2-(4-allylpiperazin-1-yl)ethoxy, 3-(4allylpiperazin-1-yl)propoxy, 4-(4allylpiperazin-17yl)butoxy, 2-(4-methylsulphonylpiperazin-1-yl)ethoxy, 3-(4methylsulphonylpiperazin-1-yl)propoxy, 4-(4-methylsulphonylpiperazin-1-yl)butoxy, 2-(4-acetylpiperazin-1-yl)ethoxy, 3-(4acetylpiperazin-1-yl)propoxy, 4-(4-acetylpiperazin-1-yl)butoxy, 2-(4-cyanomethylpiperazin-1-yl)ethoxy, 3-(4cyanomethylpiperazin-1-yl)propoxy, 4-(4-cyanomethylpiperazin-1-yl)butoxy, 2-[2-(4-methylpiperazin-1-yl)ethoxy]ethoxy, 2-chloroethoxy, 3chloropropoxy, 2-methylsulphonylethoxy and 3-methylsulphonylpropoxy, and wherein any CH₂ group within the second R¹ group that is attached to two carbon atoms optionally bears a hydroxy group or acetoxy group on said CH₂ group, and wherein any heterocyclyl group within the second R¹ group optionally bears 1 or 2 substituents selected from fluoro, hydroxy, methyl and oxo; and n is 0 or n is 1 and the R³ group, if present, is located at the 5- or 6-position of the 2,3-methylenedioxyphenyl group and is selected from fluoro, chloro, bromo, trifluoromethyl, cyano, methyl, ethyl, ethynyl, methoxy and ethoxy;

or a pharmaceutically-acceptable acid-addition salt thereof.

A further particular compound of the invention is a quinoline derivative of the Formula I wherein:

Z is O or NH;

m is 2 and the first R¹ group is a 6-methoxy group and the second R¹ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-4-isopropyl-N-methylamino)butoxy, 2-(N-isobutyl-N-methylamino)ethoxy, 3-(N-isobutyl-N-methylamino)propoxy, 4-(N-isobutyl-N-methylamino)butoxy, 2-(N-allyl-N-methylamino)ethoxy, 3-(N-allyl-N-methylamino)propoxy, 2-(N-prop-2-ynylamino)ethoxy, 3-(N-prop-2-ynylamino)propoxy, 2-(N-methyl-N-prop-2-ynylamino)ethoxy, 3-(N-methyl-N-prop-2-ynylamino)propoxy, 2-pyrrolidin-1-ylethoxy, 3-pyrrolidin-1-ylpropoxy, 4-pyrrolidin-1-ylbutoxy, pyrrolidin-3-yloxy, methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, N-cyanomethylpiperidin-3-ylmethoxy, piperidin-4-ylmethoxy, N-methylpiperidin-4-ylmethoxy, N-cyanomethylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy 3-(N-methylpiperidin-4-yl)propoxy, 2-homopiperidin-1-ylethoxy, 3-homopiperidin-1-ylpropoxy, 4-homopiperidin-1-ylbutoxy, 2-piperazin-1-ylethoxy, 2-(4-methylpiperazin-1-yl)ethoxy, 3-piperazin-1-ylpropoxy, 3-(4-methylpiperazin-1-yl)propoxy, 4-piperazin-1-ylbutoxy, 4-(4-methylpiperazin-1-yl)butoxy, 2-(4-allylpiperazin-1-yl)ethoxy, 3-(4-allylpiperazin-1-yl)propoxy, 4-(4-allylpiperazin-1-yl)butoxy, 2-(4-methylsulphonylpiperazin-1-yl)ethoxy, 3-(4-methylsulphonylpiperazin-1-yl)propoxy, 4-(4-methylsulphonylpiperazin-1-yl)butoxy, 2-(4-acetylpiperazin-1-yl)ethoxy, 3-(4-acetylpiperazin-1-yl)propoxy, 4-(4-acetylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-(2-piperazin-1-ylethoxy)ethoxy, 2-[2-(4-methylpiperazin-1-yl)ethoxy]ethoxy, 2-chloroethoxy, 3-chloropropoxy, 2-methylsulphonylethoxy, 3-methylsulphonylpropoxy, 2-tetrahydropyran-4-ylethoxy, 3-tetrahydropyran-4-ylpropoxy, 2-pyrrol-1-ylethoxy, 3-pyrrol-1-ylpropoxy, 2-(2-pyridyloxy)ethoxy, 3-(2-pyridyloxy)propoxy, 2-(3-pyridyloxy)ethoxy, 3-(3-pyridyloxy)propoxy, 2-(4-pyridyloxy)ethoxy, 3-(4-pyridyloxy)propoxy, 2-pyridylmethoxy, 3-pyridylmethoxy and 4-pyridylmethoxy, and wherein any $CH_2$ group within the second $R^1$ group that is attached to two carbon atoms optionally bears a hydroxy group on said $CH_2$ group, and wherein any heteroaryl group within the second $R^1$ group optionally bears 1 or 2 substituents selected, from chloro, cyano, hydroxy and methyl, and any heterocyclyl group within the second $R^1$ group optionally bears 1 or 2 substituents selected from fluoro, hydroxy, methyl and oxo; and n is 0 or n is 1 and the $R^3$ group, if present, is located at the 6-position of the 2,3-methylenedioxyphenyl group and is selected from fluoro, chloro and bromo;

or a pharmaceutically-acceptable acid-addition salt thereof.

A further particular compound of the invention is a quinoline derivative of the Formula I wherein:

Z is NH;

m is 2 and the first $R^1$ group is a 6-methoxy group and the second $R^1$ group is located at the 7-position and is selected from 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,1 thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 3-chloropropoxy, 2-methylsulphonylethoxy, 3-methylsulphonylpropoxy, 2-(4-pyridyloxy)ethoxy, 3-pyridylmethoxy and 2-cyanopyrid-4-ylmethoxy; and n is 0 or n is 1 and the $R^3$ group, if present, is located at the 6-position of the 2,3-methylenedioxyphenyl group and is selected from chloro and bromo;

or a pharmaceutically-acceptable acid-addition salt thereof.

A further particular compound of the invention is a quinoline derivative of the Formula I wherein:

Z is NH or O;

m is 2 and the first $R^1$ group is a 6-methoxy group and the second $R^1$ group is located at the 7-position and is selected from hydroxy, methoxy, 2-bromoethoxy, 2-hydroxyethoxy, 2-methoxyethoxy, 2-hydroxy-3-methoxypropoxy, 2-(2-hydroxyethoxy)ethoxy, 2-prop-2-ynylaminoethoxy, 2-(N-methyl-N-prop-2-ynylamino)ethoxy, 3-(N-methyl-N-prop-2-ynylamino)propoxy, 3-(2,5-dimethylpyrrol-1-yl)propoxy; 3-pyrrolidin-1-ylpropoxy, 3-(3-fluoropyrrolidin-1-yl)propoxy, 3-(3,3-difluoropyrrolidin-1-yl)propoxy, 3-(2,5-dimethyl-3-pyrrolin-1-yl)propoxy, 3-morpholinopropoxy, 2-hydroxy-3-morpholinopropoxy, 2-fluoro-3-morpholinopropoxy, 3-(1,1-dioxotetrahydro-4H-1,4-thiazin-4-yl)propoxy, 3-piperidinopropoxy, 3-(4hydroxypiperidin-1-yl)propoxy, 3-(4-fluoropiperidin-1-yl)propoxy, 3-(4,4-difluoropiperidin-1-yl)propoxy, 3-(1,2,3,6-tetrahydropyridin-1-yl)propoxy, 2-fluoro-3-(1,2,3,6-tetrahydropyridin-1-yl)propoxy, 4-(1,2,3,6-tetrahydropyridin-1-yl)butoxy, 3-piperazin-1-ylpropoxy, 2-(4-methylpiperazin-1-yl)ethoxy, 3-(4methylpiperazin-1-yl)propoxy, 2-fluoro-3-(4-methylpiperazin-1-yl)propoxy, 4-(4methylpiperazin-1-yl)butoxy, 2-(4-allylpiperazin-1-yl)ethoxy, 3-(4-allylpiperazin-1-yl)propoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 3-(4-acetylpiperazin-1-yl)-2-hydroxypropoxy, 3-(4-cyanomethylpiperazin-1-yl)propoxy, 3-chloropropoxy and 3-bromopropoxy; and n is 0, 1 or 2 and each $R^3$ group, if present, is selected from fluoro, chloro, bromo, iodo, cyano, methyl, ethyl, ethynyl, methylthio, methylsulphonyl, hydroxymethyl, methoxymethyl, 2-methoxyethyl, 2-cyanoethyl, dimethylaminomethyl, phenyl, benzyl, 5-oxazolyl and morpholinomethyl;

or a pharmaceutically-acceptable acid-addition salt thereof.

A particular compound of the invention is a quinoline derivative of the Formula I wherein:

Z is O or NH;

m is 1 and the $R^1$ group is located at the 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, methoxy, ethoxy, propoxy, isopropoxy, butoxy, methylamino, ethylamino, dimethylamino, diethylamino, acetamido, propionamido, 2-imidazol-1-ylethoxy, 2-(1,2,4-triazol-1-yl)ethoxy, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin- 2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1ylpropoxy, 2-piperazin-1-ylethoxy, 3-piperazin-1-ylpropoxy, 4piperazin-1-ylbutoxy, 2-homopiperazin-1-ylethoxy and 3-homopiperazin-1-ylpropoxy, and wherein adjacent carbon atoms in any (2-6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group one or more chloro groups or a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents; and n is 0 or 1 and the $R^3$ group, if present, is located at the 5- or 6-position of the 2,3-methylenedioxyphenyl group and is selected from fluoro, chloro, trifluoromethyl, cyano, hydroxy, methyl, ethyl, vinyl, allyl, ethynyl, methoxy and ethoxy;

or a pharmaceutically-acceptable acid-addition salt thereof.

A further particular compound of the invention is a quinoline derivative of the Formula I wherein:

Z is or NH;

m is 2 and the first $R^1$ group is located at the 6-position and is selected from hydroxy, methoxy, ethoxy and propoxy, and the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2diisopropylaminoethoxy, 3-diisopropylaminopropoxy, 4-diisopropylaminobutoxy, 2-N-isopropyl-N-methylamino)ethoxy, 3-(N-isopropyl-N-methylamino)propoxy, 4-(N-isopropyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H 1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-N-methylpiperidin-4-yl)ethoxy, 3-piperidin-4-ylpropoxy, 3-(N-methylpiperidin-4-yl)propoxy, 2-(4methylpiperazin-1-yl)ethoxy, 3-(4-methylpiperazin-1-yl)propoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-[2-(4-methylpiperazin-1-yl)ethoxy]ethoxy, 2-chloroethoxy, 3-chloropropoxy, 2-methylsulphonylethoxy and 3-methylsulphonylpropoxy, and wherein any $CH_2$ group within the second $R^1$ group that is attached to two carbon atoms optionally bears a hydroxy group or acetoxy group on said $CH_2$ group, and wherein any heterocyclyl group within the second $R^1$ group optionally bears 1 or 2 oxo substituents; and n is 0 or n is 1 and the $R^3$ group is located at the 5- or 6-position of the 2,3-methylenedioxyphenyl group and is selected from fluoro, chloro, trifluoromethyl, cyano, methyl, ethyl, ethynyl, methoxy and ethoxy;

or a pharmaceutically-acceptable acid-addition salt thereof.

A further particular compound of the invention is a quinoline derivative of the Formula I wherein:

Z is O or NH;

m is 2 and the first $R^1$ group is a 6-methoxy group and the second $R^1$ group is located at the 7-position and is selected from 2-dimethylaminoethoxy, 3-dimethylaminopropoxy, 4-dimethylaminobutoxy, 2-diethylaminoethoxy, 3-diethylaminopropoxy, 4-diethylaminobutoxy, 2-diisopropylaminoethoxy, 3-diisopropylaminopropoxy, 4-diisopropylaminobutoxy, 2-(N-isopropyl-N-methylamino)ethoxy, 3-(N-isopropyl-N-methylamino)propoxy, 4-(N-isopropyl-N-methylamino)butoxy, 2-(N-isobutyl-N-methylamino)ethoxy, 3-(N-isobutyl-N-methylamino)propoxy, 4-(N-isobutyl-N-methylamino)butoxy, 2-(N-allyl-N-methylamino)ethoxy, 3-(N-allyl-N-methylamino)propoxy, 4-(N-allyl-N-methylamino)butoxy, 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4morpholinobutoxy, 2-(1,1-dioxotetrahydro-4H-1,4-thiazin-4-yl)ethoxy, 3-(1,1dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, N-cyanomethylpiperidin-3-ylmethoxy, piperidin-4-ylmethoxy, N-methylpiperidin-4-ylmethoxy, N-cyanomethylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)

propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-homopiperidin-1-ylethoxy, 3-homopiperidin-1-ylpropoxy, 4homopiperidin-1-ylbutoxy, 2-piperazin-1-ylethoxy, 2-(4-methylpiperazin-1-yl)ethoxy, 3-piperazin-1-ylpropoxy, 3-(4-methylpiperazin-1-yl)propoxy, 4-piperazin-1-ylbutoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-(2-piperazin-1-ylethoxy)ethoxy, 2-[2-(4-methylpiperazin-1-yl)ethoxy]ethoxy, 2-chloroethoxy, 3-chloropropoxy, 2-methylsulphonylethoxy, 3-methylsulphonylpropoxy, 2-tetrahydropyran-4-ylethoxy, 3-tetrahydropyran-4-ylpropoxy, 2-pyrrol-1-ylethoxy, 3-pyrrol-1-ylpropoxy, 2-(2-pyridyloxy)ethoxy, 3-(2-pyridyloxy)propoxy, 2-(3-pyridyloxy)ethoxy, 3-(3-pyridyloxy)propoxy, 2-(4-pyridyloxy)ethoxy, 3-(4-pyridyloxy)propoxy, 2-pyridylmethoxy, 3-pyridylmethoxy and 4-pyridylmethoxy, and wherein any $CH_2$ group within the second $R^1$ group that is attached to two carbon atoms optionally bears a hydroxy group on said $CH_2$ group, and wherein any heteroaryl group within the second $R^1$ group optionally bears 1 or 2 substituents selected from chloro, cyano, hydroxy and methyl, and any heterocyclyl group within the second $R^1$ group optionally bears 1 or 2 substituents selected from hydroxy, methyl and oxo; and n is 0 or n is 1 and the $R^3$ group is located at the 6-position of the 2,3-methylenedioxyphenyl group and is selected from chloro and bromo;

or a pharmaceutically-acceptable acid-addition salt thereof.

A further particular compound of the invention is a quinoline derivative of the Formula I wherein:
Z is NH;
m is 2 and the first $R^1$ group is a 6-methoxy group and the second $R^1$ group is located at the 7-position and is selected from 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-[4-methylpiperazin-1-yl)propoxy, 2-(4-cyanomethylpiperazin-1-yl)ethoxy, 3-(4-cyanomethylpiperazin-1-yl)propoxy, 2-[2-(4-methylpiperazin-1-yl]ethoxy]ethoxy, 3-chloropropoxy, 2-methylsulphonylethoxy, 3-methylsulphonylpropoxy, 2-(4pyridyloxy)ethoxy, 3-pyridylmethoxy and 2-cyanopyrid-4-ylmethoxy; and n is 0 or n is 1 and the $R^3$ group is located at the 6-position of the 2,3-methylenedioxyphenyl group and is selected from chloro and bromo;

or a pharmaceutically-acceptable acid-addition salt thereof.

A further particular compound of the invention is a quinoline derivative of the Formula I wherein:
Z is NH;
m is 2 and the first $R^1$ group is a 6-methoxy group and the second $R^1$ group is located at the 7-position and is selected from 3-(4-methylpiperazin-1-yl)propoxy or 3-chloropropoxy,
n is 1 and the $R^3$ group is a chloro or bromo group located at the 6-position of the 2,3-methylenedioxyphenyl group;

or a pharmaceutically-acceptable acid-addition salt thereof.

A particular compound of the invention is, for example, a quinoline derivative of the Formula I selected from:—
4-(6-chloro-2,3-methylenedioxyanilino)-3-cyano-6-methoxy-7-[3-(4-methylpiperazin-1-yl)propoxy]quinoline and
4-(6-chloro-2,3-methylenedioxyanilino)-7-(3-chloropropoxy)-3-cyano-6-methoxyquinoline, or a pharmaceutically-acceptable acid-addition salt thereof.

Further particular compounds of the invention include, for example, the quinoline derivatives of the Formula I described hereinafter in Examples 4-(1) to 4-(9), 4-(11), 4-(12), 4-(14), 4-(27), 10(1) to 10(3), 10(16), 14 and 15.

A further particular compound of the invention is a quinoline derivative of the Formula I wherein:
m is 2 and the first $R^1$ group is located at the 5-position and is selected from tetrahydrofuran-3-yloxy, tetrahydropyran-4-yloxy, tetrahydrothien-3-yloxy, 1,1-dioxotetrahydrothien-3-yloxy, tetrahydrothiopyran-4-yloxy, 1,1-dioxotetrahydrothiopyran-4-yloxy, N-methylazetidin-3-yloxy, N-ethylazetidin-3-yloxy, N-isopropylazetidin-3-yloxy, pyrrolidin-3-yloxy, N-methylpyrrolidin-3-yloxy, pyrrolidin-2-ylmethoxy, 3-piperidinyloxy, N-methylpiperidin-3-yloxy, 4-piperidinyloxy, N-methylpiperidin-4-yloxy, N-allylpiperidin-4-yloxy, N-prop-2-ynylpiperidin-4-yloxy, N-acetylpiperidin-4-yloxy, N-methylsulphonylpiperidin-4-yloxy, N-(2-methoxyethyl)piperidin-4-yloxy, piperidin-3-ylmethoxy, N-methylpiperidin-3-ylmethoxy, piperidin-4-ylmethoxy, N-methylpiperidin-4-ylmethoxy, cyclobutyloxy, cyclopentyloxy and cyclohexyloxy, and the second $R^1$ is located at the 7-position and is selected from hydroxy, methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-4-ylethoxy, 2-(N-methylpiperidin-4-yl)ethoxy, 2-homopiperidin-1-ylethoxy, 3-homopiperidin-1-ylpropoxy, 2-piperazin-1-ylethoxy, 3-piperazin-1-ylpropoxy, 2-(4-methylpiperazin-1-yl)ethoxy, 3-(4methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 2-tetrahydropyran-4-ylethoxy, 2-hydroxyethoxy, 3-hydroxypropoxy, 2-methoxyethoxy, 3-methoxypropoxy, 2-methylsulphonylethoxy, 3-methylsulphonylpropoxy, 2-(2-methoxyethoxy)ethoxy, piperidin-4-ylmethoxy, N-methylpiperidin-4-ylmethoxy, 2-(4-pyridyloxy)ethoxy, 2-pyridylmethoxy, 3-pyridylmethoxy, 4-pyridylmethoxy and 3-cyanopyrid-4-ylmethoxy;

and wherein any $CH_2$ group within a $R^1$ substituent that is attached to two carbon atoms optionally bears a hydroxy group on said CH₂ group, and wherein any heterocyclyl group within a R¹ substituent optionally bears 1 or 2 oxo substituents, and wherein any CH₂ group within a R¹ substituent that is attached to two carbon atoms optionally bears a hydroxy group on said CH₂ group;

n is 0 or n is 1 and the R³ group, if present, is located at the 5- or 6-position of the 2,3-methylenedioxyphenyl group and is selected from fluoro, chloro, bromo, trifluoromethyl, cyano, methyl, ethyl, ethynyl, methoxy and ethoxy;

or a pharmaceutically-acceptable acid-addition salt thereof.

A further particular compound of the invention is a quinoline derivative of the Formula I wherein:

m is 2 and the first R¹ group is located at the 5-position and is selected from tetrahydropyran-4-yloxy, N-methylpyrrolidin-3-yloxy, 4-piperidinyloxy, N-methylpiperidin-4-yloxy, piperidin-4-ylmethoxy and N-methylpiperidin-4-ylmethoxy, and the second R¹ is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy and 3-methylsulphonylpropoxy; n is 0 or n is 1 and the R³ group, if present, is located at the 6-position of the 2,3-methylenedioxyphenyl group and is selected from chloro and bromo;

or a pharmaceutically-acceptable acid-addition salt thereof.

A further particular compound of the invention is a quinoline derivative of the Formula I wherein:

m is 2 and the first R¹ group is located at the 5-position and is selected from tetrahydropyran-4-yloxy, 4-piperidinyloxy, N-methylpiperidin-4-yloxy, piperidin-4-ylmethoxy and N-methylpiperidin-4-ylmethoxy, and the second R¹ is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 3-(4-hydroxypiperidin-1-yl)propoxy, 2-piperidin-4-ylethoxy, 2-(N-methylpiperidin-4-yl)ethoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4methylpiperazin-1-yl)propoxy, 3-(4-cyanomethylpiperazin-1-yl)propoxy, 3-methylsulphonylpropoxy, piperidin-4-ylmethoxy and N-methylpiperidin-4-ylmethoxy; n is 0 or n is 1 and the R³ group, if present, is located at the 6-position of the 2,3-methylenedioxyphenyl group and is selected from chloro and bromo;

or a pharmaceutically-acceptable acid-addition salt thereof.

A further particular compound of the invention is, for example, a quinoline derivative of the Formula I selected from:—

4-(6chloro-2,3-methylenedioxyamino)-3-cyano-7-methoxy-5-(N-methylpiperidin-4-yloxy)quinoline, 4-(6-chloro-2,3-methylenedioxyanilino)-3-cyano-7-(2-pyrrolidin-1-ylethoxy)-5-tetrahydropyran-4-yloxyquinoline, 4-(6-chloro-2,3-methylenedioxyanilino)-3-cyano-7-(3-pyrrolidin-1-ylpropoxy)-5-tetrahydropyran-4-yloxyquinoline, 4-(6-chloro-2,3-methylenedioxyamino)-3-cyano-7-[3-(4-methylpiperazin-1-yl)propoxy]-5-tetrahydropyran-4-yloxyquinoline, 4-(6-chloro-2,3-methylenedioxyamino)-3-cyano-7-[2-(4-methylpiperazin-1-yl)ethoxy]-5-tetrahydropyran-4-yloxyquinoline, 4-(6chloro-2,3-methylenedioxyamino)-3-cyano-7-(2-piperidinoethoxy)-5-tetrahydropyran-4-yloxyquinoline and 4-(6-chloro-2,3-methylenedioxyamino)-3-cyano-7-(N-methylpiperidin-4-ylmethoxy)-5-tetrahydropyran-4-yloxyquinoline, or a pharmaceutically-acceptable acid-addition salt thereof.

A quinoline derivative of the Formula I, or a pharmaceutically-acceptable salt thereof, may be prepared by any process known to be applicable to the preparation of chemically-related compounds. Such processes, when used to prepare a quinoline derivative of the Formula I are provided as a further feature of the invention and are illustrated by the following representative process variants in which, unless otherwise stated, m, R¹, Z, n and R³ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) For the production of those compounds of the Formula I wherein Z is an O, S or N(R²) group, the reaction of a quinoline of the Formula II

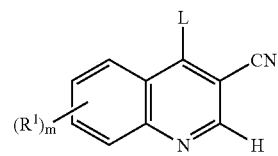

II wherein L is a displaceable group and m and R¹ have any of the meanings defined hereinbefore except that any functional group is protected if necessary, with a compound of the Formula III

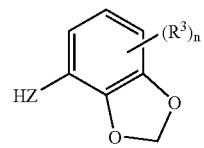

III wherein Z is O, S, or N(R²) and h, R³ and R² have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 250° C., preferably in the range 0 to 120° C.

Typically, the quinoline of the Formula II may be reacted with a compound of the Formula III in the presence of an aprotic solvent such as N,N-dimethylformamide, conveniently in the presence of a base, for example potassium carbonate or sodium hexamethyldisilazane, and at a temperature in the range, for example, 0 to 150° C., preferably in the range, for example, 0 to 70° C.

The quinoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

Quinoline starting materials of the Formula II may be obtained by conventional procedures such as those disclosed in International Patent Applications WO 98/43960 and WO 00/68201. For example, a 1,4-dihydroquinolinone of Formula IV

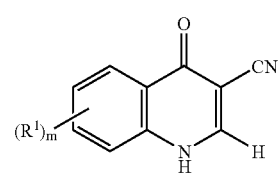

IV wherein m and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinoline so obtained may be converted, if required, into a 4-pentafluorophenoxyquinoline by reaction with pentafluorophenol in the presence of a suitable base such as potassium carbonate and in the presence of a suitable solvent such as N,N-dimethylformamide.

2,3-Methylenedioxyanilino starting materials (Formula III, for example when Z is NH) and 2,3-methylenedioxyphenol starting materials (Formula III when Z is O) may be obtained by conventional procedures as illustrated in the Examples. Corresponding 2,3-methylenedioxythiophenol starting materials (Formula II, when Z is S) may be obtained by conventional procedures.

(b) For the production of those compounds of the Formula I wherein at least one $R^1$ group is a group of the formula

wherein $Q^1$ is an aryl-(1-6C)alkyl, (3-7C)cycloalkyl-(1-6C)alkyl, (3-7C)cycloalkenyl-(1-6C)alkyl, heteroaryl-(1-6C)alkyl or heterocyclyl-(1-6C)alkyl group or an optionally substituted alkyl group and $X^1$ is an oxygen atom, the coupling, conveniently in the presence of a suitable dehydrating agent, of a quinoline of the Formula V

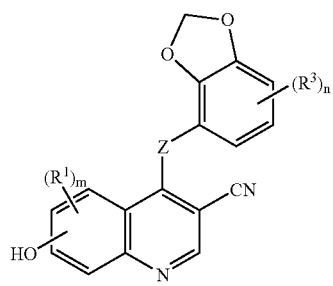

V wherein m, $R^1$, Z, n and $R^3$ have any of the meanings defined hereinbefore except that any functional group is protected if necessary, with an appropriate alcohol wherein any functional group is protected if necessary whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(c) For the production of those compounds of the Formula I wherein $R^1$ is an amino-substituted (1-6C)alkoxy group (such as 2-homopiperidin-1-ylethoxy or 3-dimethylaminopropoxy), the reaction of a compound of the Formula I wherein $R^1$ is a halogeno-substituted (1-6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(d) For the production of those compounds of the Formula I wherein $R^1$ is a hydroxy group, the cleavage of a quinoline derivative of the Formula I wherein $R^1$ is a (1-6C)alkoxy or arylmethoxy group.

The cleavage reaction may conveniently be carried out by any of the many procedures known for such a transformation. The cleavage reaction of a compound of the Formula I wherein $R^1$ is a (1-6C)alkoxy group may be carried out, for example, by treatment of the quinoline derivative with an alkali metal (1-6C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinoline derivative with a boron or aluminium trihalide such as boron tribromide. The cleavage reaction of a compound of the Formula I wherein $R^1$ is a arylmethoxy group may be carried out, for example, by hydrogenation of the quinoline derivative in the presence of a suitable metallic catalyst such as palladium or by reaction with an organic or inorganic acid, for example trifluoroacetic acid. Such reactions are preferably carried out in the presence of a suitable inert solvent or diluent as defined hereinbefore and at a temperature in the range, for example, 10 to 150° C., preferably at or near ambient temperature.

(e) For the production of those compounds of the Formula I wherein an $R^1$ group contains a primary or secondary amino group, the cleavage of the corresponding compound of the Formula I wherein the $R^1$ group contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis, for example in the presence of trifluoroacetic acid.

(f) For the production of those compounds of the Formula I wherein an $R^1$ group contains a (1-6C)alkoxy or substituted (1-6C)alkoxy group or a (1-6C)alkylamino or substituted (1-6C)alkylamino group, the alkylation, conveniently in the presence of a suitable base as defined hereinbefore, of a quinoline derivative of the Formula I wherein the $R^1$ group contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $R^1$ contains a (1-6C)alkylamino or substituted (1-6C)alkylamino group, a reductive amination reaction may be employed. For example, for the production of those compounds of the Formula I wherein $R^1$ contains a N-methyl group, the corresponding compound containing a N—H group may be reacted with formaldehyde in the presence of a suitable reducing agent. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(g) For the production of those compounds of the Formula I wherein $R^1$ is an amino-hydroxy-disubstituted (1-6C) alkoxy group (such as 2-hydroxy-3-pyrrolidin-1-ylpropoxy or 3-[N-allyl-N-methylamino]-2-hydroxypropoxy), the reaction of a compound of the Formula I wherein the $R^1$ group contains an epoxy-substituted (1-6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(h) For the production of those compounds of the Formula I wherein an $R^1$ group contains a hydroxy group, the cleavage of the corresponding compound of the Formula I wherein the $R^1$ group contains a protected hydroxy group.

Suitable protecting groups for a hydroxy group are, for example, any of the protecting groups disclosed hereinbefore. Suitable methods for the cleavage of such hydroxy protecting groups are also disclosed hereinbefore. In particular, a suitable protecting group is a lower alkanoyl group such as an acetyl group which may be cleaved under conventional reaction conditions such as under base-catalysed conditions, for example in the presence of ammonia.

(i) For the production of those compounds of the Formula I wherein Z is a SO or $SO_2$ group, wherein an $R^1$ or $R^3$ substituent is a (1-6C)alkylsulphinyl or (1-6C)alkylsulphonyl group or wherein an $R^1$ or $R^3$ substituent contains a SO or $SO_2$ group, the oxidation of a compound of Formula I wherein Z is a S group or wherein an $R^1$ or $R^3$ substituent is a (1-6C)alkylthio group or wherein an $R^1$ or $R^3$ substituent contains a S group as appropriate.

Conventional oxidation reagents and reaction conditions for such partial or complete oxidation of a sulphur atom are well known to the organic chemist.

(j) For the production of those compounds of the Formula I wherein an $R^1$ group contains a (1-6C)alkoxy or substituted (1-6C)alkoxy group of a (1-6C)alkylamino or substituted (1-6C)alkylamino group, the reaction, conveniently in the presence of a suitable base as defined hereinbefore, of a quinoline derivative of the Formula VI

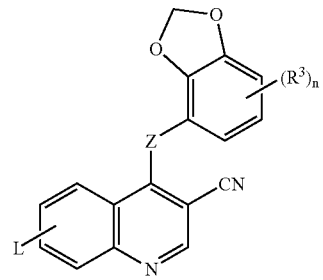

wherein L is a displaceable group as defined hereinbefore and Z, n and $R^3$ have any of the meanings defined hereinbefore except that any functional group is protected if necessary, with an alcohol or amine as appropriate.

k) The conversion of a compound of the Formula I wherein an $R^1$ or $R^3$ substituent is a halogeno group into a further compound of the Formula I wherein the $R^1$ or $R^3$ substituent is, for example, a cyano, ethynyl or phenyl group.

For example, a compound of the Formula I wherein an $R^1$ or $R^3$ substituent is a halogeno group may be reacted with a metal cyanide to form a compound of the Formula I wherein an $R^1$ or $R^3$ substituent is a cyano group. Conveniently, the reaction may be carried out in the presence of a suitable catalyst. A suitable metal cyanide is, for example, a heavy metal cyanide such as zinc cyanide. A suitable catalyst is, for example, an organometallic reagent, for example an organoiron compound such as diphenylphosphinoferrocene. The conversion reaction is conveniently carried out in the presence of a suitable inert diluent or carrier as defined hereinbefore and at a temperature in the range 10 to 150° C., preferably at or near 100° C.

For example, a compound of the Formula I wherein an $R^1$ or $R^3$ substituent is a halogeno group may be reacted with a (2-6C)alkyne to form a compound of the Formula I wherein an $R^1$ or $R^3$ substituent is a (2-6C)alkynyl group such as an ethynyl group. The reaction may conveniently be carried out in the presence of a suitable base as defined hereinbefore and in the presence of a suitable catalyst. For this conversion, a suitable catalyst is, for example, an organometallic reagent, for example an organopalladium compound such as tetrakis (triphenylphosphine)palladium(0). The conversion reaction is conveniently carried out in the presence of a suitable inert diluent or carrier as defined hereinbefore and at a temperature in the range 10 to 150° C., preferably at or near 60° C.

For example, a compound of the Formula I wherein an $R^1$ or $R^3$ substituent is a halogeno group may be reacted with an arylboron reagent to form a compound of the Formula I wherein an $R^1$ or $R^3$ substituent is an aryl group such as a phenyl group. A suitable arylboron reagent is, for example, an arylboronic acid. The reaction may conveniently be carried out in the presence of a suitable catalyst, for example, an organopalladium compound such as tetrakis(triphenylphosphine)palladium(0). The conversion reaction is conveniently carried out in the presence of a suitable inert diluent or carrier as defined hereinbefore and at a temperature in the range 10 to 150° C., preferably at or near 80° C.

When a pharmaceutically-acceptable salt of a quinoline derivative of the Formula I is required, for example an acid-addition salt, it may be obtained by, for example, reaction of said quinoline derivative with a suitable acid using a conventional procedure.

BIOLOGICAL ASSAYS

The following assays can be used to measure the effects of the compounds of the present invention as c-Src tyrosine kinase inhibitors, as inhibitors in vitro of the proliferation of c-Src transfected fibroblast cells, as inhibitors in vitro of the migration of A549 human lung tumour cells and as inhibitors in vivo of the growth in nude mice of xenografts of A549 tissue.

(a) In Vitro Enzyme Assay

The ability of test compounds to inhibit the phosphorylation of a tyrosine containing polypeptide substrate by the enzyme c-Src kinase was assessed using a conventional Elisa assay.

A substrate solution [100 µl of a 20 µg/ml solution of the polyamino acid Poly(Glu, Tyr) 4:1 (Sigma Catalogue No. P0275) in phosphate buffered saline (PBS) containing 0.2 mg/ml of sodium azide] was added to each well of a number of Nunc 96-well immunoplates (Catalogue No. 439454) and the plates were sealed and stored at 4° C. for 16 hours. The excess of substrate solution was discarded, and aliquots of Bovine Serum Albumin (BSA; 150 µl of a 5% solution in PBS) were transferred into each substrate-coated-assay well and incubated for 1 hour at ambient temperature to block non specific binding. The assay plate wells were washed in turn with PBS containing 0.05% v/v Tween 20 (PBST) and with Hepes pH7.4 buffer (50 mM, 300 µl/well) before being blotted dry.

Each test compound was dissolved in dimethyl sulphoxide and diluted with distilled water to give a series of dilutions (from 100 µM to 0.001 µM). Portions (25 µl) of each dilution of test compound were transferred to wells in the washed assay plates. "Total" control wells contained diluted DMSO instead of compound. Aliquots (25 µl) of an aqueous magnesium chloride solution (80 mM) containing adenosine-5'-triphosphate (ATP; 40 µM) was added to all test wells except the "blank" control wells which contained magnesium chloride without ATP.

Active human c-Src kinase (recombinant enzyme expressed in Sf9 insect cells; obtained from Upstate Biotechnology Inc. product 14-117) was diluted immediately prior to use by a factor of 1:10,000 with an enzyme diluent which comprised 100 mM Hepes pH7.4 buffer, 0.2 mM sodium orthovanadate, 2 mM dithiothreitol and 0.02% BSA. To start the reactions, aliquots (50 µl) of freshly diluted enzyme were added to each well and the plates were incubated at ambient temperature for 20 minutes. The supernatant liquid in each well was discarded and the wells were washed twice with PBST. Mouse IgG anti-phosphotyrosine antibody (Upstate Biotechnology Inc. product 05-321; 100 µl) was diluted by a factor of 1:6000 with PBST containing 0.5% w/v BSA and added to each well. The plates were incubated for 1 hour at ambient temperature. The supernatant liquid was discarded and each well was washed with PBST (×4). Horse radish peroxidase (HRP)-linked sheep anti-mouse Ig antibody (Amersham Catalogue No. NXA 931; 100 µl) was diluted by a factor of 1:500 with PBST containing 0.5% w/v BSA and added to each well. The plates were incubated for 1 hour at ambient temperature. The supernatant liquid was discarded and the wells were washed with PBST (×4).

A PCSB capsule (Sigma Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2'-azinobis(3-ethylbenzothiazoline-6-sulphonic acid) (ABTS; Boehringer Catalogue No. 1204 521). Aliquots (100 µl) of the resultant solution were added to each well. The plates were incubated for 20 to 60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro c-Src transfected NIH 3T3 (c-src 3T3) Fibroblast Proliferation Assay This assay determined the ability of a test compound to inhibit the proliferation of National Institute of Health (NIH) mouse 3T3 fibroblast cells that had been stably-transfected with an activating mutant (Y530F) of human c-Src.

Using a similar procedure to that described by Shalloway et al., *Cell*, 1987, 49, 65-73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$: 95% air) incubator.

Test compounds were solubilised in DMSO to form a 10mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5% $CO_2$: 95% air) incubator.

BrdU labelling reagent (Boehringer Mannheim Catalogue No. 647 229) was diluted by a factor of 1:100 in DMEM medium containing 0.5% FCS and aliquots (20 µl) were added to each well to give a final concentration of 10 µM). The plates were incubated at 37° C. for 2 hours. The medium was decanted. A denaturating solution (FixDenat solution, Boehringer Mannheim Catalogue No. 647 229; 50 µl) was added to each well and the plates were placed on a plate shaker at ambient temperature for 45 minutes. The supernatant was decanted and the wells were washed with PBS (200 µl per well). Anti-BrdU-Peroxidase solution (Boehringer Mannheim Catalogue No. 647 229) was diluted by a factor of 1:100 in PBS containing 1% BSA and 0.025% dried skimmed milk (Marvel (registered trade mark), Premier Beverages, Stafford, GB) and an aliquot (100 µl) of the resultant solution was added to each well. The plates were placed on a plate shaker at ambient temperature for 90 minutes. The wells were washed with PBS (×5) to ensure removal of non-bound antibody conjugate. The plates were blotted dry and tetramethylbenzidine substrate solution (Boehringer Mannheim Catalogue No. 647 229; 100 µl).was added to each well. The plates were gently agitated on a plate shaker while the colour developed during a 10 to 20 minute period. The absorbance of the wells was measured at 690 nm. The extent of inhibition of cellular proliferation at a range of concentrations of each test compound was determined and an anti-proliferative $IC_{50}$ value was derived.

(c) In Vitro Microdroplet Migration Assay

This assay determines the ability of a test compound to inhibit the migration of adherent mammalian cell lines, for example the human tumour cell line A549.

RPMI medium(Sigma) containing 10% FCS, 1% L-glutamine and 0.3% agarose (Difco Catalogue No. 0142-

01) was warmed to 37° C. in a water bath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2\times10^7$ cells/ml in the medium and maintained at a temperature of 37° C.

A droplet (2 µl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-containing droplets. Aliquots (90 µl) of medium which had been cooled to 4° C. were transferred into each well, taking care not to disturb the microdroplets. Test compounds were diluted from a 10 mM stock solution in DMSO using RPMI medium as described above. Aliquots (10 µl) of the diluted test compounds were transferred to the wells, again taking care not to disturb the microdroplets. The plates were incubated at 37° C. in a humidified (7.5% $CO_2$: 95% air) incubator for about 48 hours.

Migration was assessed visually and the distance of migration was measured back to the edge of the agar droplet. A migratory inhibitory $IC_{50}$ was derived by plotting the mean migration measurement against test compound concentration.

(d) In Vivo A549 Xenograft Growth Assay

This test measures the ability of compounds to inhibit the growth of the A549 human carcinoma grown as a tumour in athymic nude mice (Alderley Park nu/nu strain). A total of about $5\times10^6$ A549 cells in matrigel (Beckton Dickinson Catalogue No. 40234) were injected subcutaneously into the left flank of each test mouse and the resultant tumours were allowed to grow for about 14 days. Tumour size was measured twice weekly using callipers and a theoretical volume was calculated. Animals were selected to provide control and treatment groups of approximately equal average tumour volume. Test compounds were prepared as a ball-milled suspension in 1% polysorbate vehicle and dosed orally once daily for a period of about 28 days. The effect on tumour growth was assessed.

Although the pharmacological properties of the compounds of the Formula I vary with structural change as expected, in general activity possessed by compounds of the Formula I, may be demonstrated at the following concentrations or doses in one or more of the above tests (a), (b), (c) and (d):—

Test (a):—$IC_{50}$ in the range, for example, 0.001-10 µM;
Test (b):—$IC_{50}$ in the range, for example, 0.01-20 µM;
Test (c):—activity in the range, for example, 0.1-25 µM;
Test (d):—activity in the range, for example, 1-200 mg/kg/day.

No physiologically-unacceptable toxicity was observed in Test (d) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinoline derivative of the Formula I, or a pharmaceutically-acceptable salt thereof, as defined hereinbefore for use in a method of treatment of the human or animal body by therapy.

As stated above, it is known that the predominant role of c-Src non-receptor tyrosine kinase is to regulate cell motility which is necessarily required for a localised tumour to progress through the stages of dissemination into the blood stream, invasion of other tissues and initiation of metastatic tumour growth. We have found that the quinoline derivatives of the present invention possess potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Accordingly the quinoline derivatives of the present invention are of value as anti-tumour agents, in particular as selective inhibitors of the motility, dissemination and invasiveness of mammalian cancer cells leading to inhibition of metastatic tumour growth. Particularly, the quinoline derivatives of the present invention are of value as anti-invasive agents in the containment and/or treatment of solid tumour disease. Particularly, the compounds of the present invention are expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the compounds of the present invention are expected to be useful in the prevention or treatment of those tumours which are mediated alone or in part by inhibition of the enzyme c-Src, i.e. the compounds may be used to produce a c-Src enzyme inhibitory effect in a warm-blooded animal in need of such treatment. Specifically, the compounds of the present invention are expected to be useful in the prevention or treatment of solid tumour disease.

Thus according to this aspect of the invention there is provided a quinoline derivative of the Formula I, or a pharmaceutically-acceptable salt thereof, as defined hereinbefore for use as an anti-invasive agent in the containment and/or treatment of solid tumour disease.

According to a further feature of this aspect of the invention there is provided the use of a quinoline derivative of the Formula I, or a pharmaceutically-acceptable salt thereof, as defined hereinbefore in the manufacture of a medicament for use as an anti-invasive agent in the containment and/or treatment of solid tumour disease.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in the prevention or treatment of solid tumour disease in a warm-blooded animal such as man.

According to a further feature of this aspect of the invention there is provided a method for the prevention or treatment of solid tumour disease in a warm-blooded animal, such as man, in need of such treatment which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in providing a c-Src kinase inhibitory effect.

According to a further feature of this aspect of the invention there is provided a method for providing a c-Src kinase inhibitory effect which comprises administering to said animal an effective amount of a quinoline derivative of the Formula I, or a pharmaceutically-acceptable salt thereof, as defined hereinbefore.

The anti-invasive treatment defined hereinbefore may be applied as a sole therapy or may involve, in addition to the quinoline derivative of the invention, conventional surgery or radiotherapy or chemotherapy. Such chemotherapy may include one or more of the following categories of anti-tumour agents:—

(i) other anti-invasion agents (for example metalloproteinase inhibitors like marimastat and inhibitors of urokinase plasminogen activator receptor function);

(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-N-(prop-2-ynyl)amino]benzamido} 4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5α-reductase such as finasteride;

(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family; and (v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinoline derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of c-Src. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (WPLC) was performed on C18 reverse phase silica, for example on a Dynamax C-18 60 Å preparative reversed-phase column;

(iv) yields, where present, are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture;

(viii) the following abbreviations have been used:—
DMF N,N-dimethylformamide
DMSO dimethylsulphoxide
THF tetrahydrofuran
DMA N,N-dimethylacetamide

EXAMPLE 1

4-(6-chloro-2,3-methylenedioxyanilino)-7-(3-chloropropoxy)-3-cyano-6-methoxyquinoline Sodium hexamethyldisilazane (1M solution in THF; 3.34 ml) was added to a solution of 6-chloro-2,3-methylenedioxyaniline (0.573 g) in DMF (12 ml) that was cooled to 0° C. and the mixture was stirred for 5 minutes. A solution of 4-chloro-7-(3-chloropropoxy)-3-cyano-6-methoxyquinoline (0.5 g) in DMF (3 ml) was added and the resultant mixture was stirred at ambient temperature for 1 hour. The reaction mixture was diluted with water and extracted with ethyl acetate. The organic phase was washed with water and with brine, dried over magnesium sulphate and evaporated. The residue was purified by column chromatography on silica increasingly polar mixtures of methylene chloride and ethyl acetate as eluent. There was thus obtained the title compound as a solid (0.62 g); NMR Spectrum: DMSOd$_6$ at 60° C.) 2.32 (m, 2H), 3.9 (m, 2H), 4.0 (s, 3H), 4.35 (m, 2H), 6.1 (s, 2H), 7.0 (d, 1H), 7.1 (d, 1H), 7.4 (s, 1H), 7.9 (s, 1H), 8.42 (s, 1H), 9.32 (s, 1H); Mass Spectrum: M+H$^+$ 446 and 448.

The 4-chloro-7-(3-chloropropoxy)-3-cyano-6-methoxyquinoline used as a starting material was prepared as follows:—

A mixture of 4-chloro-3-cyano-7-hydroxy-6-methoxyquinoline (0.2 g, prepared as described in International Patent Application WO 00/68201, disclosed as compound (7) within Preparation 1 therein), potassium tert-butoxide (0.1 g) and DMF (8 ml) was stirred at ambient temperature for 15 minutes. 1-Bromo-3-choropropane (0.134 g) was added and the reaction mixture was stirred at ambient temperature for 16 hours. The resultant mixture was evaporated and the residue was partitioned between methylene chloride and an aqueous sodium bicarbonate solution. The organic layer was dried using magnesium sulphate and evaporated. The residue was purified by column chromatography on silica using increasingly polar mixtures of ethyl acetate and hexane. There was thus obtained the required starting material (0.131 g); NMR Spectrum: (DMSOd$_6$) 2.3 (m, 2H), 3.8 (m, 2H), 4.0 (s, 3H), 4.35 (m, 2H), 7.42 (s, 1), 7.68 (s, 1H), 8.95 (s, 1H); Mass Spectrum: M+H$^+$ 311.

The 6-chloro-2,3-methylenedioxyaniline used as a starting material was prepared as follows:—

Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition, the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185-187° C.; NMR Spectrum: (CDCl$_3$) 6.0 (s, 2H); 6.7 (d, 1m); 6.75-6.9 (m, 2H).

A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to ambient temperature and was stirred for a further hour. Water was added and the organic solvent was evaporated. The residue was acidified to pH2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: (DMSOd$_6$) 6.15 (s, 2H), 7.0 (m, 2H), 13.7 (br s, 1H).

A portion (1' g) of the material so obtained was dissolved in 1,4dioxane (15 ml) and anhydrous tert-butanol (4 ml), diphenylphosphoryl azide (1.12 ml) and triethylamine (0.73 ml) were added in turn. The resultant mixture was stirred and heated to 100° C. for 4 hours. The mixture was evaporated and the residue was partitioned between ethyl acetate and a 5% aqueous citric acid solution. The organic phase was washed in turn with water, a saturated aqueous sodium bicarbonate solution and brine, dried over magnesium sulphate and evaporated. The residue was purified by column chromatography on silica using a 9:1 mixture of petroleum ether (b.p. 40-60° C.) and ethyl acetate as eluent. There was thus obtained tert-butyl N-(5-chloro-1,3-benzodioxol-4-yl)carbamate (1.1 g); NMR Spectrum: (DMSOd$_6$) 1.45 (s, 9H), 6.1 (s, 2H), 6.85 (d, 1H), 6.95 (d, 1H), 8.75 (s, 1H).

A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was washed with brine, dried over magnesium sulphate and evaporated. There was thus obtained 6-chloro-2,3-methylenedioxyaniline (0.642 g); NMR Spectrum: (DMSOd$_6$) 5.15 (s, 2H), 6.0 (s, 2H), 6.25 (d, 1H), 6.75 (d, 1H).

EXAMPLE 2

4-(6-chloro-2,3-methylenedioxyamino)-3-cyano-6-methoxy-7-[3-(4-methylpiperazin-1-yl)propoxy]quinoline A mixture of 4-(6-chloro-2,3-methylenedioxyanilino)-7-(3-chloropropoxy)-3-cyano-6-methoxyquinoline (0.1 g), N-methylpiperazine (0.075 ml) and DMF (2 ml) was stirred and heated to 60° C. for 24 hours. The cooled mixture was evaporated and the resultant residue was purified by column chromatography on silica using increasingly polar mixtures of methylene chloride and a saturated methanolic ammonia solution as eluent. There was thus obtained the title compound (0.051 g); NMR Spectrum: (DMSOd$_6$ and CF$_3$CO$_2$D) 2.35 (m, 2H) 2.95 (s, 3H), 3.45 (m, 2H), 3.2-4.0 (m, 8H), 4.02 (s, 3H), 4.32 (m, 2H), 6.15 (m, 2H), 7.08 (d, 1H), 7.15 (d, 1H), 7.48 (s, 1H), 8.15 (s, 1H), 9.15 (s, 1H); Mass Spectrum: M+H$^+$ 511.

EXAMPLE 3

7-(3-chloropropoxy)-3-cyano-6-methoxy-4-(2,3-methylenedioxyanilino)quinoline

Using an analogous procedure to that described in Example 1,4-chloro-7-(3-chloropropoxy)-3-cyano-6-methoxyquinoline was reacted with 2,3-methylenedioxyaniline to give the title compound as a solid (0.62 g); NMR Spectrum: (DMSOd$_6$ and CF$_3$CO$_2$D) 2.4 (m, 2H), 3.85 (m, 2H), 3.95 (s, 3H), 4.3 (m, 2H), 6.0 (s, 2H), 6.8-7.0 (m, 2H), 7.35 (s, 1H), 7.8 (s, 1H), 8.45 (s, 1H), 9.6 (br s, 1H); Mass Spectrum: M+H$^+$ 412.

The 2,3-methylenedioxyaniline used as a starting material was prepared as follows:—

A mixture of 2,3-dihydroxybenzoic acid (5 g), methanol (50 ml) and concentrated sulphuric acid (10 drops) was stirred and heated to 60° C. for 24 hours. The mixture was evaporated and the residue was taken up in ethyl acetate. The organic solution was washed with a saturated solution of sodium bicarbonate, dried over magnesium sulphate and evaporated to give methyl 2,3-dihydroxybenzoate (2.19 g); NMR Spectrum: (CDCl$_3$) 3.95 (s, 3H), 5.7 (s, 1H), 6.8 (t, 1H), 7.15 (d, H), 7.35 (d, H).

After repetition of the previous reaction, a mixture of methyl 2,3-dihydroxybenzoate (2.8 g), potassium fluoride (4.8 g) and DMF (45 ml) was stirred at ambient temperature for 30 minutes. Dibromomethane (1.28 ml) was added and the mixture was heated to 120° C. for 3 hours. The mixture was cooled to ambient temperature, poured into water and extracted with diethyl ether. The organic phase was washed with water and with brine, dried over magnesium sulphate and evaporated. The residue was purified by column chromatography using a 9:1 mixture of petroleum ether (b.p. 40-60° C.) and ethyl acetate as eluent. There was thus obtained methyl 2,3-methylenedioxybenzoate (2.3 g) as a solid; NMR Spectrum: (CDCl$_3$) 3.95 (s, 3H), 6.1 (s, 2H), 6.85 (t; 1H), 7.0 (d, 1H), 7.45 (d, 1H).

A mixture of the material so obtained, a 2N aqueous potassium hydroxide solution (15.5 ml) and methanol (40 ml) was stirred at ambient temperature for 2 hours. The solution was concentrated to about one quarter of the original volume and cooled in an ice bath. The mixture was acidified to pH3.5 by the addition of a 2N aqueous hydrochloric acid solution. The resultant precipitate was collected by filtration and washed in turn with water and diethyl ether. There was thus obtained 2,3-methylenedioxybenzoic acid (1.87 g); NMR Spectrum: (DMSOd$_6$) 6.1 (s, 1H), 6.9 (t, 1H), 7.15 (d, 1H), 7.3 (d, 1H), 13.0 (br s, 1H).

The material so obtained was suspended in anhydrous dioxane (30 ml) and anhydrous diphenylphosphoryl azide (2.45 ml), triethylamine (1.6 ml) and tert-butanol (9 ml) were added. The mixture was heated to reflux for 5 hours. The mixture was cooled to ambient temperature, concentrated by evaporation and diluted with ethyl acetate. The organic phase was washed in turn with a 5% aqueous citric acid solution, water, an aqueous sodium bicarbonate solution and brine and dried over magnesium sulphate. The solvent was evaporated and the residue was purified by column chromatography on silica using a 19:1 mixture of petroleum ether (b.p. 40-60° C.) and ethyl acetate as eluent. There was thus obtained tert-butyl N-(2,3-methylenedioxyphenyl)carbamate (1.98 g) as a solid; NMR Spectrum: (CDCl$_3$) 1.55 (s, 9H), 5.95 (s, 2H), 6.4 (br s, 1H), 6.55 (d, 1H), 6.8 (t, 1H), 7.45 (d, 1H).

A 5N aqueous hydrochloric acid solution (30 ml) was added to a solution of tert-butyl N-(2,3-methylenedioxyphenyl)carbamate (1.9 g) in ethanol (38 ml) and the reaction mixture was stirred at ambient temperature for 20 hours. The ethanol was evaporated and the residual aqueous phase was washed with diethyl ether and neutralised to pH7 by the addition of solid potassium hydroxide. The resultant mixture was filtered and the aqueous phase was extracted with diethyl ether. The organic phase was washed with brine, dried over magnesium sulphate and evaporated. There was thus obtained 2,3-methylenedioxyaniline (1.0 g) as an oil; NMR Spectrum: (CDCl$_3$) 3.0 (br s, 2H), 5.9 (s, 2H), 6.3 (m, 2H), 7.25 (t, 1H).

EXAMPLE 4

Using an analogous procedure to that described in Example 2, the appropriate 7-(ω-haloalkoxy)-3-cyanoquinoline was reacted with the appropriate amine or heterocycle to give the compounds described in Table I. Unless otherwise stated, each compound described in Table I was obtained as a free base.

TABLE I

| Compound No. & Note | R$^1$ | R$^2$ |
|---|---|---|
| [1] | 3-(4-hydroxypiperidin-1-yl)propoxy | 6-chloro |
| [2] | 3-morpholinopropoxy | 6-chloro |
| [3] | 3-piperidinopropoxy | 6-chloro |
| [4] | 3-pyrrolidin-1-ylpropoxy | 6-chloro |
| [5] | 3-(4-acetylpiperazin-1-yl)propoxy | 6-chloro |
| [6] | 3-(4-methylsulphonylpiperazin-1-yl) | 6-chloro |
| [7] | 3-(4-cyanomethylpiperazin-1-yl)propoxy | 6-chloro |
| [8] | 3-(4-allylpiperazin-1-yl)propoxy | 6-chloro |
| [9] | 3-(4-methylpiperazin-1-yl)propoxy | hydrogen |
| [10] | 3-(4-hydroxypiperidin-1-yl)propoxy | hydrogen |
| [11] | 3-(4-acetylpiperazin-1-yl)propoxy | hydrogen |
| [12] | 3-(4-methylsulphonylpiperazin-1-yl)propoxy | hydrogen |
| [13] | 3-(4-cyanomethylpiperazin-1-yl)propoxy | hydrogen |
| [14] | 3-(4-allylpiperazin-1-yl)propoxy | hydrogen |
| [15] | 3-(N-methyl-N-prop-2-ynylamino)propoxy | hydrogen |
| [16] | 2-(4-methylpiperazin-1-yl)ethoxy | hydrogen |
| [17] | 2-(4-acetylpiperazin-1-yl)ethoxy | hydrogen |
| [18] | 2-(4-allylpiperazin-1-yl)ethoxy | hydrogen |
| [19] | 2-prop-2-ynylaminoethoxy | hydrogen |
| [20] | 2-(N-methyl-N-prop-2-ynylamino)ethoxy | hydrogen |
| [21] | 3-(3-fluoropyrrolidin-1-yl)propoxy | hydrogen |
| [22] | 3-(3,3-difluoropyrrolidin-1-yl)propoxy | hydrogen |
| [23] | 3-(4-fluoropiperidin-1-yl)propoxy | hydrogen |
| [24] | 3-(4,4-difluoropiperidin-1-yl)propoxy | hydrogen |
| [25] | 3-morpholinopropoxy | 4-bromo |
| [26] | 3-(4-tert-butoxycarbonylpiperazin-1-yl)propoxy | hydrogen |
| [27] | 4-(4-methylpiperazin-1-yl)butoxy | hydrogen |
| [28] | 4-(4-acetylpiperazin-1-yl)butoxy | 6-chloro |
| [29] | 3-(1,2,3,6-tetrahydropyridin-1-yl)propoxy | hydrogen |
| [30] | 4-(1,2,3,6-tetrahydropyridin-1-yl)butoxy | hydrogen |
| [31] | 3-(2,5-dimethylpyrrol-1-yl)propoxy | hydrogen |
| [32] | 3-(2,5-dimethyl-3-pyrrolin-1-yl)propoxy | hydrogen |
| [33] | (2S)-2-fluoro-3-(1,2,3,6-tetrahydropyridin-1-yl)propoxy | hydrogen |
| [34] | (2S)-2-fluoro-3-morpholinopropoxy | hydrogen |
| [35] | 3-morpholinopropoxy | 4-(2-methoxyethyl) |

TABLE I-continued

| Compound No. & Note | R$^1$ | R$^2$ |
|---|---|---|

Notes

[1] 4-Hydroxypiperidine was used as the heterocycle reactant. The reaction product was purified by column chromatography on reversed-phase silica using decreasingly polar mixtures of acetonitrile and a 1% solution of acetic acid in water. The material so obtained was dissolved in methylene chloride and the solution was dried over magnesium sulphate. The solution was filtered, the filtrate was evaporated and the residue was triturated under a mixture of pentane and diethyl ether. The resultant precipitate was isolated and dried under vacuum. The product contained one equivalent of acetic acid and gave the following characterising data;
NMR Spectrum: (DMSOd$_6$ and CF$_3$CO$_2$D) 1.5-1.7 (m, 1H), 1.8-1.95 (m, 2H), 1.95-2.1 (m, 1H), 2.2-2.35 (m, 2H), 3.05 (m, 1H), 3.15-3.45 (m, 4H), 3.55 (d, 1H), 3.7 (m, 1H), 4.0 (s, 3H), 4.3 (m, 2H), 6.15 (d, 2H), 7.08 (d, 1H), 7.15 (d, 1H), 7.45 (s, 1H), 8.15 (s, 1H), 9.15 (s, 1H);
Mass Spectrum: M + H$^+$ 511.

[2] Morpholine was used as the heterocycle reactant. The product gave the following characterising data;
NMR Spectrum: (DMSOd$_6$ and CF$_3$CO$_2$D) 2.35 (m, 2H), 3.2 (m, 2H), 3.4 (m, 2H), 3.6 (d, 2H), 3.75 (m, 2H), 4.05 (s, 3H), 4.08 (d, 2H), 4.35 (m, 2H), 6.2 (d, 2H), 7.15 (d, 1H), 7.2 (d, 1H), 7.5 (s, 1H), 8.2 (s, 1H), 9.2 (s, 1H);
Mass Spectrum: M + H$^+$ 497 and 499.

[3] Piperidine was used as the heterocycle reactant. The product gave the following characterising data;
NMR Spectrum: (DMSOd$_6$ and CF$_3$CO$_2$D) 1.45 (m, 1H), 1.65-1.8 (m, 3H), 1.9 (d, 2H), 2.35 (m, 2H), 3.0 (m, 2H), 3.31 (m, 2H), 3.6 (d, 2H), 4.05 (s, 3H), 4.38 (m, 2H), 6.2 (d, 2H), 7.12 (d, 1H), 7.2 (d, 1H), 7.5 (s, 1H), 8.2 (s, 1H), 9.2 (s, 1H);
Mass Spectrum: M + H$^+$ 495 and 497.

[4] Pyrrolidine was used as the heterocycle reactant. The product gave the following characterising data;
NMR Spectrum: (DMSOd$_6$ and CF$_3$CO$_2$D) 1.9-2.0 (m, 2H), 2.1 (m, 2H), 2.35 (m, 2H), 3.05-3.2 (m, 2H), 3.45 (m, 2H), 3.75 (m, 2H), 4.08 (s, 3H), 4.35 (m, 2H), 6.2 (d, 2H), 7.12 (d, 1H), 7.2 (d, 1H), 7.5 (s, 1H), 8.2 (s, 1H), 9.2 (s, 1H);
Mass Spectrum: M + H$^+$ 481 and 483.

[5] 1-Acetylpiperazine was used as the heterocycle reactant. The product gave the following characterising data;
NMR Spectrum: (DMSOd$_6$ and CF$_3$CO$_2$D) 2.1 (s, 3H), 2.38 (m, 2H), 2.95-3.1 (m, 2H), 3.2 (m, 1H), 3.35-3.55 (m, 3H), 3.65 (d, 2H), 4.08 (s, 3H), 4.05-4.15 (m, 1H), 4.35 (m, 2H), 4.58 (d, 1H), 6.2 (d, 2H), 7.12 (d, 1H), 7.2 (d, 1H), 7.5 (s, 1H), 8.2 (s, 1H), 9.2 (s, 1H);
Mass Spectrum: M + H$^+$ 538.

[6] 1-Methylsulphonylpiperazine was used as the heterocycle reactant. The product gave the following characterising data;
NMR Spectrum: (DMSOd$_6$ and CF$_3$CO$_2$D) 2.3-2.4 (m, 2H), 3.08 (s, 3H), 3.12-3.35 (m, 4H), 3.45 (m, 2H), 3.75 (d, 2H), 3.85 (d, 2H), 4.05 (s, 3H), 4.35 (m, 2H), 6.2 (d, 2H), 7.15 (d, 1H), 7.2 (d, 1H), 7.5 (s, 1H), 8.2 (s, 1H), 9.2 (s, 1H);
Mass Spectrum: M + H$^+$ 574 and 576.
The 1-methylsulphonylpiperazine used as a starting material was prepared as follows:-
Mesyl chloride (0.966 ml) was added dropwise to a stirred mixture of 1-benzylpiperazine (2 g), triethylamine (1.74 ml) and methylene chloride (30 ml) which was cooled to 0° C. The reaction mixture was allowed to warm to ambient temperature and stirred for 1 hour. The mixture was partitioned between methylene chloride and water. The organic phase was washed with water and with brine, dried over magesium sulphate and evaporated.
The residue was purified by column chromatography on silica using a 7:3 mixture of methylene chloride and ethyl acetate as eluent. There was thus obtained 1-benzyl-4-methylsulphonylpiperazine (2.5 g) as a solid;
NMR Spectrum: (CDCl$_3$) 2.6 (m, 4H), 2.8 (s, 3H), 3.3 (m, 4H), 3.55 (s, 2H), 7.3 (m, 5H);

TABLE I-continued

Compound
No. & Note  R¹  R²

Mass Spectrum: M + H⁺ 255.
A mixture of the material so obtained, cyclohexene (30 ml), palladium oxide on charcoal catalyst (20%; 0.5 g) and ethanol (70 ml) was stirred and heated to 80° C. for 4 hours. The catalyst was removed by filtration and the solvent was evaporated to give 1-methylsulphonylpiperazine (1.58 g) as a solid;
NMR Spectrum: (CDCl₃) 2.8 (s, 3H), 3.0 (m, 4H), 3.2 (m, 4H);
Mass Spectrum: M + H⁺ 165.

[7] 1-Cyanomethylpiperazine was used as the heterocycle reactant. The product gave the following characterising data;
NMR Spectrum: (DMSOd₆ and CF₃CO₂D) 2.3-2.4 (m, 2H), 2.65-2.8 (m, 2H), 3.05-3.15 (m, 2H), 3.15-3.3 (m, 2H), 3.4 (m, 2H), 3.7 (br s, 2H), 3.9 (s, 2H), 4.1 (s, 3H), 4.35 (m, 2H), 6.2 (d, 2H), 7.12 (d, 1H), 7.2 (d, 1H), 7.5 (s, 1H), 8.2 (s, 1H), 9.2 (s, 1H);
Mass Spectrum: M + H⁺ 535 and 537.
The 1-cyanomethylpiperazine used as a starting material was prepared as follows:-
A mixture of 1-(tert-butoxycarbonyl)piperazine (5 g), 2-chloroacetonitrile (1.9 ml), potassium carbonate (4 g) and DMF (20 ml) was stirred at ambient temperature for 16 hours. A saturated aqueous ammonium chloride solution was added and the mixture was extracted with ethyl acetate. The organic phase was dried over magnesium sulphate and evaporated. The residue was purified by column chromatography on silica using diethyl ether as eluent. There was thus obtained 1-(tert-butoxycarbonyl)-4-cyanomethylpiperazine as a solid (5.7 g);
NMR Spectrum: (CDCl₃) 1.45 (s, 9H), 2.5 (m, 4H), 3.45 (m, 4H), 3.55 (s, 2H).
A mixture of the material so obtained, trifluoroacetic acid (20 ml) and methylene chloride (25 ml) was stirred at ambient temperature for 4 hours. The mixture was evaporated, toluene was added and the mixture was evaporated again. The residue was purified by column chromatography on silica using a 9:1 mixture of methylene chloride and methanol as eluent. There was thus obtained 1-cyanomethylpiperazine trifluoroacetate salt which was treated with solid sodium bicarbonate in a mixture of methylene chloride, ethyl acetate and methanol to give the free base form (2.9 g);
NMR Spectrum: (CDCl₃ and DMSO₆ ) 2.7 (m, 4H), 3.2 (m, 4H), 3.6 (s, 2H), 6.2 (br s, 1H).

[8] 1-Allylpiperazine was used as the heterocycle reactant. The product gave the following characterising data;
NMR Spectrum: (DMSOd₆ and CF₃CO₂D) 2.3-2.4 (m, 2H), 3.5 (m, 2H), 3.45-3.9 (m, 8H), 3.95 (d, 2H), 4.08 (s, 3H), 4.38 (m, 2H), 5.6-5.7 (m, 2H), 5.9-6.0 (m, 1H), 6.2 (d, 2H), 7.1 (d, 1H), 7.2 (d, 1H), 7.5 (s, 1H), 8.2 (s, 1H), 9.2 (s, 1H);
Mass Spectrum: M + H⁺ 536 and 538.

[9] 1-Methylpiperazine was used as the heterocycle reactant. The product gave the following characterising data;
NMR Spectrum: (DMSOd₆ and CF₃CO₂D) 2.25-2.4 (m, 2H), 2.97 (s, 3H), 3.2-4.0 (m,8H), 3.45 (m, 2H), 40 (s, 3H), 4.32 (m, 2H), 6.1 (s, 2H), 6.95-7.05 (m, 3H), 7.45 (s, 1H), 8.1 (s, 1H), 9.15 (s, 1H);
Mass Spectrum: M + H⁺ 476.

[10] The reaction product was purified by column chromatography on reversed-phase silica using decreasingly polar mixtures of acetonitrile and a 1% solution of acetic acid in water. The product contained one equivalent of acetic acid and gave the following characterising data;
NMR Spectrum: (DMSOd₆ and CF₃CO₂D) 1.5-1.7 (m, 1H), 1.7-1.95 (m, 2H), 1.95-2.05 (m, 1H), 2.2-2.4 (m, 2H), 3.02 (m, 2H), 3.15-3.45 (m, 4H), 3.55 (d, 1H), 3.6 (m, 1H), 4.0 (s, 3H), 4.3 (m, 2H), 6.1 (s, 2H), 6.95-7.05 (m, 3H), 7.4 (s, 1H), 8.1 (s, 1H), 9.12 (s, 1H);
Mass Spectrum: M + H⁺ 477.

[11] The reaction product was purified by column chromatography on reversed-phase silica using decreasingly polar mixtures of acetonitrile and a 1% solution of acetic acid in water. The product contained 0.5 equivalents of acetic acid and gave the following characterising data;

NMR Spectrum: (DMSOd₆ and CF₃CO₂D) 2.1 (s, 3H), 2.35 (m, 2H), 2.9-3.1 (m, 2H), 3.2 (m, 1H), 3.3-3.5 (m, 3H), 3.65 (d, 2H), 4.05 (s, 3H), 4.07 (m, 1H), 4.35 (m, 2H), 4.55 (d, 1H), 6.12 (s, 2H), 7.0-7.1 (m, 3H), 7.5 (s, 1H), 8.15 (s, 1H), 9.2 (s, 1H);
Mass Spectrum: M + H⁺ 504.

[12] The reaction product was purified by column chromatography on reversed-phase silica using decreasingly polar mixtures of acetonitrile and a 1% solution of acetic acid in water. The product contained 0.9 equivalents of acetic acid and gave the following characterising data;
NMR Spectrum: (DMSOd₆ and CF₃CO₂D) 2.3-2.4 (m, 2H), 3.0 (s, 3H), 3.1-3.3 (m, 4H), 3.4 (m, 2H), 3.7 (d, 2H), 3.8 (d, 2H), 4.0 (s, 3H), 4.3 (m, 2H), 6.1 (s, 2H), 6.95-7.05 (m, 3H), 7.45 (s, 1H), 8.1 (s, 1H), 9.12 (s, 1H);
Mass Spectrum: M + H⁺ 540.

[13] The product gave the following characterising data;
NMR Spectrum: (DMSOd₆ and CF₃CO₂D) 2.25-2.4 (m, 2H), 2.6-2.75 (m, 2H), 3.05 (d, 2H), 3.2 (m, 2H), 3.38 (m, 2H), 3.7 (d, 2H), 3.9 (s, 2H), 4.05 (s, 3H), 4.35 (m, 2H), 6.12 (s, 2H), 7.0-7.1 (m, 3H), 7.5 (s, 1H), 8.15 (s, 1H), 9.18 (s, 1H);
Mass Spectrum: M + H⁺ 501.

[14] The product gave the following characterising data;
NMR Spectrum: (DMSOd₆ and CF₃CO₂D) 2.25-2.4 (m, 2H), 3.2-3.9 (m, 8H), 3.45 (m, 2H), 3.95 (d, 2H), 4.02 (s, 3H), 4.35 (m, 2H), 5.55-5.65 (m, 2H), 5.85-6.0 (m, 1H), 6.1 (s, 2H), 6.95-7.1 (m, 3H), 7.45 (s, 1H), 8.1 (s, 1H), 9.15 (s, 1H);
Mass Spectrum: M + H⁺ 502.

[15] The reactants were 7-(3-bromopropoxy)-3-cyano-6-methoxy-4-(2,3-methylenedioxyanilino)quinoline (obtained as described in Example 8) and N-methyl-N-prop-2-ynylamine and the reaction mixture was stiired at ambient temperature for 24 hours. The material so obtained was dissolved in diethyl ether and a solution of hydrogen chloride in diethyl ether (1M, 2 ml) was added. The resultant solid was washed with diethyl ether. Thereby, the product was obtained as a dihydrochloride salt and gave the following characterising data;
NMR Spectrum: (DMSOd₆ ) 2.3 (m, 2H), 2.82 (s, 3H), 3.23-3.39 (m, 2H), 3.84 (m, 1H), 4.0 (s, 3H), 4.15 (d, 2H), 4.3 (t, 2H), 6.03 (s, 2H), 6.92-7.0 (m, 3H), 7.54 (s, 1H), 8.21 (s, 1H), 8.93 (s, 1H);
Mass Spectrum: M + H⁺ 445.

[16] 7-(2-Bromoethoxy)-3-cyano-6-methoxy-4-(2,3-methylenedioxyanilino) quinoline (obtained as described in Example 9) was used as a reactant and the reaction mixture was stirred at ambient temperature for 24 hours rather than being heated to 60° C. The product gave the following characterising data;
NMR Spectrum: (DMSOd₆ and CF₃CO₂D) 2.12 (s, 3H), 2.24-2.36 (m, 4H), 2.45-2.55 (m, 4H), 2.75 (t, 2H), 3.9 (s, 3H), 4.23 (t, 2H), 5.97 (s, 2H), 6.8-6.93 (m, 3H), 7.32 (s, 1H), 7.75 (s, 1H), 8.41 (s, 1H), 9.48 (s, 1H);
Mass Spectrum: M + H⁺ 462.

[17] 7-(2-Bromoethoxy)-3-cyano-6-methoxy-4-(2,3-methylenedioxyanilino) quinoline was used as a reactant and the reaction mixture was stirred at ambient temperature for 24 hours. The material so obtained was dissolved in diethyl ether and a solution of hydrogen chloride in diethyl ether (1M, 2 ml) was added. The resultant solid was washed with diethyl ether. Thereby, the product was obtained as a dihydrochloride salt and gave the following characterising data;
NMR Spectrum: (DMSOd₆ and CF₃CO₂D) 2.04 (s, 3H), 3.0-3.64 (m, 8H), 3.69 (m, 2H), 4.0 (s, 3H), 4.68 (m, 2H), 6.06 (s, 2H), 6.94-7.01 (m, 3H), 7.53 (s, 1H), 8.19 (s, 1H), 8.99 (s, 1H);

TABLE I-continued

[Structure: 1,3-benzodioxole (with position 4 marked) connected via NH to a quinoline bearing CN at 3-position, MeO at 6-position, R¹ at 7-position, and R² on the benzodioxole ring at position 6]

Compound
No. & Note  R¹                                              R²

Mass Spectrum: M + H⁺ 477.

[18] 7-(2-Bromoethoxy)-3-cyano-6-methoxy-4-(2,3-methylenedioxyanilino)
quinoline was used as a reactant arid the reaction mixture was stirred at
ambient temperature for 24 hours. The material so obtained was dissolved in
diethyl ether and a solution of hydrogen chloride in diethyl ether (1M, 2 ml)
was added. The resultant solid was washed with diethyl ether. Thereby, the
product was obtained as a dihydrochloride salt and gave the following characterising data;
NMR Spectrum: (DMSOd₆) 3.3-3.82 (m, 12H), 4.02 (s, 3H), 4.61 (m, 2H),
5.48-5.6 (m, 2H), 5.9-6.03 (m, 1H), 6.04 (s, 2H), 6.93-7.0 (m, 3H), 7.58. (s,
1H), 8.28 (s, 1H), 8.98 (s, 1H);
Mass Spectrum: M + H⁺ 488.

[19] 7-(2-Bromoethoxy)-3-cyano-6-methoxy-4-(2,3-methylenedioxyanilino)
quinoline was used as a reactant and the reaction mixture was stirred at
ambient temperature for 24 hours. The material so obtained was dissolved in
diethyl ether and a solution of hydrogen chloride in diethyl ether (1M, 2 ml)
was added. The resultant solid was washed with diethyl ether. Thereby, the
product was obtained as a dihydrochloride salt and gave the following characterising data;
NMR Spectrum: (DMSOd₆) 3.5 (m, 2H), 3.71 (m, 1H), 4.0 (s, 5H), 4.54 (m,
2H), 6.03 (s, 2H), 6.9-7.0 (m, 3H), 7.58 (s, 1H), 8.28 (s, 1H), 8.94 (s, 1H),
9.83 (br s, 1H);
Mass Spectrum: M + H⁺ 417.

[20] 7-(2-Bromoethoxy)-3-cyano-6-methoxy-4-(2,3-methylenedioxyanilino)
quinoline was used as a reactant and the reaction mixture was stirred at
ambient temperature for 24 hours. The material so obtained was dissolved in
diethyl ether and a solution of hydrogen chloride in diethyl ether (1M, 2 ml)
was added. The resultant solid was washed with diethyl ether. Thereby, the
product was obtained as a dihydrochloride salt and gave the following characterising data;
NMR Spectrum: (DMSOd₆) 2.92 (s, 3H), 3.69 (m, 2H), 3.85 (m, 1H), 4.02
(s, 3H), 4.22 (d, 2H), 4.67 (t, 2H), 6.04 (s, 2H), 6.92-7.0 (m, 3H), 7.6 (s,
1H), 8.34 (s, 1H), 8.95 (s, 1H);
Mass Spectrum: M + H⁺ 431.

[21] The reactants were 7-(3-bromopropoxy)-3-cyano-6-methoxy-4-(2,3-
methylenedioxyanilino)quinoline (0.25 g), 3-fluoropyrrolidine hydrochloride
(Synthetic Letters, 1995, 1, 55-57; 0.134 g) and N,N-diisopropyl-N-ethylamine (0.4 ml) in 2-methoxyethanol (5 ml) and the mixture was stirred and
heated to 85° C. for 24 hours. The product (0.1 g) gave the following characterising data;
NMR Spectrum: (CDCl₃) 1.26 (t, 2H), 1.95-2.25 (m, 4H), 2.44-2.51 (m,
1H), 2.68-2.74 (m, 3H), 2.79-2.95 (m, 3H), 3.7 (s, 3H), 4.25 (t, 2H), 5.06-
5.28 (m, 1H), 5.94 (s, 2H), 6.62-6.65 (m, 2H), 6.73 (d, 1H), 6.83 (t, 1H),
6.97 (s, 1H), 7.37 (s, 1H), 8.61 (s, 1H).
Mass Spectrum: M + H⁺ 465.

[22] The reactants were 7-(3-bromopropoxy)-3-cyano-6-methoxy-4-(2,3-
methylenedioxyanilino)quinoline (0.25 g), 3,3-difluoropyrrolidine hydrochloride (Synthetic Letters, 1995, 1, 55-57; 0.1 g) and N,N-diisopropyl-N-
ethylamine (0.4 ml) in 2-methoxyethanol (5 ml) and the mixture was stirred
and heated to 85° C. for 24 hours. The reaction product was dissolved in
diethyl ether and a solution of hydrogen chloride in diethyl ether (4M)
was added. The resultant solid was washed with diethyl ether. Thereby, the
product was obtained as a dihydrochloride salt (0.16 g) and gave the following characterising data;
NMR Spectrum: (DMSOd₆) 2.21-2.38 (m, 2H), 2.54-2.74 (m, 2H), 3.43 (t,
2H), 3.62-426 (m, 5H), 4.32 (t, 2H), 6.06 (s, 2H), 6.94-7.03 (m, 3H), 7.57 (s,
1H), 8.26 (s, 1H), 8.98 (s, 1H), 11.22 (br s, 1H), 11.83-12.58 (m, 1H);

Mass Spectrum: M + H⁺ 483.

[23] The reactants were 7-(3-bromopropoxy)-3-cyano-6-methoxy-4-(2,3-
methylenedioxyanilino)quinoline (0.25 g); 4-fluoropiperidine hydrochloride
(J. Org. Chem., 1979, 44, 771-777; 0.17 g) and N;N-diisopropyl-N-ethylamine (0.4 ml) in 2-methoxyethanol (5 ml) and the mixture was stirred and
heated to 85° C. for 24 hours. The product (0.13 g) gave the following characterising data;
NMR Spectrum: (CDCl₃) 1.8-2.0 (m, 4H), 2.07-2.14 (m, 2H), 2.37-2.44 (m,
2H), 2.52-2.63 (m, 4H), 3.7 (s, 3H), 4.24 (t, 2H), 4.56-4.79 (m, 1H), 5.94 (s,
2H), 6.63 (d, 1H), 6.68 (s, 1H), 6.73 (d, 1H), 6.83 (t, 1H), 6.98 (s, 1H), 7.38
(s, 1H), 8.61 (s, 1H);
Mass Spectrum: M + H⁺ 479.

[24] The reactants were 7-(3-bromopropoxy)-3-cyano-6-methoxy-4-(2,3-
methylenedioxyanilino)quinoline (0.25 g), 4,4-difluoropiperidine (Tetrahedron, 1977, 33, 1707-1710; 0.154 g) and N,N-diisopropyl-N-ethylamine (0.4
ml) in 2-methoxyethanol (5 ml) and the mixture was stirred and heated to
85° C. for 24 hours. The product (0.16 g) gave the following characterising
data;
NMR Spectrum: (CDCl₃) 1.93-2.17 (m, 6H), 2.54-2.62 (m, 6H), 3.7 (s, 3H),
4.24 (t, 2H), 5.94 (s, 2H), 6.6 (d, 1H), 6.69 (s, 1H), 6.73 (d, 1H), 6.83 (t,
1H), 6.98 (s, 1H), 7.38 (s, 1H), 8.61 (s, 1H);
Mass Spectrum: M + H⁺ 497.

[25] The reactants were 4-(4-bromo-2,3-methylenedioxyanilino)-7-(3-chloropropoxy)-3-cyano-6-methoxyquinoline and morpholine and the reaction
mixture was heated to 50° C. for 12 hours. The product gave the following
characterising data;
NMR Spectrum: (DMSOd₆) 1.96 (m, 2H), 2.4-2.55 (m, 6H), 3.56 (s, 4H),
3.93 (s, 3H), 4.18 (t, 2H), 6.09 (s, 2H), 6.84 (d, 1H), 7.09 (d, 1H), 7.3 (s,
1H), 7.74 (s, 1H), 8.43 (s, 1H), 9.55 (s, 1H);
Mass Spectrum: M + H⁺ 541 and 543.
The 4-(4-bromo-2,3-methylenedioxyanilino)-7-(3-chloropropoxy)-3-cyano-
6-methoxyquinoline used as a starting material was prepared as follows:-
N-Bromosuccimide (0.23 g) was added to a solution of 2,3-methylene-
dioxyaniline (0.17 g) in acetonitrile (10 ml) and the mixture was stirred at
ambient temperature for 12 hours. The mixture was evaporated and the residue was purified by column chromatography on silica using increasingly
polar mixtures of hexane and methylene chloride as eluent. There was thus
obtained 4-bromo-2,3-methylenedioxyaniline as a solid (0.14 g);
NMR Spectrum: (DMSOd₆) 5.04 (s, 2H), 5.98 (s, 2H), 6.02 (d, 1H), 6.7 (d,
1H).
A mixture of 4-bromo-2,3-methylenedioxyaniline (0.91 g), 4-chloro-7-(3-
chloropropoxy)-3-cyano-6-methoxyquinoline (1.2 g) and 1-propanol (20 ml)
was stirred and heated to reflux for 7 hours. The resultant solid was isolated
and washed with diethyl ether. There was thus obtained 4-(4-bromo-2,3-
methylenedioxyanilino)-7-(3-chloropropoxy)-3-cyano-6-methoxyquinoline
as a solid (1.45 g);
NMR Spectrum: (DMSOd₆) 2.28 (m, 2H), 3.83 (t, 2H), 3.99 (s, 3H), 4.31 (t,
2H), 6.13 (s, 2H), 6.92 (d, 1H), 7.18 (d, 1H), 7.43 (s, 1H), 8.04 (s, 1H), 8.95
(s, 1H);
Mass Spectrum: M + H⁺ 490.

[26] The reactants were 7-(3-chloropropoxy)-3-cyano-6-methoxy-4-(2,3-
methylenedioxyanilino)quinoline and 1-(tert-butoxycarbonyl)piperazine.
Moreover, 2-methoxyethanol was used in place of DMF and the reaction
mixture was heated to 110° C. for 12 hours. The product gave the following
characterising data;
NMR Spectrum: (CDCl₃) 1.48 (s, 9H), 2.1 (m, 2H), 2.41 (m, 4H), 2.53 (t,
2H), 2.83 (m, 4H), 3.73 (s, 3H), 4.28 (t, 2H), 5.94 (s, 2H), 6.61-6.88 (m,
4H), 6.98 (s, 1H), 7.38 (s, 1H), 8.64 (s, 1H);

TABLE I-continued

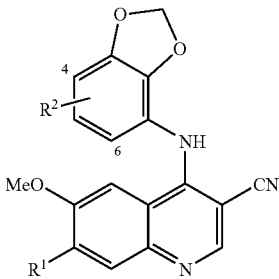

| Compound No. & Note | R¹ | R² |
|---|---|---|

Mass Spectrum: M + H⁺ 562.

[27] The reactants were 7-(4-chlorobutoxy)-3-cyano-6-methoxy-4-(2,3-methylenedioxyanilino)quinoline hydrochloride salt and 1-methylpiperazine. Moreover, 1-propanol was used in place of DMF and the reaction mixture was heated to 90° C. for 18 hours. The reaction product was dissolved in ethyl acetate and a solution of hydrogen chloride in diethyl ether (4M, 1 ml) was added. The resultant solid was isolated and washed with diethyl ether. Thereby, the product was obtained as a dihydrochloride salt and gave the following characterising data;
NMR Spectrum: ($DMSOd_6$) 1.9-1.95 (m, 4H), 2.81 (br s, 3H), 3.2-3.8 (m, 10H), 4.02 (s, 3H), 4.22 (br s, 2H), 6.04 (s, 2H), 6.93-7.01 (m, 3H), 7.59 (s, 1H), 8.26 (s, 1H), 8.97 (s, 1H), 11.28 (br s, 1H);
Mass Spectrum: M + H⁺ 490.
The 7-(4-chlorobutoxy)-3-cyano-6-methoxy-4-(2,3-methylenedioxyanilino)quinoline hydrochloride salt used as a starting material was prepared as follows:-
A mixture of 4-chloro-7-(4-chlorobutoxy)-3-cyano-6-methoxyquinoline (J. Medicinal Chemistry, 2001, 44, 3965-3977; 1.0 g), 2,3-methylenedioxyaniline (0.46 g) and 1-propanol (25 ml) was stirred and heated to 100° C. for 5 hours. The mixture was allowed to cool to ambient temperature and the precipitate was isolated and washed in turn with cold 1-propanol (25 ml) and diethyl ether (2 × 25 ml). The solid was dried under vacuum. There was thus obtained the required starting material (1.3 g);
NMR Spectrum: ($DMSOd_6$) 1.9-1.98 (m, 4H), 3.74 (t, 2H), 4.23 (t, 2H), 6.04 (s, 2H), 6.94-7.01 (m, 3H), 7.5 (s, 1H), 8.18 (s, 1H), 8.96 (s, 1H), 11.11 (br s, 1H).
[28] The reactants were 7-(4-chlorobutoxy)-3-cyano-6-methoxy-4-(2,3-methylenedioxyanilino)quinoline hydrochloride salt and 1-acetylpiperazine. Moreover, 1-propanol was used in place of DMF and the reaction mixture was heated to 90° C. for 18 hours. The reaction product was dissolved in ethyl acetate and a solution of hydrogen chloride in diethyl ether (1M, 1 ml) was added. The resultant solid was isolated and washed with diethyl ether. Thereby, the product was obtained as a dihydrochloride salt and gave the following characterising data;
NMR Spectrum: ($DMSOd_6$) 1.88-1.95 (m, 4H), 2.03 (s, 3H), 2.8-3.22 (m, 5H), 3.4-3.64 (m, 3H), 3.91-4.06 (m, 4H), 4.22 (br s, 2H), 4.37-4.42 (m, 1H), 6.05 (s, 2H), 6.92-7.02 (m, 3H), 7.62 (s, 1H), 8.31 (s, 1H), 9.01 (s, 1H), 11.21 (br s, 1H), 11.43 (br s, 1H);
Mass Spectrum: M + H⁺ 518.
[29] 1,2,3,6-Tetrahydropyridine was used as the heterocycle reactant. Moreover, 2-methoxyethanol was used in place of DMF and the reaction mixture was heated to 90° C. for 5 hours. The product gave the following characterising data;
NMR Spectrum: ($DMSOd_6$) 1.97 (m, 2H), 2.08 (s, 2H), 2.55 (m, 4H), 2.95 (s, 2H), 3.95 (s, 3H), 4.21 (t, 2H), 5.68 (m, 2H), 5.99 (s, 2H), 6.87 (m, 2H), 6.92 (t, 1H), 7.32 (s, 1H), 7.78 (s, 1H), 8.42 (s, 1H), 9.49 (s, 1H);
Mass Spectrum: M + H⁺ 459.
[30] 2-Methoxyethanol was used in place of DMF and the reaction mixture was heated to 100° C. for 2 hours. The product gave the following characterising data;
NMR Spectrum: ($CDCl_3$) 1.74 (m, 2H), 1.95 (m, 2H), 2.18 (m, 2H), 2.48 (t, 2H), 2.56 (t, 2H), 2.97 (t, 2H), 3.7 (s, 3H), 4.18 (t, 2H), 5.66 (m, 1H), 5.75 (m, 1H), 5.93 (s, 2H), 6.64 (d, 1H), 6.73 (d, 1H), 6.82 (t, 1H), 6.9 (s, 1H), 7.02 (s, 1H), 7.33 (s, 1H), 8.6 (s, 1H);
Mass Spectrum: M + H⁺ 473.
[31] 2,5-Dimethylpyrrole was used as the heterocycle reactant. Moreover, 2-methoxyethanol was used in place of DMF and the reaction mixture was heated to 95° C. for 12 hours. The product gave the following characterising data;
NMR Spectrum: ($CDCl_3$) 2.16-2.32 (m, 2H), 2.23 (s, 6H), 3.72 (s, 3H), 4.04 (t, 2H), 4.14 (t, 2H), 5.77 (s, 2H), 5.95 (s, 2H), 6.63 (m, 2H), 6.76 (d, 1H), 6.86 (m, 1H), 6.98 (s, 1H), 7.33 (s, 1H), 8.61 (s, 1H);

TABLE I-continued

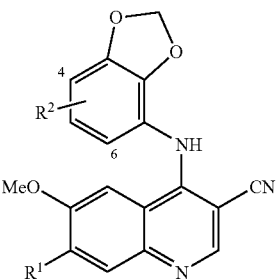

| Compound No. & Note | R¹ | R² |
|---|---|---|

Mass Spectrum: M + H⁺ 471.

[32] 2,5-Dimethyl-3-pyrroline was used as the heterocycle reactant, the material being obtained commercially as a mixture of cis and trans isomers based on the stereochemical relationship of the methyl groups. 2-Methoxyethanol was used in place of DMF and the reaction mixture was heated to 95° C. for 12 hours. Two isomeric products were obtained, based on the stereochemical relationship of the methyl groups. The isomers were separated during the chromatographic purification step and gave the following characterising data;

Isomer 1: NMR Spectrum: ($CDCl_3$) 1.16 (d, 6H), 2.08-2.18 (m, 2H), 2.91 (t, 2H), 3.61 (m, 2H), 3.72 (s, 3H), 4.27 (t, 2H), 5.55 (s, 2H), 5.92 (s, 2H), 6.63 (m, 2H), 6.73 (d, 1H), 6.86 (t, 1H), 6.98 (s, 1H), 7.39 (s, 1H), 8.61 (s, 1H);

Mass Spectrum: M − H⁻ 471.

Isomer 2: NMR Spectrum: ($CDCl_3$) 1.16 (br s, 6H), 2.08-2.13 (br s, 2H), 2.91 (br s, 2H), 3.72 (s, 3H), 3.9 (br s, 2H), 4.27 (m, 2H), 5.72 (s, 2H), 5.95 (s, 2H), 6.62-6.88 (m, 4H), 7.02 (s, 1H), 7.38 (s, 1H), 8.6 (s, 1H);

Mass Spectrum: M − H⁻ 471.

[33] The reactants were 7-[(2R)-3-chloro-2-fluoropropoxy]-3-cyano-6-methoxy-4-(2,3-methylenedioxyanilino)quinoline and 1,2,3,6-tetrahydropyridine. Moreover, 2-methoxyethanol was used in place of DMF and the reaction mixture was heated to 100° C. for 12 hours. The reaction product was purified by column chromatography on silica using increasingly polar mixtures of methylene chloride and a 7M solution of ammonia in methanol as eluent. The material so obtained was dissolved in ethyl acetate and a solution of hydrogen chloride in diethyl ether (1M, 1 ml) was added. The resultant solid was washed with diethyl ether to give the required product as a dihydrochloride salt which gave the following characterising data;
NMR Spectrum: ($DMSOd_6$) 3.18-3.96 (m, 8H), 4.05 (s, 3H), 4.46-4.63 (m, 2H), 5.68-6.0 (m, 3H), 6.07 (s, 2H), 6.92-7.02 (m, 3H), 7.62 (s, 1H), 8.33 (s, 1H), 8.97 (s, 1H), 11.28 (br s, 2H);
Mass Spectrum: M + H⁺ 477.
The 7-[(2R)-3-chloro-2-fluoropropoxy]-3-cyano-6-methoxy-4-(2,3-methylenedioxyanilino)quinoline used as a starting material was prepared as follows:-
Carbon tetrachloride (0.26 ml) was added to a mixture of (2S)-3-benzyloxy-2-fluoropropan-1-ol (J. Org. Chem., 1997, 62, 7546-7547; 0.44 g), triphenylphosphine (0.69 g) and methylene chloride (10 ml) and the mixture was stirred at ambient temperature for 12 hours. A further portion of triphenylphosphine (0.3 g) was added and the mixture was stirred at ambient temperature for 5 hours. The mixture was purified by column chromatography on silica using a 9:1 mixture of hexane and ethyl acetate as eluent. There was thus obtained (2R)-3-benzyloxy-2-fluoropropyl chloride as an oil (0.4 g);
NMR Spectrum: ($CDCl_3$) 3.66-3.81 (m, 4H), 4.55-4.62 (m, 2H), 4.71-4.87 (m, 1H), 7.28-7.38 (m, 5H).
A solution of (2R)-3-benzyloxy-2-fluoropropyl chloride (0.65 g) in methylene chloride (15 ml) was cooled to −78° C. and boron trichloride (1M solution in methylene chloride; 4.8 ml) was added. The mixture was stirred at −78° C. for 3 hours. The mixture was poured into a 1N aqueous hydrochloric acid solution (50 ml) and extracted with methylene chloride. The organic phase was dried over magnesium sulphate and concentrated by evaporation to a volume of approximately 20 ml. There was thus obtained a solution of (2R)-3-chloro-2-fluoropropan-1-ol which was used without further purification.

TABLE I-continued

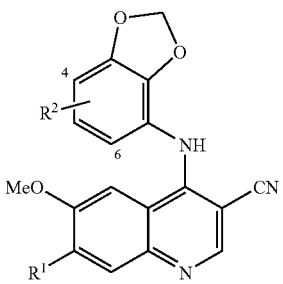

| Compound No. & Note | R¹ | R² |
|---|---|---|

Triphenylphosphine (1 g) and 4-chloro-3-cyano-7-hydroxy-6-methoxyquinoline (0.83 g) were added in turn to the solution of (2R)-3-chloro-2-fluoropropan-1-ol in methylene chloride. Diisopropyl azodicarboxylate (0.6 ml) was added and the mixture was stirred at ambient temperature for 12 hours. The mixture was poured into water and the organic layer was separated, washed with a saturated aqueous sodium chloride solution, dried over magnesium-sulphate and evaporated. The crude product so obtained was purified by column chromatography on silica using a 1:1 mixture of isohexane and ethyl acetate as eluent. There was thus obtained 4-chloro-7-[(2R)-3-chloro-2-fluoropropoxy]-3-cyano-6-methoxyquinoline (0.66 g);
NMR Spectrum: (DMSOd$_6$) 4.02 (s, 3H), 3.9-4.12 (m, 2H), 4.42-4.64 (m, 2H), 5.09-5.31 (m, 1H), 7.47 (s, 1H), 7.6 (s, 1H), 8.44 (br s, 1H), 8.98 (s, 1H).
A mixture of 4-chloro-7-[(2R)-3-chloro-2-fluoropropoxy]-3-cyano-6-methoxyquinoline (0.27 g), 2,3-methylenedioxyaniline (0.13 g) and 1-propanol was stirred and heated to 90° C. for 18 hours. The mixture was allowed to cool to ambient temperature. The precipitate was isolated and washed in turn with cold 1-propanol (10 ml) and with diethyl ether (2 × 10 ml). There was thus obtained 7-[(2R)-3-chloro-2-fluoropropoxy]-3-cyano-6-methoxy-4-(2,3-methylenedioxyanilino)quinoline (0.26 g);
NMR Spectrum: (DMSOd$_6$) 4.01 (s, 3H), 3.93-4.14 (m, 2H), 4.38-4.58 (m, 2H), 5.14-5.32 (m, 1H), 6.05 (s, 2H), 6.92-7.01 (m, 3H), 7.52 (s, 1H), 8.2 (s, 1H), 8.95 (s, 1H), 11.09 (br s, 1H);
Mass Spectrum: M + H⁺ 430.
[34] The reactants were 7-[(2R)-3-chloro-2-fluoropropoxy]-3-cyano-6-methoxy-4-(2,3-methylenedioxyanilino)quinoline and morpholine. Moreover, 2-methoxyethanol was used in place of DMF and the reaction mixture was heated to 100° C. for 12 hours. The reaction product was purified by column chromatography on silica using increasingly polar mixtures of methylene chloride and a 7M solution of ammonia in methanol as eluent. The material so obtained was dissolved in ethyl acetate and a solution of hydrogen chloride in diethyl ether (1M, 1 ml) was added. The resultant solid was washed with diethyl ether to give the required product as a dihydrochloride salt which gave the following characterising data;
NMR Spectrum: (DMSOd$_6$) 3.25-3.37 (m, 4H), 3.52-3.72 (m, 2H), 3.89-3.97 (m, 4H), 4.02 (s, 3H), 4.40-4.65 (m, 2H), 5.55-5.81 (m, 1H), 6.0 (s, 2H), 6.88-6.96 (m, 3H), 7.59 (s, 1H), 8.15 (s, 1H), 8.69 (s, 1H);
Mass Spectrum: M + H⁺ 481.
[35] The reactants were 7-(3-chloropropoxy)-3-cyano-6-methoxy-4-[4-(2-methoxyethyl)-2,3-methylenedioxyanilino]quinoline (described as Example 10(26) hereinafter) and morpholine. The reaction product was treated with a 1M solution of hydrogen chloride in diethyl ether. The resultant solid was washed with diethyl ether to give the required product as a dihydrochloride salt which gave the following characterising data;
Mass Spectrum: M − H⁻ 519.

EXAMPLE 5

3-cyano-7-hydroxy-6-methoxy-4-(2,3-methylenedioxyanilino)quinoline

A mixture of 4-chloro-3-cyano-7-hydroxy-6-methoxyquinoline (5 g), 2,3-methylenedioxyaniline (3.07 g) and propanol (100 ml) was stirred and heated to 115° C. for 18 hours. The resultant precipitate was isolated, washed in turn with propanol and diethyl ether and dried under vacuum. There was thus obtained the title compound (5.51 g); NMR Spectrum: (DMSOd$_6$) 3.99 (s, 3H), 6.06 (s, 2H), 6.93-7.0 (m, 3H), 7.48 (s, 1H), 8.16 (s, 1H), 8.94 (s, 1H); Mass Spectrum: M+H⁺ 336.

EXAMPLE 6

3-cyano-6-methoxy-7-(2-methoxyethoxy-4-(2,3-methylenedioxyanilino)quinoline

A mixture of 3-cyano-7-hydroxy-6-methoxy-4-(2,3-methylenedioxyanilino)quinoline (0.2 g), 2-bromoethyl methyl ether (0.09 g), potassium carbonate (0.22 g)and DMA (5 ml) was stirred and heated to 60° C. for 3 hours. The mixture was evaporated and the residue was partitioned between ethyl acetate and water. The organic phase was washed in turn with water, a 2N aqueous sodium hydroxide solution and brine, dried over magnesium sulphate and evaporated. The residue was purified by column chromatography on silica using increasingly polar mixtures of methylene chloride and ethyl acetate as eluent. The material so obtained was dissolved in diethyl ether and a solution of hydrogen chloride in diethyl ether (1M, 2 ml) was added. The resultant solid was washed with diethyl ether. There was thus obtained the title compound solid as a mono-hydrochloride salt (0.135 g); NMR Spectrum: (DMSOd$_6$) 3.32 (s, 3H), 3.76 (m, 2H), 3.99 (s, 3H), 4.28 (m, 2H), 6.04 (s, 2H), 6.96 (m, 3H), 7.49 (s, 1H), 8.15 (s, 1H), 8.94 (s, 1H); Mass Spectrum: M−H⁻ 392.

EXAMPLE 7

Using an analogous procedure to that described in Example 6, the appropriate 3-cyano-7-hydroxyquinoline was reacted with the appropriate alkyl halide to give the compounds described in Table II.

TABLE II

| Compound No. & Note | R¹ | R² |
|---|---|---|
| [1] | 2-(2-hydroxyethoxy)ethoxy | hydrogen |
| [2] | 2-hydroxyethoxy | hydrogen |

Notes
[1] 2-(2-Chloroethoxy)ethanol was used as the alkyl halide and the reaction mixture was heated to 60° C. for 18 hours. However, unlike in Example 6, the product was not treated with a solution of hydrogen chloride in diethyl ether and, accordingly, the product was obtained as a free base. The product gave the following characterising data;
NMR Spectrum: (DMSOd$_6$) 3.51 (m, 4H), 3.81 (m, 2H), 3.93 (s, 3H), 4.28 (m, 2H), 4.58 (m, 1H), 5.97 (s, 2H), 6.8-6.91 (m, 3H), 7.32 (s, 1H), 7.77 (s, 1H), 8.41 (s, 1H), 9.5 (s, 1H);
Mass Spectrum: M + H⁺ 424.
[2] 2-Chloroethanol was used as the alkyl halide. The product was treated with a solution of hydrogen chloride in diethyl ether. The mono-hydrochloride salt so obtained gave the following characterising data;
NMR Spectrum: (DMSOd$_6$) 3.81 (t, 2H), 3.99 (s, 3H), 4.2 (t, 2H), 6.04 (s, 2H), 6.96 (m, 3H), 7.49 (s, 1H), 8.15 (s, 1H), 8.94 (s, 1H);
Mass Spectrum: M + H⁺ 380.

EXAMPLE 8

7-3-bromopropoxy)-3-cyano-6-mehtoxy-4-(2,3-methylenedioxyanilino)quinoline

Diisopropyl azodicarboxylate (0.29 g) was added dropwise to a stirred suspension of 3-cyano-7-hydroxy-6-methoxy-4-(2,3-methylenedioxyanilino)quinoline (0.4 g), 3-bromopropanol (0.25 g), triphenylphosphine (0.44 g) and methylene chloride (15 ml). The mixture was stirred at ambient temperature for 18 hours. The mixture was evaporated and the residue was purified by column chromatography on silica eluting with increasingly polar mixtures of methylene chloride and ethyl acetate as eluent. The gum so obtained was triturated under diethyl ether. There was thus obtained the title compound as a solid (0.4 g); NMR Spectrum: (DMSOd$_6$) 2.32 (m, 2H), 3.68 (t, 2H), 3.94 (s, 3H), 4.26 (t, 2H), 5.98 (s, 2H), 6.8-6.92 (m, 3H), 7.32 (s, 1H), 7.78 (s, 1H), 8.42 (s, 1H); Mass Spectrum: M+H$^+$ 458.

EXAMPLE 9

7-(2-bromoethoxy)-3-cyano-6-methoxy-4-(2,3-methylenedioxyanilino)quinoline

Using an analogous procedure to that described in Example 8, 3-cyano-7-hydroxy-6-methoxy-4-(2,3-methylenedioxyanilino)quinoline was reacted with 2-bromoethanol to give the title compound in 82% yield; NMR Spectrum: (DMSOd$_6$) 3.88 (t, 2H), 3.94 (s, 3H), 4.51 (t, 2H), 5.96 (s, 2H), 6.8-6.93 (m, 3H), 7.34 (s, 1H), 7.8 (s, 1H), 8.42 (s, 1), 9.53 (s, 1H); Mass Spectrum: M+H$^+$ 444.

EXAMPLE 10

Using an analogous procedure to that described in Example 1, the appropriate 4chloro-3-cyanoquinoline was reacted with the appropriate 2,3-methylenedioxyaniline to give the compounds described in Table III. Unless otherwise stated, each product was obtained as a free base.

TABLE III

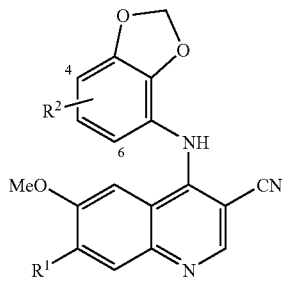

| Compound No. & Note | R$^1$ | R$^2$ |
|---|---|---|
| [1] | methoxy | hydrogen |
| [2] | methoxy | 6-chloro |
| [3] | methoxy | 6-bromo |
| [4] | 3-(4-methylpiperazin-1-yl)propoxy | 6-fluoro |
| [5] | 3-(4-methylpiperazin-1-yl)propoxy | 5-bromo |
| [6] | 3-(4-methylpiperazin-1 yl)propoxy | 4-bromo |
| [7] | 3-morpholinopropoxy | hydrogen |
| [8] | (2S)-2-fluoro-3-(4-methylpiperazin-1-yl)propoxy | hydrogen |
| [9] | methoxy | 4-iodo |
| [10] | methoxy | 4-iodo-6-chloro |
| [11] | methoxy | 6-iodo |
| [12] | methoxy | 4-bromo |
| [13] | methoxy | 5-bromo |
| [14] | methoxy | 5-fluoro |
| [15] | methoxy | 4-hydroxymethyl |
| [16] | methoxy | 4-methyl |
| [17] | methoxy | 4-benzyl |
| [18] | methoxy | 4-methylthio |
| [19] | 3-(4-methylpiperazin-1-yl)propoxy | 4-iodo |
| [20] | methoxy | 4-(2-methoxyethyl) |
| [21] | methoxy | 4-morpholinomethyl |
| [22] | methoxy | 4-dimethylaminomethyl |
| [23] | methoxy | 4-oxazol-5-yl |
| [24] | 3-(4-methylpiperazin-1-yl)propoxy | 4-(2-methoxyethyl) |
| [25] | 3-(1,1-dioxotetrahydro-4H-thiazin-4-yl)propoxy | 4-(2-methoxyethyl) |
| [26] | 3-chloropropoxy | 4-(2-methoxyethyl) |

TABLE III-continued

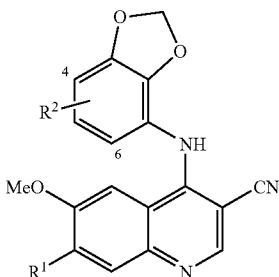

| Compound No. & Note | R¹ | R² |
|---|---|---|
| [27] | methoxy | 5-methyl |
| [28] | methoxy | 5-methoxymethyl |

Notes
[1] 4-Chloro-3-cyano-6,7-dimethoxyquinoline (International Patent Application WO 98/43960) was used as a starting material. The product gave the following characterising data;
NMR Spectrum: (DMSOd$_6$ and CF$_3$CO$_2$D) 4.02 (s, 3H), 4.05 (s, 3H), 6.12 (s, 2H), 7.0-7.1 (m, 3H), 7.45 (s, 1H), 8.12 (s, 1H), 9.15 (s, 1H);
Mass Spectrum: M + H⁺ 350.
[2] The product gave the following characterising data;
NMR Spectrum: (DMSOd$_6$ and CF$_3$CO$_2$D) 4.04 (s, 3H), 4.06 (s, 3H), 6.2 (d, 2H), 7.12 (d, 1H), 7.2 (d, 1H), 7.5 (s,1H), 8.15 (s, H), 9.2 (s, 1H);
Mass Spectrum: M + H⁺ 384 and 386.
[3] The product gave the following characterising data;
NMR Spectrum: (DMSOd$_6$ and CF$_3$CO$_2$D) 4.03 (s, 3H), 4.05 (s, 3H), 6.2 (s, 2H), 7.1 (d, 1H), 7.35 (d, 1H), 7.48 (s, 1H), 8.15 (s, 1H), 9.18 (s, 1H);
Mass Spectrum: M + H⁺ 428 and 430.
The 6-bromo-2,3-methylenedioxyaniline used as a starting material was prepared from 5-bromo-1,3-benzodioxole (Aldrich Chemical Company) using analogous procedures to those described in the portion of Example 1 above that is concerned with the preparation of 6-chloro-2,3-methylenedioxyaniline. There were thus obtained in turn:-
5-bromo-1,3-benzodioxole-4-carboxylic acid;
NMR Spectrum: (DMSOd$_6$ and CF$_3$CO$_2$D) 6.15 (s, 2H), 6.95 (d, 1H), 7.1 (d, 1H);
Mass Spectrum: [M − H]⁻ 243;
tert-butyl N-(5-bromo-1,3-benzodioxol-4-yl)carbamate;
NMR Spectrum: (DMSOd$_6$) 1.45 (s, 9H), 6.1 (s, 2H), 6.80 (d, 1H), 7.1 (d, 1H), 8.70 (s, 1H); and
6-bromo-2,3-methylenedioxyaniline;
NMR Spectrum: (DMSOd$_6$) 5.05 (s, 2H), 6.0 (s, 2H), 6.25 (d, 1H), 6.9 (d, 1H);
Mass Spectrum: M + H⁺ 216 and 218.
[4] The reaction product was purified by column chromatography on silica using increasingly polar mixtures of methylene chloride and a saturated methanolic ammonia solution as eluent. The material so obtained was dissolved in diethyl ether and a solution of hydrogen chloride in diethyl ether (1M, 2 ml) was added. The resultant solid was washed with diethyl ether to give the required product as a dihydrochloride salt which gave the following characterising data;
NMR Spectrum: (DMSOd$_6$ and CF$_3$CO$_2$D) 2.12 (m, 2H), 2.85 (s, 3H), 3.27-3.88 (m, 10H), 4.0 (s, 3H), 4.32 (t, 2H), 6.11 (s, 2H), 6.87 (m, 1H), 7.0 (m, 1H), 7.52 (s, 1H), 8.16 (s, 1H), 8.97 (s, 1H);
Mass Spectrum: M + H⁺ 494.
The 6-fluoro-2,3-methylenedioxyaniline used as a starting material was prepared as follows:-
A mixture of diisopropylamine (4.92 ml) and THF (100 ml) was cooled to −78° C. and n-butyllithium (2.5 M in THF, 14 ml) was added dropwise. The mixture was stirred at −70° C. for 30 minutes. 4-Fluoro-1,2-dimethoxybenzene (5 g) was added dropwise and the reaction mixture was stirred at −70° C. for 20 minutes. Dry carbon dioxide gas was bubbled into the reaction mixture for 15 minutes. The resultant reaction mixture was allowed to warm to ambient temperature and was stirred for a further hour. Water was added and the organic solvent was evaporated. The residue was acidified to pH2 by the addition of 2N aqueous hydrochloric acid solution and the mixture was extracted with a mixture of diethyl ether and ethyl acetate. The organic phase was dried over magnesium sulphate and evaporated. The solid so obtained was washed with pentane and dried under vacuum. There was thus obtained 6-fluoro-2,3-dimethoxybenzoic acid (3.4 g);
NMR Spectrum: (DMSOd$_6$) 3.8 (s, 3H), 3.85 (s, 3H), 7.0 (t, 1H), 7.15 (m, 1H).
A mixture of 6-fluoro-2,3-dimethoxybenzoic acid (14 g), concentrated aqueous hydrobromic acid (47%, 230 ml) and acetic acid (200 ml) was stirred and heated to 140° C. for 1 hour. The mixture was cooled to ambient temperature and partitioned between ethyl acetate and water. The organic phase was washed with water and with brine, dried over magnesium sulphate and evaporated to give 6-fluoro-2,3-dihydroxybenzoic acid (9.3 g);
NMR Spectrum: (DMSOd$_6$) 6.55 (t, 1H), 6.9 (m, 1H), 9.3 (br s, 2H).

TABLE III-continued

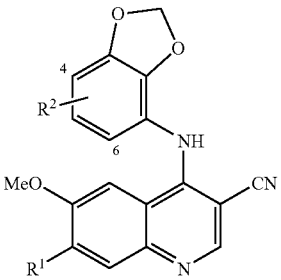

| Compound No. & Note | R¹ | R² |
|---|---|---|

Thionyl chloride (6 ml) was added dropwise to a solution of 6-fluoro-2,3-dihydroxybenzoic acid (9.3 g) in methanol (80 ml) that had been cooled to 0° C. The resultant mixture was stirred and heated to 60° C. for 24 hours. The mixture was evaporated and the residue was partitionned between ethyl acetate and a saturated aqueous sodium bicarbonate solution. The organic phase was washed with brine, dried over magnesium sulphate and evaporated. The residue was purified by column chromatography on silica eluting with increasingly polar mixtures of petroleum ether (b.p. 40-60° C.) and ethyl acetate as eluent. There was thus obtained methyl 6-fluoro-2,3-dihydroxybenzoate (7.2 g);
NMR Spectrum: (CDCl$_3$) 4.0 (s, 3H), 5.45 (s, 1H), 6.5 (t, 1H), 7.0 (m, 1H).
Potassium fluoride (11.2 g) was added to a solution of methyl 6-fluoro-2,3-dihydroxybenzoate (7.2 g) in DMF (110 ml) and the mixture was stirred and heated to 100° C. for 15 minutes. Diiodomethane (3.43 ml) was added and the mixture was stirred and heated to 100° C. for 75 minutes. The mixture was cooled to ambient temperature and partitioned between ethyl acetate and water. The organic layer was washed with brine, dried over magnesium sulphate and evaporated. The resultant residue was purified by colum chromatography on silica using increasingly polar mixtures of petroleum ether (b.p. 40-60° C.) and ethyl acetate as eluent. There was thus obtained methyl 6-fluoro-2,3-methylenedioxybenzoate (4.5 g);
NMR Spectrum: (DMSOd$_6$) 3.85 (s, 3H), 6.2 (s, 2H), 6.8 (m, 1H), 7.15 (m, 1H).
A suspension of the material so obtained, a 2N aqueous potassium hydroxide solution (23 ml) and methanol (60 ml) was stirred at ambient temperature for 3 hours. The mixture was evaporated and the residue was dissolved in water and the solution was acidified to pH2 by the addition of 6N aqueous hydrochloric acid. The resultant precipitate was isolated, washed with water and dried overnight under vacuum over phosphorus pentoxide. There was thus obtained 6-fluoro-2,3-methylenedioxybenzoic acid (4 g);
NMR Spectrum: (DMSOd$_6$) 6.15 (s, 2H), 6.75 (m, 1H), 7.05 (m, 1H).
The material so obtained was dissolved in 1,4-dioxane (60 ml) and anhydrous tert-butanol (17 ml), diphenylphosphoryl azide (5 ml) and triethylamine (3.8 ml) were added in turn. The resultant mixture was stirred and heated to 100° C. for 4.5 hours. The mixture was cooled to ambient temperature and filtered. The filtrate was evaporated and the resultant residue was partitioned between ethyl acetate and a 5% aqueous citric acid solution. The organic phase was washed in turn with water, a saturated aqueous sodium bicarbonate solution and brine, dried over magnesium sulphate and evaporated. There was thus obtained tert-butyl N-(5-fluoro-1,3-benzodioxol-4-yl)carbamate (4.5 g);
NMR Spectrum: (CDCl$_3$) 1.5 (s, 9H), 5.95 (br s, 1H), 6.0 (s, 2H), 6.55 (m, 2H).
A mixture of a portion (2.5 g) of the material so obtained, trifluoroacetic acid (15 ml) and methylene chloride (55 ml) was stirred at ambient temperature for 3.5 hours. The solvent was evaporated and the residue was partitioned between ethyl acetate and a saturated aqueous sodium bicarbonate solution. The organic phase was washed with brine, dried over magnesium sulphate and evaporated. There was thus obtained 6-fluoro-2,3-methylenedioxyaniline (1.1 g);
NMR Spectrum: (DMSOd$_6$) 5.0 (br s, 2H); 5.95 (s, 2H), 6.15 (m, 1H), 6.55 (m, 1H).
[5] The product gave the following characterising data;
NMR Spectrum: (CDCl$_3$) 2.1 (m, 2H), 2.28 (s, 3H), 2.4-2.6 (m, 8H), 2.55 (t, 2H), 3.78 (s, 3H), 4.24 (t, 2H), 5.97 (s, 2H), 6.64 (s, 1H), 6.72 (s, 1H), 6.97 (s, 1H), 7.4 (s, 1H), 8.63 (s, 1H);
Mass Spectrum: M + H$^+$ 554 and 556.
The 5-bromo-2,3-methylenedioxyaniline used as a starting material was prepared as follows:-
A mixture of 6-bromo-1,3-benzodioxole-4-carboxylic acid [Khim. Geterotsikl. Soedin 1979, 9, 1183-8 (Chemical Abstracts 92, 94280); 0.92 g], diphenylphosphoryl azide (1.08 g), tert-butanol (3 ml), triethylamine (0.34 g) and toluene (15 ml) were stirred and heated at 100° C. for 4 hours. The resultant mixture was evaporated and the residue was partitioned between methyl tert-butyl ether and a 5% aqueous citric acid solution. The organic phase was washed with water and a saturated aqueous sodium bicarbonate solution, dried over magnesium sulphate and evaporated. The residual oil was purified by column chromatography on silica using a 5:1 mixture of isohexane and ethyl acetate as eluent. There was thus obtained tert-butyl N-(6-bromo-1,3-benzodioxol-4-yl)carbamate (0.6 g);
NMR Spectrum: (CDCl$_3$) 1.52 (s, 9H), 5.95 (s, 2H), 6.39 (br s, 1H), 6.7 (d, 1H), 7.73 (br s, 1H).
A mixture of the material so obtained, trifluoroacetic acid (3 ml) and methylene chloride (8 ml) was stirred at ambient temperature for 1 hour. The solvent was evaporated and the residue was partitioned between methyl tert-butyl ether and a saturated aqueous sodium bicarbonate solution. The organic phase was washed with a saturated brine solution, dried over magnesium sulphate and evaporated. The residue was purified by column chromatography on silica using a 4:1 mixture of isohexane and ethyl acetate as eluent. There was thus obtained 5-bromo-2,3-methylenedioxyaniline (0.318 g) as a colourless solid;

TABLE III-continued

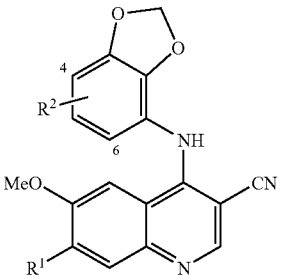

| Compound No. & Note | R¹ | R² |
|---|---|---|

NMR Spectrum: (CDCl₃) 3.6 (br s, 2H), 5.92 (s, 2H), 6.27 (m, 2H).

[6] The product gave the following characterising data;
NMR Spectrum: (DMSOd₆) 1.96 (m, 2H), 2.15 (s, H), 2.25-2.5 (m, 10H), 3.94 (s, 3H), 4.18 (t, 2H), 6.09 (s, 2H), 6.84 (d, 1H), 7.09 (d, 1H), 7.3 (s, 1H), 7.74 (s, 1H), 8.43 (s, 1H), 9.52 (s, 1H);
Mass Spectrum: M + H⁺ 554 and 556.

[7] 4-Chloro-3-cyano-6-methoxy-7-(3-morpholinopropoxy)quinoline (International Patent Application WO 00/68201, page 52) was used as a starting material. The reaction product was purified by column chromatography on silica using increasingly polar mixtures of methylene chloride and methanol as eluent. The material so obtained was dissolved in diethyl ether and a solution of hydrogen chloride in diethyl ether (1M) was added. The resultant solid was washed with diethyl ether to give the required product as a dihydrochloride salt which gave the following characterising data;
NMR Spectrum: (DMSOd₆ and CF₃CO₂D) 2.26-2.37 (m, 2H), 3.04-3.16 (m, 2H), 3.26-3.34 (t, 2H), 3.45-3.55 (m, 2H), 3.72-3.87 (m, 2H), 3.94-4.03 (m, 5H), 4.31 (t, 2H), 6.04 (s, 2H), 6.94-6.99 (m, 3H), 7.49 (s, 1H), 8.14 (s, 1H), 8.96 (s, 1H);
Mass Spectrum: M − H⁻ 461.

[8] The reaction mixture was stirred at 0° C. for 2 hours. The reaction product was purified by column chromatography on silica using increasingly polar mixtures of methylene chloride and a 7M solution of ammonia in methanol as eluent. The material so obtained was dissolved in ethyl acetate and a solution of hydrogen chloride in diethyl ether (1M, 1 ml) was added. The resultant solid was washed with diethyl ether to give the required product as a dihydrochloride salt which gave the following characterising data;
NMR Spectrum: (DMSOd₆) 2.81 (s, 3H), 3.0-3.63 (m, 10H), 4.05 (s, 3H), 4.42-4.57 (m, 2H), 5.39-5.52 (m, 1H), 6.08 (s, 2H), 6.96-7.1 (m, 3H), 7.61 (s, 1H), 8.29 (s, 1H), 9.03 (s, 1H), 11.30 (br s, 1H);
Mass Spectrum: M + H⁺ 494.

The 4-chloro-3-cyano-7-[(2S)-2-fluoro-3-(4-methylpiperazin-1-yl)propoxy]-6-methoxyquinoline used as a starting material was prepared as follows:-
A mixture of (2R)-3-benzyloxy-2-fluoropropyl chloride (0.4 g), 1-methylpiperazine (2.2 ml) and 2-methoxyethanol (5 ml) was stirred and heated to 80° C. for 12 hours and then to 110° C. for 6 hours. The resultant mixture was poured into a mixture of water (50 ml) and a saturated aqueous sodium chloride solution (50 ml) and extracted with ethyl acetate (3 × 25 ml). The organic extracts were dried over magnesium sulphate and evaporated. The residue was purified by column chromatography on silica using increasingly polar mixtures of methylene chloride and a 7N solution of ammonia in methanol as eluent. There was thus obtained benzyl (2S)-2-fluoro-3-(4-methylpiperazin-1-yl)propyl ether as an oil (0.27 g);
NMR Spectrum: (CDCl₃) 2.28 (s, 3H), 2.33-2.75 (m, 10H), 3.61-3.68 (m, 2H), 4.58 (s, 2H), 4.73-4.91 (m, 1H), 7.28-7.38 (m, 5H).
The material so obtained was dissolved in methanol (10 ml) and 10% palladium-on-carbon (0.77 g) and ammonium formate (0.65 g) were added and the mixture was heated to reflux for 5 hours. A further portion of ammonium formate (0.7 g) was added and the mixture was heated to reflux for 12 hours. The mixture was allowed to cool to ambient temperature and filtered. The filtrate was evaporated and the crude product so obtained was purified by column chromatography on silica using increasingly polar mixtures of methylene chloride and a 7N solution of ammonia in methanol as eluent. There was thus obtained (2S)-2-fluoro-3-(4-methylpiperazin-1-yl)propan-1-ol as an oil (0.082 g);
NMR Spectrum: (CDCl₃) 2.28 (s, 3H), 2.3-2.71 (m, 8H), 2.74 (d, 1H), 2.79 (m, 1H), 3.84 (t, 1H), 3.89 (d, 1H), 4.59-4.75 (m, 1H);
Mass Spectrum: M + H⁺ 177.
Using an analogous procedure to that described in Example 8, (2S)-2-fluoro-3-(4-methylpiperazin-1-yl)propan-1-ol (0.082 g) was reacted with 4-chloro-3-cyano-7-hydroxy-6-methoxyquinoline (0.14 g) to give 4-chloro-3-cyano-7-[(2S)-2-fluoro-3-(4-methylpiperazin-1-yl)propoxy]-6-methoxyquinoline.

[9] The product gave the following characterising data;
NMR Spectrum: (DMSOd₆) 3.77 (s, 3H), 3.81 (s, 3H), 5.88 (s, 2H), 6.3 (d, 1H), 6.87 (d, 1H), 6.93 (s, 1H), 7.7 (s, 1H), 7.83 (s, 1H);

TABLE III-continued

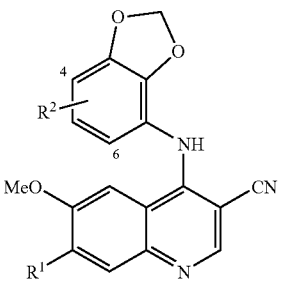

| Compound No. & Note | R¹ | R² |
| --- | --- | --- |

Mass Spectrum: M + H⁺ 476.
The 4-iodo-2,3-methylenedioxyaniline used as a starting material was prepared as follows:-
Benzyltrimethylammonium dichloroiodate (2.8 g) was added portionwise during 10 minutes to a stirred mixture of 2,3-methylenedioxyaniline (1 g), calcium carbonate (0.95 g), methanol (5 ml) and methylene chloride (10 ml). The reaction mixture was stirred at ambient temperature for 1.5 hours. The resultant mixture was diluted with water and extracted with methylene chloride. The organic phase was washed with water and with a saturated brine solution, dried over magnesium sulphate and evaporated. The residue was purified by column chromatography on silica using increasingly polar mixtures of isohexane and methylene chloride as eluent. There was thus obtained 4-iodo-2,3-methylenedioxyaniline as a solid (1.1 g);
NMR Spectrum: (DMSOd₆) 5.04 (br s, 2H), 5.94 (s, 2H), 6.13 (d, 1H), 6.8 (d, 1H).
[10] The product gave the following characterising data;
NMR Spectrum: (DMSOd₆) 4.0 (s, 6H), 6.18 (s, 2H), 7.38 (s, 1H), 7.48 (s, 1H), 7.88 (s, 1H), 8.44 (s, 1H), 9.45 (s, 1H);
Mass Spectrum: M + H⁺ 510.
The 6-chloro-4-iodo-2,3-methylenedioxyaniline used as a starting material was prepared by the reaction of 6-chloro-2,3-methylenedioxyaniline and benzyltrimethylammonium dichloroiodate in an analogous manner to that described in Note [9] immediately above. The material so obtained gave the following characterising data;
NMR Spectrum: (DMSOd₆) 6.04 (s, 2H), 7.0 (s, 1H).
[11] The required 6-iodo-2,3-methylenedioxyanilino product was obtained as the major portion of a 4:1 mixture, the minor portion being the 4,6-diiodo-2,3-methylenedioxyanilino compound. The mixture of materials gave the following characterising data;
NMR Spectrum: (DMSOd₆) 3.98 (s, 6H), 6.09 (s, 2H), 6.87 (d, 1H), 7.34 (s, 1H), 7.47 (d, 1H), 7.89 (s, 1H), 8.41 (s, 1H), 9.42 (s, 1H);
Mass Spectrum: M + H⁺ 476 and 602.
The 4:1 mixture of 6-iodo-2,3-methylenedioxyaniline and 4,6-diiodo-2,3-methylenedioxyaniline used as a starting material was prepared as follows:-
Benzyltrimethylammonium dichloroiodate (12 g) was added portionwise during 20 minutes to a stirred mixture of 2,3-methylenedioxyaniline (4 g), calcium carbonate (3.77 g), methanol (20 ml) and methylene chloride (40 ml). The reaction mixture was stirred at ambient temperature for 1 hour. The resultant mixture was diluted with water and extracted with methylene chloride. The organic phase was washed with water and with a saturated brine solution, dried over magnesium sulphate and evaporated. The residue was purified by column chromatography on silica using increasingly polar mixtures of isohexane and methylene chloride as eluent. There was thus obtained 4-iodo-2,3-methylenedioxyanhline (2.7 g) and a 4:1 mixture (1.6 g) of 4-iodo-2,3-methylenedioxyaniline and 4,6-diiodo-2,3-methylenedioxyaniline;
NMR Spectrum: (DMSOd₆) 6.03 (s, 2H), 7.33 (s, 1H).
[12] The product gave the following characterising data;
NMR Spectrum: (DMSOd₆) 3.96 (s, 3H), 3.97 (s, 3H), 6.08 (s, 2H), 6.83 (s, 1H), 7.08 (s, 1H), 7.3 (s, 1H), 7.75 (s, 1H), 8.43 (s, 1H), 9.5 (s, 1H);
Mass Spectrum: M + H⁺ 428 and 430.
[13] The product gave the following characterising data;
NMR Spectrum: (CDCl₃) 3.83 (s, 3H), 4.05 (s, 3H), 5.98 (s, 2H), 6.76 (d, 1H), 6.84 (d, 1H), 6.9 (br s, 1H), 7.06 (s, 1H), 7.39 (s, 1H), 8.64 (s, 1H);
Mass Spectrum: M + H⁺ 428 and 430.
[14] The product gave the following characterising data;
NMR Spectrum: (CDCl₃) 3.81 (s, 3H), 4.05 (s, 3H), 5.96 (s, 2H), 6.3 (m, 1H), 6.5 (m, 1H), 6.64 (br s, 1H), 7.01 (s, 1H), 7.4 (s, 1H), 8.65 (s, 1H);
Mass Spectrum: M + H⁺ 368.
The 5-fluoro-2,3-methylenedioxyaniline used as a starting material was prepared as follows:-
A mixture of 5-bromo-2,3-methylenedioxyaniline (2.0 g), 1,2-bis(chlorodimethylsilyl)ethane (2.09 g), triethylamine (1.96 g) and methylene dichloride (50 ml) was stirred at ambient temperature for 88 hours. The resultant mixture was washed with a 5% aqueous sodium dihydrogen phosphate solution, dried over magnesium sulphate and evaporated. The oil so obtained was purified by column chromatography on neutral alumina using isohexane as eluent. There was thus obtained N-(5-bromo-2,3-methylenedioxyphenyl)-2,2,5,5-tetramethyl-1,2,5-azadisilolidine as an oil (2.4 g);

TABLE III-continued

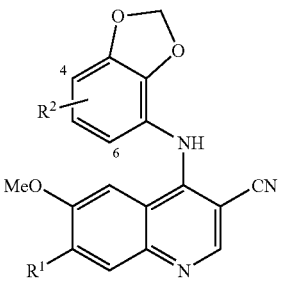

| Compound No. & Note | R¹ | R² |
|---|---|---|

NMR Spectrum: (CDCl₃) 0.13 (s, 12H), 0.86 (s, 4H), 5.87 (s, 2H), 6.59 (d, 1H), 6.67 (d, 1H).

n-Butyllithium (1.6 M in THF, 1.1 ml) was added to a solution of N-(5-bromo-2,3-methylenedioxyphenyl)-2,2,5,5-tetramethyl-1,2,5-azadisiolidine (0.6 g) in THF (10 ml) that had been cooled to −70° C. and the mixture was stirred at −70° C. for 1 hour. A solution of N-fluorobenzenesulphonimide (1.0 g) in THF (3 ml) was added and the mixture was allowed to warm to 0° C. over 3 hours. The mixture was stirred at 0° C. for a further hour. The mixture was poured into a cooled 1N aqueous hydrochloric acid solution and stirred for 5 minutes and extracted with diethyl ether. The aqueous phase was basified with a 40% aqueous sodium hydroxide solution and extracted with diethyl ether. The organic phase was washed with a saturated brine solution, dried over magnesium sulphate and evaporated. There was thus obtained 5-fluoro-2,3-methylenedioxyaniline as an oil (0.12 g) which was used without further purification.

[15] The reactants were 4-chloro-3-cyano-6,7-dimethoxyquinoline (0.082 g) and 4-tert-butyldimethylsilyloxymethyl-2,3-methylenedioxyaniline (0.1 g) and the initial product was 4-(4-tert-butyldimethylsilyloxymethyl-2,3-methylenedioxyanilino)-3-cyano-6,7-dimethoxyquinoline (0.115 g) which gave the following characterising data;

NMR Spectrum: (DMSOd₆) 0.1 (s, 6H), 0.94 (s, 9H), 3.71 (s, 3H), 4.03 (s, 3H), 4.72 (s, 2H), 5.95 (s, 2H), 6.63 (d, 1H), 6.7 (s, 1H), 6.94 (d, 1H), 6.99 (s, 1H), 7.38 (s, 1H), 8.62 (s, 1H);

Mass Spectrum: M + H⁺ 494.

A solution of that material (0.38 g) in THF (6 ml) was treated with tetra-n-butylammonium fluoride (1M solution in THF; 1.5 ml) at ambient temperature for 5 hours. The reaction mixture was partitioned between ethyl acetate and a saturated aqueous ammonium chloride solution. The organic layer was separated, dried over magnesium sulphate and evaporated. The residue was purified by column chromatography on silica using increasingly polar mixtures of hexane and ethyl acetate as eluent. The product so obtained was triturated under diethyl ether. There was thus obtained the required product as a solid (0.197 g);

NMR Spectrum: (DMSOd₆) 3.92 (d, 6H), 4.48 (d, 2H), 5.2 (t, 1H), 5.98 (s, 2H), 6.83 (d, 1H), 6.95 (d, 1H), 7.3 (s, 1H), 7.78 (s, 1H), 8.41 (s, 1H), 9.48 (s, 1H);

Mass Spectrum: M + H⁺ 380.

The 4-tert-butyldimethylsilyloxymethyl-2,3-methylenedioxyaniline used as a starting material was prepared as follows:-

A mixture of 2,3-dihydroxy-4-nitrobenzaldehyde (J. Med. Chem., 1992, 35, 4584-4588; 7.4 g), bromochloromethane (12.7 ml), caesium carbonate (25.4 g) and DMF (95 ml) was stirred and heated to 110° C. for 3 hours. A further portion of bromochloromethane (6.0 ml) was added and the mixture was further heated to 110° C. for 3 hours. A third portion of bromochloromethane (3.0 ml) was added and the mixture was further heated to 110° C. for 1 hour. The mixture was poured into 2N aqueous hydrochloric acid solution (500 ml) and stirred for 15 minutes. Ethyl acetate (500 ml) was added and the mixture was filtered. The organic layer was washed with a saturated brine solution, dried over magnesium sulphate and evaporated. The crude product was purified by column chromatography on silica using a 1:1 mixture of isohexane and ethyl acetate as eluent. There was thus obtained 2,3-methylenedioxy-4-nitrobenzaldehyde as a yellow solid (5.3 g);

NMR Spectrum: (DMSOd₆) 6.49 (s, 2H), 7.37 (d, 1H), 7.64 (d, 1H), 10.10 (br s, 1H).

Sodium borohydride (0.75 g) was added portionwise to an ice-cooled mixture of 2,3-methylenedioxy-4-nitrobenzaldehyde (1.3 g) in methanol (35 ml) and the resultant mixture was stirred for 2 hours and allowed to warm to ambient temperature. The mixture was partitioned between ethyl acetate and a 2N aqueous hydrochloric acid solution. The organic layer was dried over magnesium sulphate and evaporated. There was thus obtained 2,3-methylenedioxy-4-nitrobenzyl alcohol as a solid (0.93 g);

NMR Spectrum: (CDCl₃) 4.67 (d, 2H), 5.43 (t, 1H), 6.18 (s, 2H), 6.96 (d, 1H), 7.57 (d, 1H).

tert-Butyldimethylsilyl chloride (0.462 g) was added to a mixture of 2,3-methylenedioxy-4-nitrobenzyl alcohol (0.55 g), triethylamine (0.47 g), N N-dimethylaminopyridine (0.01 g) and DMF (5 ml) and the mixture was stirred at ambient temperature for 2 hours. The resultant mixture was evaporated and the residue was partitioned between ethyl acetate and a dilute aqueous citric acid solution. The organic layer was dried over magnesium sulphate and evaporated. The residue was purified by column chromatography on silica using increasingly polar mixtures of hexane and ethyl acetate as eluent. There was thus obtained tert-butyldimethylsilyl 2,3-methylenedioxy-4-nitrobenzyl ether as a solid (0.68 g);

TABLE III-continued

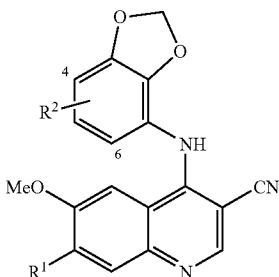

Compound
No. & Note  R¹                                        R²

NMR Spectrum: (CDCl₃) 0.1 (s, 6H), 0.95 (s, 9H), 4.74 (s, 2H), 6.22 (s, 2H), 7.08 (d, 1H), 7.62 (d, 1H).
The material so obtained was added to a stirred mixture of hydrazine hydrate (0.36 ml). Raney nickel (50% dispersion in water; 0.18 g) and methanol (24 ml) and the reaction mixture was stirred at ambient temperature for 0.5 hours. The mixture was filtered and the filtrate was evaporated. The residue was purified by column chromatography on silica using increasingly polar mixtures of hexane and ethyl acetate as eluent. There was thus obtained 4-tert-butyldimethylsilyloxymethyl-2,3-methylenedioxyaniline as an oil (0.56 g);
NMR Spectrum: (CDCl₃) 0.1 (s, 6H), 0.92 (s, 9H), 3.52 (br s, 2H), 4.62 (s, 2H), 5.92 (s, 2H), 6.31 (d, 1H), 6.73 (d, 1H).
[16] The product gave the following characterising data;
NMR Spectrum: (DMSOd₆) 2.18 (s, 3H), 3.93 (2 s, 6H), 5.97 (s, 2H), 6.76 (s, 2H), 7.3 (s, 1H), 7.78 (s, 1H), 8.4 (s, 1H), 9.44 (s, 1H);
Mass Spectrum: M + H⁺ 364.
The 4-methyl-2,3-methylenedioxyaniline used as a starting material was prepared as follows:-
A mixture of 2,3-methylenedioxy-4-nitrobenzyl alcohol (0.35 g), isopropyl isocyanate (2 ml), toluene (2 ml) and acetonitrile (2 ml) was heated to 70° C. for 12 hours. The mixture was evaporated and the residue was triturated under hexane. There was thus obtained 2,3-methylenedioxy-4-nitrobenzyl N-isopropylcarbamate as a solid (0.37 g);
NMR Spectrum: (CDCl₃) 1.18 (d, 6H), 3.83 (m, 1H), 4.6 (br s, 1H), 5.12 (s, 2H), 6.25 (s, 2H), 6.95 (d, 1H), 7.59 (d, 1H).
A mixture of a portion (0.2 g) of the material so obtained, 10% palladium-on-carbon catalyst (0.05 g) and ethyl acetate (5 ml) was stirred under an atmosphere pressure of hydrogen for 12 hours. The mixture was filtered and the filtrate was evaporated. There was thus obtained 4-methyl-2,3-methylenedioxyaniline as an oil (0.089 g);
NMR Spectrum: (CDCl₃) 2.13 (s, 3H), 3.45 (br s, 2H), 5.91 (s, 2H), 6.23 (d, 1H), 6.51 (d, 1H).
[17] The product gave the following characterising data;
NMR Spectrum: (CDCl₃) 3.52 (s, 3H), 3.93 (s, 2H), 4.0 (s, 3H), 5.93 (s, 2H), 6.6 (d, 1H), 6.66 (s, 1H), 6.67 (d, 1H), 6.9 (s, 1H), 7.28-7.3 (m, 5H), 7.34 (s, 1H), 8.6 (s, 1H);
Mass Spectrum: M + H⁺ 440.
The 4-benzyl-2,3-methylenedioxyaniline used as a starting material was prepared as follows:-
A mixture of 4-iodo-2,3-methylenedioxyaniline (3.0 g), 1,2-bis(chlorodimethylsilyl)ethane (2.57 g), triethylaniline (2.33 g) and methylene dichloride (60 ml) was stirred at ambient temperature for 88 hours. The resultant mixture was evaporated. Isohexane was added to the residue and the mixture was filtered. The filtrate was evaporated and the resultant residue was purified by column chromatography on neutral alumina using isohexane as eluent. There was thus obtained N-(4-iodo-2,3-methylenedioxyphenyl)-2,2,5,5-tetramethyl-1,2,5-azadisilolidine as a solid (2.85 g);
NMR Spectrum: (CDCl₃) 0.1 (s, 12H), 0.82 (s, 4H), 5.9 (s, 2H); 6.26 (d, 1H), 6.98 (d, 1H).
n-Butyllithium (1.6M in THF, 1.35 ml) was added to a solution of N-(4-iodo-2,3-methylenedioxyphenyl)-2,2,5,5-tetramethyl-1,2,5-azadisilolidine (0.8 g) in THF (12 ml) that had been cooled to −70° C. and the mixture was stirred at −70° C. for 30 minutes. Benzaldehyde (0.23 g) was added and the mixture was stirred at −70° C. for 2 hours and then allowed to warm to 0° C. The resultant mixture was poured into a cooled 1N aqueous hydrochloric acid solution and stirred for 5 minutes and extracted with diethyl ether. The aqueous phase was basified with a 40% aqueous sodium hydroxide solution and extracted with diethyl ether. The organic phase was washed with a saturated brine solution, dried over magnesium sulphate and evaporated. The material so obtained was purified by column chromatography on silica using a 1:4 mixture of isohexane and tert-butyl methyl ether as eluent. There was thus obtained 4-(α-hydroxybenzyl)-2,3-methylenedioxyaniline as an oil (0.213 g);
NMR Spectrum: (CDCl₃) 2.4 (s, 1H), 3.54 (br s, 2H), 5.9 (s, 1H), 5.92 (s, 2H), 6.26 (d, 1H), 6.6 (d, 1H), 7.25 (m, 1H), 7.32 (t, 2H), 7.4 (d, 2H).
A mixture of the material so obtained, 10% palladium-on-carbon catalyst (0.02 g) and ethanol (10 ml) was stirred at ambient temperature under an atmosphere pressure of hydrogen for 12 hours. The mixture was filtered and the residue was evaporated. There was thus obtained 4-benzyl-2,3-methylenedioxyaniline as a colourless oil (0.137 g);
Mass Spectrum: M + H⁺ 228.
[18] The product gave the following characterising data;
NMR Spectrum: (CDCl₃) 2.48 (s, 3H), 3.75 (s, 3H), 4.03 (s, 3H), 6.0 (s, 2H), 6.61 (d, 1H), 6.66 (br s, 1H), 6.82 (d, 1H), 6.98 (s, 1H), 7.38 (s, 1H), 8.62 (s, 1H);

TABLE III-continued

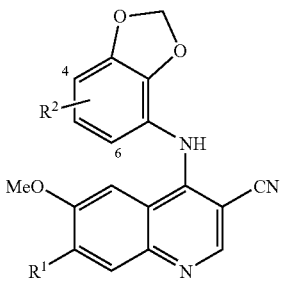

| Compound No. & Note | R¹ | R² |
|---|---|---|

Mass Spectrum: M + H⁺ 396.
The 4-methylthio-2,3-methylenedioxyaniline used as a starting material was prepared as follows:-
n-Butyllithium (1.6 M in hexane, 1.28 ml) was added during 10 minutes to a solution of N-(4-iodo-2,3-methylenedioxyphenyl)-2,2,5,5-tetramethyl-1,2,5-azadisilolidine (0.75 g) in THF (25 ml) that had been cooled to −78° C. and the mixture was stirred at −78° C. for 25 minutes. Dimethyl disulphide (0.288 g) was added and the mixture was stirred at −78° C. for 3 hours. The resultant mixture was allowed to warm to 0° C. A 1N aqueous hydrochloric acid solution (25 ml) was added and the mixture was stirred for 10 minutes. The mixture was washed with diethyl ether. The aqueous phase was basified to pH11 by the addition of a concentrated aqueous sodium hydroxide solution and extracted with methylene chloride. The organic extract was washed with a saturated aqueous sodium chloride solution, dried over magnesium sulphate and evaporated. The material so obtained was purified by column chromatography on reverse-phase silica using a decreasingly polar gradient of acetonitrile in water (plus 0.1% trifluoroacetic acid) as eluent. There was thus obtained 4-methylthio-2,3-methylenedioxyaniline as an oil which crystallized on standing (0.13 g);
NMR Spectrum: (CDCl₃) 2.38 (s, 3H), 3.59 (br s, 2H), 5.98 (s, 2H), 6.27 (d, 1H), 6.74 (d, 1H).
[19] The product gave the following characterising data;
NMR Spectrum: (DMSOd₆) 1.96 (m, 2H), 2.18 (s, 3H), 2.25-2.5 (m, 10H), 3.94 (s, 3H), 4.22 (t, 2H), 6.11 (s, 2H), 6.76 (d, 1H), 7.22 (d, 1H), 7.35 (s, 1H), 7.75 (s, 1H), 8.48 (s, 1H), 9.54 (s, 1H);
Mass Spectrum: M − H⁻ 600.
The 4-chloro-3-cyano-6-methoxy-7-[3-(4-methylpiperazin-1-yl)propoxy]quinoline used as a starting material was prepared as follows:-
A solution of diisopropyl azodicarboxylate (12.1 ml) in methylene chloride (50 ml) was added dropwise during 30 minutes to a stirred mixture of 4-chloro-3-cyano-7-hydroxy-6-methoxyquinoline (12 g), 1-(3-hydroxypropyl)-4-methylpiperazine (9.7 g), triphenylphosphine (16.1 g) and methylenedichloride (200 ml) that had been cooled to 5° C. The resultant mixture was allowed to warm to ambient temperature and was then stirred for 1 hour. Further portions of diisopropyl azodicarboxylate (1.2 ml) and triphenylphosphine (1.6 g) were added and the mixture was stirred at ambient temperature for a further 1 hour. The mixture was poured into water and the organic layer was separated, washed with a saturated brine solution, dried over magnesium sulphate and evaporated. The material so obtained was purified by column chromatography on silica using increasingly polar mixtures of methylene chloride and methanol as eluent. There was thus obtained the required starting material as a solid (14.5 g);
NMR Spectrum: (DMSOd₆) 1.95 (m, 2H), 2.13 (s, 3H), 2.24-2.5 (m, 10H), 4.0 (s, 3H), 4.25 (t, 2H), 7.43 (s, 1H), 7.51 (s, 1H), 8.95 (s, 1H);
Mass Spectrum: M + H⁺ 375 and 377.
[20] The product gave the following characterising data;
NMR Spectrum: (CDCl₃) 2.88 (m, 2H); 3.37 (s, 3H), 3.62 (t, 2H), 3.72 (s, 3H), 4.03 (s, 3H), 5.93 (s, 2H), 6.64 (d, 1H), 6.68 (s, 1H), 6.76 (d, 1H), 6.95 (s, 1H), 7.37 (s, 1H), 8.61 (s, 1H);
Mass Spectrum: M + H⁺ 408.
The 4-(2-methoxyethyl)-2,3-methylenedioxyaniline used as a starting material was prepared as follows:-
Potassium tert-butoxide (1M solution in THF; 1.35 ml) was added to a mixture of methoxymethyltriphenylphosphonium chloride (0.42 g) and THF (3 ml) and the resultant mixture was stirred at ambient temperature for 0.5 hours. A solution of 2,3-methylenedioxy-4-nitrobenzaldehyde (0.12 g) in THF (2 ml) was added and the reaction mixture was stirred at ambient temperature for 1 hour. The mixture was diluted with a saturated aqueous ammonium chloride solution and extracted with ethyl acetate. The organic phase was dried over magnesium sulphate and evaporated. The residue was purified by column chromatography on silica using increasingly polar mixtures of methylene chloride and ethyl acetate as eluent. There was thus obtained 4-(2-methoxyethenyl)-2,3-methylenedioxy-1-nitrobenzene as a solid (0.108 g) in the form of a 2.7:1 mixture of Z and E isomers;
NMR Spectrum: (CDCl₃) 3.77 (s, 3H), 5.72 (d, 1H), 6.24 (s, 2H), 6.74 (d, 1H), 7.48 (d, 1H), 7.56 (d, 1H).
A mixture of the material so obtained, 10% palladium-on-carbon (0.02 g) and ethyl acetate (4 ml) was stirred under an atmosphere pressure of hydrogen at ambient temperature for 12 hours. The mixture was filtered and the filtrate was evaporated. The residue was purified by column chromatography on silica using increasingly polar mixtures of hexane and ethyl acetate as eluent. There was thus obtained 4-(2-methoxyethyl)-2,3-methylenedioxyaniline as an oil (0.05 g);

TABLE III-continued

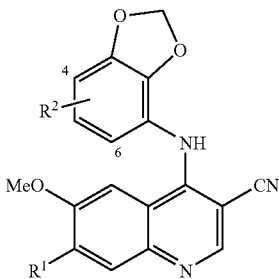

| Compound No. & Note | R¹ | R² |
|---|---|---|

NMR Spectrum: (CDCl₃) 2.78 (t, 2H), 3.36 (s, 3H), 3.48 (br s, 2H), 3.57 (t, 2H), 5.92 (s, 2H), 6.27 (d, 1H), 6.54 (d, 1H).
[21] The product gave the following characterising data;
NMR Spectrum: (CDCl₃) 2.49 (t, 4H), 3.5 (s, 2H), 3.71 (t, 4H), 3.76 (s, 3H), 4.03 (s, 3H), 5.94 (s, 2H), 6.64 (d, 1H), 6.74 (s, 1H), 6.86 (d, 1H), 7.02 (s, 1H), 7.37 (s, 1H), 8.61 (s, 1H);
Mass Spectrum: M − H⁻ 447.
The 2,3-methylenedioxy-4-morpholinomethylaniline used as a starting material was prepared as follows:-
Sodium triacetoxyborohydride (1.06 g) was added to a stirred mixture of 2,3-methylenedioxy-4-nitrobenzaldehyde (0.7 g), morpholine (0.34 g), acetic acid (0.23 ml) and THF (20 ml) and the resultant mixture was stirred at ambient temperature for 3 hours. The mixture was partitioned between ethyl acetate and a saturated aqueous sodium bicarbonate solution. The organic phase was dried over magnesium sulphate and evaporated. The residue was purified by column chromatography on silica using increasingly polar mixtures of methylene chloride and a saturated methanolic ammonia solution as eluent. There was thus obtained 2,3-methylenedioxy-4-morpholinomethyl-1-nitrobenzene as a solid (0.62 g);
NMR Spectrum: (CDCl₃) 2.5 (t, 4H), 3.66 (s, 2H), 3.72 (t, 4H), 6.22 (s, 2H), 7.02 (d, 1H), 7.59 (d, 1H).
2,3-Methylenedioxy-4-morpholinomethyl-1-nitrobenzene (0.1 g) was added to a stirred mixture of Raney nickel (50% in water, 0.03 g), hydrazine hydrate (0.074 g) and methanol (4 ml) and the mixture was stirred at ambient temperature for 1.5 hours. The mixture was filtered and the filtrate was evaporated. The residue was purified by column chromatography on silica-using increasingly polar mixtures of methylene chloride and ethyl acetate as eluent. There was thus obtained 2,3-methylenedioxy-4-morpholinomethylaniline (0.085 g);
NMR Spectrum: (CDCl₃) 2.49 (t, 4H), 3.43 (s, 2H), 3.71 (t, 4H), 5.95 (s, 2H), 6.28 (d, 1H), 6.66 (d, 1H).
[22] The product gave the following characterising data;
NMR Spectrum: (CDCl₃) 2.26 (s, 6H), 3.46 (s, 2H), 3.74 (s, 3H), 4.04 (s, 3H), 5.97 (s, 2H), 6.63 (d, 1H), 6.68 (s, 1H), 6.82 (d, 1H), 7.01 (s, 1H), 7.37 (s, 1H), 8.62 (s, 1H);
Mass Spectrum: M − H⁻ 405.
The 4-dimethylaminomethyl-2,3-methylenedioxyaniline used as a starting material was prepared from 2,3-methylenedioxy-4-nitrobenzaldehyde and dimethylamine using analogous procedures to those decribed in Note [21] immediately above. The required starting material gave the following characterising data;
NMR Spectrum: (CDCl₃) 2.24 (s, 6H), 3.35 (s, 2H), 3.51 (br s, 2H), 5.95 (s, 2H), 6.28 (d, 1H), 6.60 (d, 1H).
[23] The product gave the following characterising data;
NMR Spectrum: (DMSOd₆) 3.98 (s, 6H), 6.17 (s, 2H), 6.97 (d, 1H), 7.27 (d, 1H), 7.35 (s, 1H), 7.46 (s, 1H), 7.78 (s, 1H), 8.5 (d, 2H), 9.64 (s, 1H);
Mass Spectrum: M + H⁺ 417.
The 2,3-methylenedioxy-4-oxazol-5-ylaniline used as a starting material was prepared as follows:-
A mixture of 2,3-methylenedioxy-4-nitrobenzaldehyde (0.1 g), tosylmethyl isocyanide (0.109 g), potassium carbonate (0.078 g) and methanol (5 ml) was stirred and heated to 50° C. for 1 hour. The mixture was partitioned between methylene chloride and water. The organic phase was dried over magnesium sulphate and evaporated. There was thus obtained 2,3-methylenedioxy-4-oxazol-5-yl-1-nitrobenzene as a solid (0.13 g);
NMR Spectrum: (DMSOd₆) 6.48 (s, 2H), 7.35 (d, 1H), 7.7 (m, 2H), 8.63 (s, 1H).
A mixture of the material so obtained, 10% palladium-on-carbon (0.03 g), methanol (1 ml) and ethyl acetate (3 ml) was stirred at ambient temperature under an atmosphere pressure of hydrogen for 12 hours. The mixture was filtered and the filtrate was evaporated. There was thus obtained 2,3-methylenedioxy-4-oxazol-5-ylaniline as a solid (0.048 g);
NMR Spectrum: (CDCl₃) 5.18 (s, 2H), 6.08 (s, 2H), 6.35 (d, 1H), 6.93 (d, 1H), 7.14 (s, 1H), 8.28 (s, 1H).
[24] The product gave the following characterising data;
NMR Spectrum: (DMSOd₆) 1.96 (m, 2H), 2.15 (s, 3H), 2.4-2.72 (m, 10H), 2.79 (t, 2H), 3.22 (s, 3H), 3.51 (t, 2H), 3.91 (s, 3H), 4.19 (t, 2H), 5.98 (s, 2H), 6.79 (m, 2H), 7.3 (s, 1H), 7.74 (s, 1H), 8.4 (s, 1H), 9.45 (s, 1H);
Mass Spectrum: M − H⁻ 532.
[25] The product gave-the following characterising data;
NMR Spectrum: (DMSOd₆) 1.98 (m, 2H), 2.68 (t, 2H), 2.83 (t, 2H), 2.93 (br s, 4H), 3.1 (br s, 4H), 3.28 (s, 3H), 3.57 (t, 2H), 3.96 (s, 3H), 4.03 (t, 2H), 5.99 (s, 2H), 6.81 (m, 2H), 7.36 (s, 1H), 7.78 (s, 1H), 8.43 (s, 1H), 9.45 (s, 1H);

TABLE III-continued

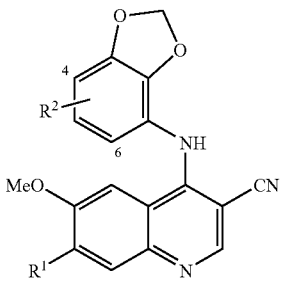

| Compound No. & Note | R$^1$ | R$^2$ |
|---|---|---|

Mass Spectrum: M + H$^+$ 569.
The 4-chloro-3-cyano-7-[3-(1,1-dioxotetrahydro-4H-thiazin-4-yl)propoxy]-6-methoxyquinoline used as a starting material was prepared as follows:-
A mixture of 3-aminopropan-1-ol (0.65 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 4-(3-hydroxypropyl)-1,1-dioxotetrahydro-4H-thiazine (0.8 g); NMR Spectrum: (CDCl$_3$) 1.7-1.8 (m, 2H), 2.73. (t, 2H), 3.06 (br s, 8H), 3.25 (s, 1H), 3.78 (t, 2H);
Mass Spectrum: M + H$^+$ 194.
Diethyl azodicarboxylate (1.72 g) was added dropwise to a suspension of 4-chloro-3-cyano-7-hydroxy-6-methoxyquinoline (1 g), 4-(3-hydroxypropyl)-1,1-dioxotetrahydro-4H-thiazine (1.23 g), triphenylphosphine (1.45 g) and methylene chloride (10 ml) and the mixture was stirred at ambient temperature for 16 hours. The resultant mixture was washed with water and with a saturated brine solution. The organic phase was dried over magnesium sulphate and evaporated. The residue was purified by column chromatography on silica using increasingly polar mixtures of methylene chloride, ethyl acetate and a saturated methanolic ammonia solution as eluent. The material so obtained was triturated under diethyl ether. There was thus obtained 4-chloro-3-cyano-7-[3-(1,1-dioxotetrahydro-4H-thiazin-4-yl)propoxy]-6-methoxyquinoline (0.15 g);
NMR Spectrum: (DMSOd$_6$) 1.96 (m, 2H), 2.64 (t, 2H), 2.88-2.93 (m, 4H), 3.07-3.12 (m, 4H), 4.0 (s, 3H), 4.29 (t, 2H), 7.44 (s, 1H), 7.55 (s, 1H), 8.96 (s, 1H);
Mass Spectrum: M + H$^+$ 410.
[26] The product gave the following characterising data;
NMR Spectrum: (DMSOd$_6$) 2.25 (m, 2H), 2.78 (t, 2H), 3.25 (s, 3H), 3.54 (t, 2H), 3.81 (t, 2H), 3.93 (s, 3H), 4.28 (t, 2H), 5.97 (s, 2H), 6.78 (m, 2H), 7.33 (s, 1H), 7.77 (s, 1H), 8.39 (s, 1H), 9.42 (s, 1H);
Mass Spectrum: M + H$^+$ 470.
[27] The product gave the following characterising data;
NMR Spectrum: (CDCl$_3$) 2.25 (s, 3H), 3.74 (s, 3H), 4.02 (s, 3H), 5.9 (s, 2H), 6.45 (d, 1H), 6.56 (d, 1H), 6.78 (br s, 1H), 7.02 (s, 1H), 7.36 (s, 1H), 8.6 (s, 1H);
Mass Spectrum: M + H$^+$ 364.
The 5-methyl-2,3-methylenedioxyaniline used as a starting material was prepared as follows:-
n-Butyllithium (1.6 M in hexane; 1.1 ml) was added dropwise to a solution of N-(5-bromo-2,3-methylenedioxyphenyl)-2,2,5,5-tetramethyl-1,2,5-azadisilolidine (0.6 g) in THF (12 ml) that had been cooled to −70° C. and the mixture was stirred at −70° C. for 1 hour. Methyl iodide (0.285 g) was added and the mixture was stirred and allowed to warm to 0° C. during 2 hours. A 1N aqueous hydrochloric acid solution was added and the resultant mixture was stirred at 0° C. for 5 minutes. The mixture was washed with diethyl ether. The aqueous phase was basified by the addition of 40% aqueous sodium hydroxide solution and extracted with diethyl ether. The organic phase was washed with a saturated brine solution, dried over magnesium sulphate and evaporated. The material so obtained was purified by column chromatography on reversed-phase silica using decreasingly polar mixtures of acetonitrile and a 1% solution of trifluoroacetic acid in water as eluent. There was thus obtained 5-methyl-2,3-methylenedioxyaniline (0.086 g) as a colourless oil;
NMR Spectrum: (CDCl$_3$) 2.2 (s, 3H), 3.08 (br s, 2H), 5.87 (s, 2H), 6.13 (d, 1H), 6.18 (d, 1H).
[28] The product gave the following characterising data;
NMR Spectrum: (CDCl$_3$) 3.32 (s, 3H), 3.77 (s, 3H), 4.03 (s, 3H), 4.32 (s, 2H), 5.96 (s, 2H), 6.63 (d, 1H), 6.72 (d, 1H), 6.77 (s, 1H), 7.02 (s, 1H), 7.37 (s, 1H), 8.61 (s, 1H);
Mass Spectrum: M + H$^+$ 394.
The 5-methoxymethyl-2,3-methylenedioxyaniline used as a starting material was prepared as follows:-
n-Butyllithium (1.6 M in hexane; 1.1 ml) was added dropwise to a solution of N-(5-bromo-2,3-methylenedioxyphenyl)-2,2,5,5-tetramethyl-1,2,5-azadisilolidine (0.6 g) in THF (12 ml) that had been cooled to −70° C. and the mixture was stirred at −70° C. for 1 hour. Bromomethyl methyl ether (0.314 g) was added and the mixture was stirred and allowed to warm to 0° C. during 2 hours. A 1N aqueous hydrochloric acid solution was added and the resultant mixture was stirred at 0° C. for 5 minutes. The mixture was washed with diethyl ether. The aqueous phase was basified by the addition of 40% aqueous sodium hydroxide solution and extracted with diethyl ether. The organic phase was washed with a saturated brine solution, dried over magnesium sulphate and evaporated. The material so obtained was purified by column chromatography on silica using a 4:1 mixture of tert-butyl methyl ether and isohexane as eluent. Thus was obtained 5-methoxymethyl-2,3-methylenedioxyaniline (0.163 g) as a colourless oil;

TABLE III-continued

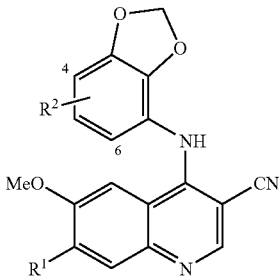

| Compound No. & Note | R¹ | R² |
|---|---|---|

NMR Spectrum: (CDCl₃) 3.34 (s, 3H), 3.58 (br s, 2H), 4.29 (s, 2H), 5.91 (s, 2H), 6.31 (d, 1H), 6.34 (d, 1H).

EXAMPLE 11

3-cyano-7-[(2R)-2-hydroxy-3-morpholinopropoxy]-6-methoxy-4-(2,3-methylenedioxyanilino)quinoline A mixture of 3-cyano-7-[(2R)-2,3-epoxypropoxy]-6-methoxy-4-(2,3-methylenedioxyanilino)quinoline (0.1 g), morpholine (0.11 g) and propanol (5 ml) was stirred and heated to 80° C. for 3 hours. The resultant mixture was evaporated and the residue was purified by column chromatography on silica using increasingly polar mixtures of methylene chloride and methanol as eluent. The material so obtained was triturated under diethyl ether to give the title compound (0.04 g); NMR Spectrum: (DMSOd₆) 2.35-2.52 (m, 6H), 3.56 (m, 4H), 3.93 (s, 3H), 4.04.1 (m, 2H), 4.17 (m, 1H), 4.9 (d, 1H), 5.98 (s, 2), 6.9-6.92 (m, 3H), 7.33 (s, 1H), 7.86 (s, 1H), 8.4 (s, 1H), 9.48 (br s, 1H); Mass Spectrum: M−H⁻ 477.

The 3-cyano-7-[(2R)-2,3-epoxypropoxy]-6-methoxy-4-(2,3-methylenedioxyanilino)quinoline used as a starting material was prepared as follows:—

(2R)-(−)-Glycidyl tosylate (0.52 g) was added to a mixture of 3-cyano-7-hydroxy-6-methoxy-4-(2,3-methylenedioxyanilino)quinoline (0.67 g), potassium carbonate (0.87 g) and DMA (15 ml) and the mixture was stirred and heated to 60° C. for 3 hours. The resultant mixture was evaporated and the residue was partitioned between methylene chloride and water. The organic phase was washed with water and with a saturated brine solution, dried over magnesium sulphate and evaporated. The residue was purified by column chromatography on silica using increasingly polar mixtures of methylene chloride and methanol as eluent. There was thus obtained 3-cyano-7-[(2R)-2,3-epoxypropoxy]-6-methoxy-4-(2,3-methylenedioxyanilino)quinoline as a solid (0.3 g); NMR Spectrum: (DMSOd₆) 2.75 (m, 1H), 2.88 (m, 1H), 3.4 (m, 1H), 3.95 (s, 3H), 3.954.01 (m, 1H), 4.53 (m, 1H), 5.98 (s, 2H), 6.8-6.92 (m, 3H), 7.33 (s, 1H), 7.79 (s, 1H), 8.41 (s, 1H), 9.1 (s, 1H); Mass Spectrum: M+H⁺ 392.

EXAMPLE 12

7-[(2R)-3-(4-acetylpiperazin-1-yl)-2-hydroxypropoxy]-3-cyano-6-methoxy-4-(2,3-methylenedioxyanilino)quinoline Using an analogous procedure to that described in Example 11, 3-cyano-7-[(2R)-2,3-epoxypropoxy]-6-methoxy-4-(2,3-methylenedioxyanilino)quinoline was reacted with 1-acetylpiperazine to give the title compound in 35% yield; NMR Spectrum: (DMSOd₆) 1.96 (s, 3H), 2.34-2.54 (m, 6H), 3.35-3.45 (m, 4H), 3.94 (s, 3H), 4.0-4.1 (m, 2H), 4.13-4.21 (m, 1H), 4.94 (d, 1H), 5.97 (s, 2H), 6.80-6.92 (m, 3H), 7.23 (s, 1H), 7.76 (s, 1H), 8.4 (s, 1H), 9.49 (s, 1H); Mass Spectrum: M+H⁺ 520.

EXAMPLE 13

3-cyano-7-[(2R)-2-hydroxy-3-methoxypropoxy]-6-methoxy-4-(2,3-methylenedioxyamino)quinoline A mixture of 3-cyano-7-[(2R)-2,3-epoxypropoxy]-6-methoxy-4-(2,3-methylenedioxyanilino)quinoline (0.1 g), a methanolic sodium methoxide solution (25%, 1 ml) and methanol (5 ml) was stirred at ambient temperature for 18 hours. The mixture was evaporated and the residue was dissolved in methylene chloride and washed with water and with a saturated brine solution and dried over magnesium sulphate. The organic phase was evaporated and the residue was was purified by column chromatography on silica using increasingly polar mixtures of methylene chloride and methanol as eluent. The resultant gum was triturated under diethyl ether to give the title compound as a solid (0.035 g); NMR Spectrum: (DMSOd₆) 3.29 (s, 3H), 3.32-3.49 (m, 2H), 3.94 (s, 3H), 3.98-4.17 (m, 3H), 5.15 (m, 1H), 5.98 (s, 2H), 6.89-6.92 (m, 3H), 7.3 (s, 1H), 7.78 (s, 1H), 8.4 (s, 1H), 9.48 (br s, 1H); Mass Spectrum: M+H⁺ 424.

EXAMPLE 14

3-cyano-6-methoxy-4-(2,3-methylenedioxyphenoxy)-7-[3-(4-methylpiperazin-1-yl)propoxy]quinoline Potassium carbonate-(0.055 g) was added to a solution of 2,3-methylenedioxyphenol (0.041 g) in DMF (3 ml) and the mixture was stirred at ambient temperature for 10 minutes. 4-Chloro-3-cyano-6-methoxy-7-[3-(4-methylpiperazin-1-yl)propoxy]quinoline (0.1 g) was added and the mixture was stirred and heated to 95° C. for 2 hours. The resultant mixture was cooled to ambient temperature and filtered. The filtrate was evaporated and the residue was purified by colum chromatography on silica using initially increasingly polar mixtures of methylene chloride and methanol followed by increasingly polar mixtures of methylene chloride and a saturated methanolic ammonia solution as eluent. There was thus obtained the title compound as a solid (0.069 g); NMR Spectrum: (DMSOd$_6$ and CF$_3$CO$_2$D) 2.3-2.4 (m, 2H), 3.0 (s, 3H), 3.2-4.0 (m, 8H), 3.5 (m, 2H), 3.95 (s, 3H), 4.4 (m, 2H), 6.05 (s, 2H), 6.8 (m, 1H), 6.9 (m, 2H), 7.6 (s, 1H), 7.62 (s, 1H), 9.1 (s, 1H); Mass Spectrum: M+H$^+$ 477.

The 4-chloro-3-cyano-6-methoxy-7-[3-(4-methylpiperazin-1-yl)propoxy]quinoline used as a starting material was prepared as follows:—

A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation at about 60-70° C. under about 0.2 mm Hg to give 1-(3-hydroxypropyl)-4-methylpiperazine (17 g); NMR Spectrum: (CDCl$_3$) 1.72 (m, 2H), 2.3 (s, 3H), 2.2-2.8 (m, 8), 2.6 (t, 2H), 3.8 (t, 2H), 5.3 (br s, 1H).

Diethyl azodicarboxylate (0.25 g) was added dropwise to a suspension of 4-chloro-3-cyano-7-hydroxy-6-methoxyquinoline (0.2 g), 1-(3-hydroxypropyl)-4-methylpiperazine (0.202 g), triphenyl phosphine (0.447 g) and methylene chloride (5 ml) and the mixture was stirred at ambient temperature for 2 hours. The resultant mixture was evaporated and the residue was purified by column chromatography on silica using initially increasingly polar mixtures of methylene chloride and ethyl acetate followed by increasingly polar mixtures of methylene chloride, ethyl acetate and a saturated methanolic ammonia solution as eluent. The material so obtained was triturated under diethyl ether. The resultant solid was isolated and dried under vacuum to give the required starting material (0.15 g); NMR Spectrum: (DMSOd$_6$ and CF$_3$CO$_2$D) 1.95-2.05 (m, 2H), 2.2 (s, 3H), 2.25-2.5 (m, 10H), 4.05 (s, 3H), 4.3 (m, 2H), 7.45 (s, 1H), 7.58 (s, 1H), 9.0 (s, 1H); Mass Spectrum: M+H$^+$ 375 and 377.

The 2,3-methylenedioxyphenol used as a starting material was prepared as follows:—3-Chloroperbenzoic acid (70% pure; 10.3 g) was added to a solution of 2,3-methylenedioxybenzaldehyde (3 g) in chloroform and the mixture was heated to reflux for 1 hour. The organic phase was washed in turn with a saturated aqueous sodium bicarbonate solution, water and a saturated brine solution, dried over magnesium sulphate and evaporated. A mixture of the material so obtained, 6N aqueous hydrochloric acid (90 ml) and methanol (90 ml) was stirred and heated to 80° C. for 30 minutes; The mixture was cooled to ambient temperature and concentrated by evaporation of the bulk of the solvent. The residue was partitioned between methylene chloride and a saturated aqueous sodium bicarbonate solution. The organic phase was washed with water and with a saturated brine solution, dried over magnesium sulphate and evaporated. The crude product so obtained was purified by column chromatography on silica using a 9:1 mixture of petroleum ether (b.p 40-60° C.) and ethyl acetate as eluent. There was thus obtained 2,3-methylenedioxyphenol as a solid (1.7 g); NMR Spectrum: (CDCl$_3$) 4.85 (br s, 1H), 5.95 (s, 2H), 6.45 (d, 1H), 6.5 (d, 1H), 6.75 (t, 1H).

EXAMPLE 15

4-(6-bromo-2,3-methylenedioxyphenoxy)-3-cyano-6-methoxy-7-[3-(4-methylpiperazin-1-yl)propoxy]quinoline Using an analogous procedure to that described in Example 14, 4chloro-3-cyano-6-methoxy-7-[3-(4-methylpiperazin-1-yl)propoxy]quinoline was reacted with 6-bromo-2,3-methylenedioxyphenol to give the title compound as a solid in 52% yield; NMR Spectrum: (DMSOd$_6$ and CF$_3$CO$_2$D) 2.25-2.4 (m, 2H), 2.95 (s, 3H), 3.24-4.0 (m, 8H), 3.48 (m, 2H), 3.98 (s, 3H), 4.35 (m, 2H) 6.02 (s, 1H), 6.08 (s, 1H), 6.92 (d, 1H), 7.25 (d, 1H), 7.6 (d, 2H), 8.9 (s, 1H); Mass Spectrum: M+H$^+$ 555 and 557.

The 6-bromo-2,3-methylenedioxyphenol used as a starting material was prepared as follows:—

A solution of bromine (0.074 ml) in chloroform (2 ml) was added dropwise to a stirred mixture of 2,3-methylenedioxyphenol (0.2 g), silver trifluoroacetate (0.32 g) and chloroform (3 ml) and the resultant mixture was stirred at ambient temperature for 2 hours. The mixture was filtered and the filtrate was adsorbed onto silica and purified by column chromatography on silica using a 9:1 mixture of petroleum ether (b.p. 40-60° C.) and ethyl acetate as eluent. There was thus obtained the desired material (0.217 g) as a solid; NMR Spectrum: (CDCl$_3$) 5.35 (s, 1H), 6.05 (s, 2H), 6.4 (d, 1H), 6.95 (d, 1H); Mass Spectrum: [M–H]$^-$215 and 217.

EXAMPLE 16

3-cyano-6-methoxy-4-(2,3-methylenedioxyamino)-7-(3-piperazin-1-ylpropoxy)quinoline A mixture of 7-[3-(4-tert-butoxycarbonylpiperazin-1-yl)propoxy]-3-cyano-6-methoxy-4-(2,3-methylenedioxyanilino)quinoline (0.2 g) and trifluoroacetic acid (2 ml) was stirred at ambient temperature for 40 minutes. The mixture was evaporated and the residue was partitioned between methylene chloride and a saturated aqueous sodium bicarbonate solution. The organic layer was dried over magnesium sulphate and evaporated. The residue was triturated under a 1:1 mixture of diethyl ether and isohexane. There was thus obtained the title compound as a solid (0.076 g); NMR Spectrum: (DMSOd$_6$) 1.93 (m, 2H), 2.4-2.64 (m, 6H), 3.1 (s, 4H), 3.95 (s, 3H), 4.22 (t, 2H, 5.98 (s, 2H), 6.8-6.95 (m, 3H), 7.33 (s, 1H), 7.79 (s, 1H), 8.43 (s, 1H), 8.53 (br s, 1H), 9.54 (s, 1H); Mass Spectrum: M–H$^-$ 460.

EXAMPLE 17

3cyano-4-(6-cyano-2,3-methylenedioxyanilino)-6,7-dimethoxyquinoline

Tris(dibenzylideneacetone)dipalladium (0.039 g) was added to a mixture of a 4:1 mixture (0.25 g) of 3-cyano-4-(6-iodo-2,3-methylenedioxyanilino)-6,7-dimethoxyquinoline and 3-cyano-4-(4,6-diiodo-2,3-methylenedioxyanilino)-6,7-dimethoxyquinoline (Example 10, Note [11]), zinc cyanide (0.092 g), diphenylphosphinoferrocene (0.046 g), zinc powder (0.017 g) and DMA (15 ml) and the resultant mixture was stirred and heated to 110° C. for 1 hour. The mixture was cooled to ambient temperature and partitioned between ethyl acetate and water. The organic layer was dried over magnesium sulphate and evaporated and the residue was purified by column chromatography on silica using increasingly polar mixtures of hexane and ethyl acetate as eluent. There were thus obtained in turn:—

3-cyano-4-(6-cyano-2,3-methylenedioxyanilino)-6,7-dimethoxyquinoline as a solid (0.082 g); NMR Spectrum: (DMSOd$_6$) 3.96 (s, 3H), 3.98 (s, 3H), 6.17 (s, 2H), 7.01 (s, 1H), 7.4 (s, 1H), 7.47 (d, 1H), 7.88 (s, 1H), 8.45 (s, 1H), 9.5 (br s, 1H); Mass Spectrum: M+H$^+$ 375; and 3-cyano-4-(4,6-dicyano-2,3-methylenedioxyanilino)-6,7-dimethoxyquinoline as a solid (0.012 g); NMR Spectrum: (DM- SOd$_6$) 3.89 (s, 3H), 3.98 (s, 3H), 6.24 (s, 2H), 7.21 (s, 1H), 7.8 (s, 2H), 8.45 (s, 1H), 11.7 (br s, 1H); Mass Spectrum: M+H$^+$400.

EXAMPLE 18

3-cyano-4-(4-cyano-2,3-methylenedioxyanilino)-6,7-dimethoxyquinoline

Tris(dibenzylideneacetone)dipalladium (0.0073 g) was added to a mixture of 3-cyano-4-(4-iodo-2,3methylenedioxyanilino)-6,7-dimethoxyquinoline (0.05 g) zinc cyanide (0.015 g), diphenylphosphinoferrocene (0.009 g), zinc powder (0.0035 g) and DMA (2 ml) and the resultant mixture was stirred and heated to 110° C. for 1 hour. The mixture was cooled to ambient temperature and partitioned between ethyl acetate and water. The organic layer was dried over magnesium sulphate and evaporated and the residue was purified by column chromatography on silica using increasingly polar mixtures of hexane and ethyl acetate as eluent. The material so obtained was triturated under diethyl ether. There was thus obtained 3-cyano-4-(4-cyano-2,3-methylenedioxyamino)-6.7-dimethoxyquinoline as a solid (0.014 g); NMR Spectrum: (CDCl$_3$) 3.84 (s, 3H), 4.07 (s, 3H), 6.16 (s, 2H), 6.28 (d, 1H), 6.75 (s, 1H), 6.99 (m, 2H), 7.46 (s, 1H), 8.73 (s, 1H); Mass Spectrum: M+H$^+$ 375.

EXAMPLE 19

4-(6-chloro-4-cyano-2,3-methylenedioxyamino)$_3$-cyano-6,7-dimethoxyquinoline

Tris(dibenzylideneacetone)dipalladium (0.039 g) was added to a mixture of 4-(6-chloro-4-iodo-2,3-methylenedioxyamino)-3-cyano-6,7-dimethoxyquinoline (0.268 g), zinc cyanide (0.086 g), diphenylphosphinoferrocene (0.046 g), zinc powder (0.017 g) and DMA (15 ml) and the resultant mixture was stirred and heated to 110° C. for 1 hour. The mixture was cooled to ambient temperature and partitioned between ethyl acetate and water. The organic layer was dried over magnesium sulphate and evaporated and the residue was purified by column chromatography on silica using increasingly polar mixtures of hexane and ethyl acetate as eluent. The material so obtained was triturated under diethyl ether. There was thus obtained 3cyano-4-(4-cyano-2,3-methylenedioxyaniline as a solid (0.11 g); NMR Spectrum: DMSOd$_6$) 3.94 (s, 3H), 3.98 (s, 3H), 6.21 (s, 2H), 7.28 (s, 1H), 7.4 (s, 1H), 7.79 (s, 1H), 8.36 (s, 1H); Mass Spectrum: M+H$^+$ 409 and 411.

EXAMPLE 20

3-cyano-4-(4-cyano-2,3-methylenedioxyanilino)-6-methoxy-7-[3-(4-methylpiperazin-1-yl)propoxy]quinoline Using an analogous procedure to that described in Example 19, 3-cyano-4-(4-iodo-2,3-methylenedioxyanilino)-6-methoxy-7-[3-(4-methylpiperazin-1-yl)propoky]quinoline (0.316 g) was reacted with zinc cyanide (0.086 g) to give the title compound as a solid (0.014 g); NMR Spectrum: (DMSOd$_6$) 1.96 (m, 2H), 2.18 (s, 3H), 2.25-2.5 (m, 10H), 3.94 (s, 3H), 4.18 (t, 2H), 6.16 (s, 2H), 6.94 (d, 1H), 7.3 (d, 1H), 7.37 (s, 1H), 7.72 (s, 1H), 8.61 (s, 1H), 9.87 (br s, 1H); Mass Spectrum: M–H$^-$ 499.

EXAMPLE 21

3-cyano-4-(4-ethynyl-2,3-methylenedioxyanilino)-6,7-dimethoxyquinoline

A mixture of 3-cyano-4-(4-iodo-2,3-methylenedioxyanilino)-6,7-dimethoxyquinoline (0.2 g), trimethylsilylacetylene (0.11 ml), tetrakis(triphenylphosphine)palladium(0) (0.05 g), cuprous iodide (0.01 g) and N,N-diethylamine (4 ml) was stirred and heated to 60° C. for 4 hours. The reaction mixture was evaporated and the residue was partitioned between methylene chloride and a 2N aqueous hydrochloric acid solution. The precipitate that was formed was isolated by filtration, washed with methylene chloride and dried. There was thus obtained 3-cyano-6,7-dimethoxy-4-(2,3-methylenedioxy-4-trimethylsilylethynylanilino)quinoline as a solid (0.08 g); Mass Spectrum: M+H$^+$ 446.

A mixture of the material so obtained, potassium carbonate (0.07 g), water (1 ml) and methanol (5 ml) was stirred at ambient temperature for 2 hours. The reaction mixture was evaporated and the residue was purified by column chromatography on silica using increasingly polar mixtures of methylene chloride and ethyl acetate as eluent. The material so obtained was dissolved in a mixture of methylene chloride and diethyl ether and a 1M solution of hydrogen chloride in diethyl ether was added. The resultant solid was isolated, washed with diethyl ether and dried. There was thus obtained the title compound as a hydrochloride salt (0.055 g); NMR Spectrum: DMSOd$_6$) 3.99 (s, 3H), 4.0 (s, 3H), 4.46 (s, 1H), 6.22 (s, 2H), 6.97 (d, 1H), 7.04 (d, 1), 7.47 (s, 1H), 8.15 (s, 1H), 8.97 (s, 1H); Mass Spectrum: M+H$^+$ 374.

EXAMPLE 22

3-cyano-6-methoxy-4-(2,3-methylenedioxy-4-phenylanilino)-7-[3-(4-methylpiperazin-1-yl)propoxy]quinoline A mixture of 3-cyano-4-(4-iodo-2,3-methylenedioxyanilino)-6-methoxy-7-[3-(4-methylpiperazin-1-yl)propoky]quinoline (0.15 g), phenylboronic acid (0.046 g), tetrakis(triphenylphosphine)palladium(0) (0.01 g), a saturated aqueous sodium bicarbonate solution (2 ml) and 1,2-dimethoxyethane (18 ml) was stirred and heated to 80° C. for 5 hours. The reaction mixture was cooled to ambient temperature and partitioned between ethyl acetate and water. The organic layer was dried over magnesium sulphate and evaporated. The residue was purified by column chromatography on silica using increasingly polar mixtures of methylene chloride and methanol as eluent. The material so obtained was triturated under diethyl ether. There was thus obtained the title compound as a solid (0.085 g); NMR Spectrum: (DMSOd$_6$) 1.95 (m, 2H), 2.17 (s, 3H), 2.24-2.59 (m, 10H), 3.96 (s, 3H), 4.17 (t, 2H), 6.06 (s, 2H), 6.94 (d, 1H), 7.23 (d, 1H), 7.3 (s, 1H), 7.37 (t, 1H), 7.46 (t, 2H), 7.76 (d, 2H), 7.77 (s, 1H), 8.43 (s, 1H), 9.55 (s, 1H); Mass Spectrum: M–H$^-$ 550.

EXAMPLE 23

3-cyano-6,7-dimethoxy-4-(2,3-methylenedioxy-4-methylsulphonylanilino)quinoline

3-Chloroperoxybenzoic acid (700 technical grade; 0.05 g) was added in one portion to a stirred solution of 3-cyano-6, 7-dimethoxy-4-(2,3-methylenedioxy-4-methylthioanilino) quinoline (0.04 g) in chloroform (5 ml) and the mixture was stirred at ambient temperature for 18 hours. The reaction mixture was evaporated to dryness under reduced pressure whilst being cooled to 0° C. The material so obtained was purified by column chromatography on silica using increasingly polar mixtures of methylene chloride and methanol as eluent. There was thus obtained the title compound as a solid (0.016 g); NMR Spectrum: (DMSOd$_6$) 3.13 (s, 3H), 3.82 (s, 3H), 3.88 (s, 3H), 6.05 (s, 2H), 6.62 (d, 1H), 7.03 (d, 1H), 7.09 (s, 1H), 7.7 (s, 1H), 8.1 (s, 1H); Mass Spectrum: M+H$^+$ 428.

EXAMPLE 24

3-cyano-4-[4-(2-cyanoethyl)-2,3-methylenedioxyamino]-6,7-dimethoxyquinoline

A mixture of 3-[4-(3-cyano-6,7-dimethoxyquinolin-4-ylamino)-2,3-methylenedioxyphenyl]acrylonitrile (0.15 g), 10% palladium-on-carbon (0.025 g), methanol (2 ml) and ethyl acetate (3 ml) was stirred at ambient-temperature under an atmosphere pressure of hydrogen for 12 hours. DMF (1.5 ml) was added and reaction mixture was stirred under an atmosphere pressure of hydrogen for a further 12 hours. The mixture was filtered and the filtrate was evaporated. The residue was purified by column chromatography on silica using increasingly polar mixtures of hexane and ethyl acetate as eluent. The material so obtained was triturated under diethyl ether. There was thus obtained the title compound as a solid (0.085 g); NMR Spectrum: (DMSOd$_6$) 2.75-2.89 (m, 4H), 3.91 (s, 3H), 3.93 (s; 3H), 5.99 (s, 2H) 6.78-6.88 (m, 2H), 7.3 (s, 1H), 7.75 (s, 1H), 8.43 (s, 1H), 9.46 (s, 1H); Mass Spectrum: M+H$^+$ 403.

The 3-[4-(3-cyano-6,7-dimethoxyquinolinylamino)-2,3-methylenedioxyphenyl]acrylonitrile used as a starting material was prepared as follows:—

A mixture of 3-cyano-4-(4-iodo-2,3-methylenedioxyanilino)-6,7-dimethoxyquinoline (0.2 g), acrylonitrile (0.2 ml), triethylamine (0.2 ml), palladium(II) acetate (0.01 g) and DMF (2 ml) was stirred and heated to 115° C. for 3 hours. The reaction mixture was evaporated and the residue was purified by column chromatography on silica using increasingly polar mixtures of hexane and ethyl acetate as eluent. The material so obtained was triturated under diethyl ether. There was thus obtained the required starting material, in the form of a 4:1 mixture of trans and cis isomers and as a yellow solid (0.095 g); NMR Spectrum: (DMSOd$_6$, data relating to the major trans isomer) 3.91 (s, 3H), 3.93 (s, 3H), 6.12 (s, 2H), 6.26 (d, 1H), 6.88 (d, 1H), 7.14 (d, 1H), 7.35 (s, 1H), 7.56 (d, 1H), 7.7 (s, 1H), 8.51 (s, 1H), 9.7 (s, 1H); Mass Spectrum: M+H$^+$ 401.

EXAMPLE 25

3-cyano-4-(5-cyano-2,3-methylenedioxyanilino)-6,7-dimethoxyquinoline

Using an analogous procedure to that described in Example 19 except that the reaction mixture was heated to 110° C. for 4 hours, 4-(5-bromo-2,3-methylenedioxyanilino)-3-cyano-6,7-dimethoxyquinoline (0.25 g) was reacted with zinc cyanide (0.082 g) to give the title compound as a solid (0.14 g); NMR Spectrum: (DMSOd$_6$) 3.94 (s, 3H), 3.95 (s, 3H), 6.15 (s, 2H), 7.35 (d, 1H), 7.39 (d, 1H), 7.44 (s, 1H), 7.75 (s, 1H), 8.53 (s, 1H), 9.71 (s, 1H); Mass Spectrum: M+H$^+$ 375.

EXAMPLE 26

3-cyano-6,7-dimethoxy-4-(2,3-ethylidenedioxyanilino)quinoline

Using an analogous procedure to that described in Example 1, 4-chloro-3-cyano-6,7-dimethoxyquinoline was reacted with 2,3-ethylidenedioxyaniline to give the title compound; NMR Spectrum: (DMSOd$_6$) 1.55 (d, 3H), 3.95 (s, 3H), 3.96 (s, 3H), 6.34 (q, 1H), 6.75-6.9 (m, 3H), 7.3 (s, 1H), 7.75 (s, 1H), 8.2 (s, 1H), 9.45 (s, 1H); Mass Spectrum: M+H$^+$ 364.

The 2,3-ethylidenedioxyaniline used as a starting material was prepared as follows:—

A mixture of 3-nitrocatechol (*J. Heterocyclic Chem.,* 1991, 28, 625; 1.6 g), 1,1-dibromoethane (1.4 ml), caesium carbonate (5 g) and DMF (30 ml) was stirred and heated to 110° C. for 1 hour. Further quantities of caesium carbonate (5 g) and 1,1-dibromoethane (1.4 ml) were added every hour for a further 5 hours and the resultant mixture was stirred at 110° C. for a further 0.5 hours. The mixture was cooled to ambient temperature and partitioned between ethyl acetate and water. The organic phase was washed with a saturated brine solution, dried over sodium sulphate and evaporated. The residue was purified by column chromatography using a 9:1 mixture of isohexane and ethyl acetate as eluent. There was thus obtained 2,3-ethylidenedioxy-1-nitrobenzene as a yellow solid (0.853 g); NMR Spectrum: (CDCl$_3$) 1.8 (d, 3H); 6.5 (q, 1H), 6.9 (t, 1H), 7.0 (d, 1H), 7.58 (d, 1H).

A mixture of the material so obtained, 10% palladium-on-carbon (0.083 g) and ethyl acetate (33 ml) was stirred at ambient temperature under an atmosphere pressure of hydrogen for 3 hours. The catalyst was removed by filtration and the solvent was evaporated. There was thus obtained 2,3-ethylidenedioxyaniline (0.683 g) as an oil; NMR Spectrum (CDCl$_3$) 1.68 (d, 3H), 3.5 (s, 2H), 6.2 (q, 1H), 6.28 (d, 2H), 6.63 (t, 1H).

EXAMPLE 27

3-cyano-6,7-dimethoxy-4-(2,3-propylidenedioxyanilino)quinoline

Using an analogous procedure to that described in Example 1, 4-chloro-3-cyano-6,7-dimethoxyquinoline was reacted with 2,3-propylidenedioxyaniline to give the title compound; NMR Spectrum: (DMSOd$_6$) 0.95 (t, 3H), 1.9 (m, 2H), 3.7 (s, 3H), 4.03 (s, 3H), 6.07 (t, 1H), 6.62 (d, 1H), 6.67 (s, 1H), 6.7 (d, 1H), 6.8 (t, 1H), 6.98 (s; 1H), 7.35 (s, 1H), 8.63 (s, 1H); Mass Spectrum: M+H$^+$ 378.

The 2,3-propylidenedioxyaniline used as a starting material was prepared as follows:—

A mixture of 3-nitrocatechol (1.3 g), 1,1-dichloropropane (1.35 ml), caesium carbonate (4.4 g) and DMF (27 ml) was stirred and heated to 90° C. for 1 hour. Maintaining this reaction temperature, further quantities of caesium carbonate (4.4 g) and 1,1-dichloroethane (1.35 ml) were added every hour for a further 14 hours and, in addition, potassium bromide (2.5 g) was added after 4 hours and 7 hours respectively. The resultant mixture was cooled to ambient temperature and partitioned between ethyl acetate and water. The organic phase was washed with a saturated brine solution, dried over sodium sulphate and evaporated. The residue was purified by column chromatography using a 9:1 mixture of isohexane and ethyl acetate as eluant. There was thus obtained 2,3-propylidenedioxy-1-nitrobenzene as a yellow solid (0.126 g); NMR Spectrum: (CDCl$_3$) 1.1 (t, 3H), 2.1 (m, 2H), 6.31 (t, 1H), 6.88 (t, 1H), 7.0 (d, 1H), 7.58 (d, 1H).

A mixture of the material so obtained, 10% palladium-on-carbon (0.011 g) and ethyl acetate (5 ml) was stirred at ambient temperature under an atmosphere pressure of hydrogen for 3 hours. The catalyst was removed by filtration and the solvent was evaporated. There was thus obtained 2,3-ethylidenedioxyaniline (0.1 g) as an oil; NMR Spectrum: (CDCl$_3$) 1.1 (t, 3H), 1.98 (m, 2H), 3.5 (s, 2H), 6.05 (t, 1H), 6.28 (2d, 2), 6.62 (t, 1H).

EXAMPLE 28

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |

-continued

| | |
|---|---|
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note
The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:
1. A quinoline compound of the Formula I

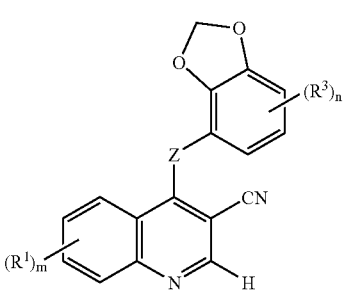

wherein:
Z is O or NH;
m is 2 and the first R$^1$ group is a 6-methoxy group and the second R$^1$ group is located at the 7-position and is selected from 2-pyrrolidin-1-ylethoxy, 3-pyrrolidin-1-ylpropoxy, 4-pyrrolidin-1-ylbutoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, N-cyanomethylpiperidin-3-ylmethoxy, piperidin-4-ylmethoxy, N-methylpiperidin-4-ylmethoxy, N-cyanomethylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-homopiperidin-1-ylethoxy, 3-homopiperidin-1-ylpropoxy, 4-homopiperidin-1-ylbutoxy, 2-piperazin-1-ylethoxy, 2-(4-methylpiperazin-1-yl)ethoxy, 3-piperazin-1-ylpropoxy, 3-(4-methylpiperazin-1-yl)propoxy, 4-piperazin-1-ylbutoxy, 4-(4-methylpiperazin-1-yl)butoxy, 2-(4-cyanomethylpiperazin-1-yl)ethoxy, 3-(4-cyanomethylpiperazin-1-yl)propoxy, 4-(4-cyanomethylpiperazin-1-yl)butoxy, 2-(2-piperazin-1-ylethoxy)ethoxy, 2-[2-(4-methylpiperazin-1-yl)ethoxy]ethoxy, 2-tetrahydropyran-4-ylethoxy, 3-tetrahydropyran-4-ylpropoxy, 2-pyrrol-1-ylethoxy, 3-pyrrol-1-ylpropoxy, 2-(2-pyridyloxy)ethoxy, 3-(2-pyridyloxy)propoxy, 2-(3-pyridyloxy)ethoxy, 3-(3-pyridyloxy)propoxy, 2-(4-pyridyloxy)ethoxy, 3-(4-pyridyloxy)propoxy, 2-pyridylmethoxy, 3-pyridylmethoxy and 4-pyridylmethoxy, and wherein any CH$_2$ group within the second R$^1$ group that is attached to two carbon atoms optionally bears a hydroxy group on said CH$_2$ group, and wherein any heteroaryl group within the second R$^1$ group optionally bears 1 or 2 substituents selected from chloro, cyano, hydroxy and methyl, and any heterocyclyl group within the second R$^1$ group optionally bears 1 or 2 substituents selected from hydroxy, methyl and oxo; and n is 1 and the R$^3$ group is located at the 6-position of the 2,3-methylenedioxyphenyl group and is selected from chloro and bromo;

or a pharmaceutically-acceptable acid-addition salt thereof.

2. A quinoline compound of the Formula I

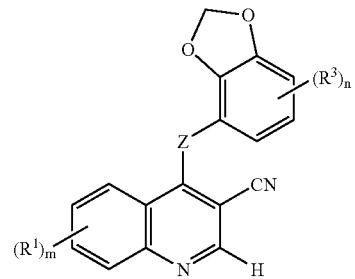

wherein:
Z is NH or O;
m is 2 and the first R$^1$ group is a 6-methoxy group and the second R$^1$ group is located at the 7-position and is selected from 3-pyrrolidin-1-ylpropoxy, 3-(3-fluoropyrrolidin-1-yl)propoxy, 3-(3,3-difluoropyrrolidin-1-yl)propoxy, 3-(2,5-dimethyl-3-pyrrolin-1-yl)propoxy, 3-morpholinopropoxy, 2-hydroxy-3-morpholinopropoxy, 2-fluoro-3-morpholinopropoxy, 3-(1,1-dioxotetrahydro-4H-1,4-thiazin-4-yl)propoxy, 3-piperidinopropoxy, 3-(4-hydroxypiperidin-1-yl)propoxy, 3-(4-fluoropiperidin-1-yl)propoxy, 3-(4,4-difluoropiperidin-1-yl)propoxy, 3-(1,2,3,6-tetrahydropyridin-1-yl)propoxy, 2-fluoro-3-(1,2,3,6-tetrahydropyridin-1-yl)propoxy, 4-(1,2,3,6-tetrahydropyridin-1-yl)butoxy, 3-piperazin-1-ylpropoxy, 2-(4-methylpiperazin-1-yl)ethoxy, 3-(4-methyipiperazin-1-yl)propoxy, 2-fluoro-3-(4-methylpiperazin-1-yl)propoxy, 4-(4-methylpiperazin-1-yl)butoxy, 2-(4-allylpiperazin-1-yl)ethoxy, 3-(4-allylpiperazin-1-yl)propoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 3-(4-acetylpiperazin-1-yl)-2-hydroxypropoxy and 3-(4-cyanomethylpiperazin-1-yl)propoxy; and
n is 1 or 2 and each R$^3$ group is selected from fluoro, chloro, bromo, iodo, cyano, methyl, ethyl, ethynyl, methylthio, methylsulphonyl, hydroxymethyl, methoxymethyl, 2-methoxyethyl, 2-cyanoethyl, dimethylaminomethyl, phenyl and benzyl;
or a pharmaceutically-acceptable acid-addition salt thereof.

3. A pharmaceutical composition which comprises a quinoline compound of the Formula I, or a pharmaceutically-acceptable salt thereof, according to claim 1 or claim 2 in association with a pharmaceutically-acceptable diluent or carrier.

* * * * *